US012630638B2

(12) United States Patent
Tudzarova-Trajkovska

(10) Patent No.: US 12,630,638 B2
(45) Date of Patent: May 19, 2026

(54) METHODS AND COMPOSITIONS FOR DIABETES TREATMENT AND β-CELL REGENERATION

(71) Applicant: THE REGENTS OF THE UNIVERSITY OF CALIFORNIA, Oakland, CA (US)

(72) Inventor: Slavica Tudzarova-Trajkovska, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 595 days.

(21) Appl. No.: 18/042,158

(22) PCT Filed: Aug. 17, 2021

(86) PCT No.: PCT/US2021/046267
§ 371 (c)(1),
(2) Date: Feb. 17, 2023

(87) PCT Pub. No.: WO2022/040161
PCT Pub. Date: Feb. 24, 2022

(65) Prior Publication Data
US 2023/0312728 A1      Oct. 5, 2023

Related U.S. Application Data

(60) Provisional application No. 63/169,776, filed on Apr. 1, 2021, provisional application No. 63/067,187, filed on Aug. 18, 2020.

(51) Int. Cl.
| | |
|---|---|
| *A61K 31/444* | (2006.01) |
| *A61K 31/18* | (2006.01) |
| *A61K 31/4709* | (2006.01) |
| *A61K 31/713* | (2006.01) |
| *A61P 3/08* | (2006.01) |
| *A61P 3/10* | (2006.01) |
| *C07K 16/28* | (2006.01) |
| *C12N 5/0735* | (2010.01) |
| *C12N 5/074* | (2010.01) |

(52) U.S. Cl.
CPC ........ *C07K 16/2857* (2013.01); *A61K 31/444* (2013.01); *A61K 31/4709* (2013.01); *A61K 31/713* (2013.01); *A61P 3/08* (2018.01); *C12N 5/0606* (2013.01); *C12N 5/0696* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 7,083,802 B2 * | 8/2006 | Peyman | A61P 19/02 424/428 |
| 2009/0029904 A1 * | 1/2009 | Oldham | A61P 3/10 435/6.16 |
| 2009/0074884 A1 | 3/2009 | Chesney et al. | |
| 2010/0267815 A1 | 10/2010 | Telang et al. | |
| 2012/0114637 A1 * | 5/2012 | Nivaggioli | A61K 9/0048 514/318 |
| 2012/0177749 A1 | 7/2012 | Tapolsky et al. | |
| 2013/0059879 A1 | 3/2013 | Chand et al. | |
| 2014/0127278 A1 * | 5/2014 | Hossainy | A61P 43/00 514/180 |
| 2014/0228357 A1 * | 8/2014 | Lee | A61K 31/5375 544/391 |
| 2015/0210759 A1 | 7/2015 | Grimm et al. | |
| 2016/0271157 A1 * | 9/2016 | Ahmed | A61P 3/10 |
| 2022/0287999 A1 * | 9/2022 | Pereira | A61K 31/198 |
| 2024/0262916 A1 * | 8/2024 | Tudzarova-Trajkovska | C12N 15/1138 |
| 2024/0269111 A1 * | 8/2024 | Roux | A61K 31/403 |
| 2024/0269124 A1 * | 8/2024 | Tudzarova-Trajkovska | A61P 25/02 |
| 2025/0074989 A1 * | 3/2025 | Tudzarova-Trajkovska | A61K 31/517 |

FOREIGN PATENT DOCUMENTS

| | | |
|---|---|---|
| WO | WO 2012/082765 | 6/2012 |
| WO | WO 2015/171723 | 11/2015 |
| WO | WO 2017/208174 | 12/2017 |
| WO | WO-2020080979 A1 * | 4/2020 ........... A61K 31/713 |

OTHER PUBLICATIONS

Bessho et al. (2019) Scientific Reports 9:14754, p. 1-12.*
Han et al. Journal of Endocrinology (2019) 241, 85-98.*
Pezzilli et al. World J Diabetes (2014); 5(4): 415-419.*
Murphy et al. (2020) NeuroRehabilitation 47: 265-284.*
Alvarez-Dominguez, et al. "Circadian Entrainment triggers maturation of human in vitro islets", *Cell Stem Cell.* vol. 26, pp. 108-122, 2020.
Botusan, et al. "Stabilization of HIF-1alpha is critical to improve wound healing in diabetic mice", *Proc Natl Acad Sci USA,* 105(49), pp. 19426-19431, 2008.
Erener S. et al. "Characterization of polyhormonal insulin-producing cells derived in vitro from human embryonic stem cells", *Stem Cell Res.* vol. 12, pp. 194-208, 2014.
International Search Report and Written Opinion issued in corresponding International application PCT/US2021/046267 mailed Jan. 10, 2022.

(Continued)

*Primary Examiner* — Ilia I Ouspenski
(74) *Attorney, Agent, or Firm* — Norton Rose Fulbright US LLP

(57) ABSTRACT

Aspects of the present disclosure are directed to methods and compositions for facilitating β-cell regeneration by inhibition of the HIF1α-PFKFB3 pathway. Certain aspects describe methods for treatment and prevention of prediabetes and diabetes, including type 2 diabetes. Also disclosed are methods and compositions for enhancing β-cell regeneration.

14 Claims, 42 Drawing Sheets

Specification includes a Sequence Listing.

(56)        References Cited

OTHER PUBLICATIONS

Min, et al. "PFKF83 Depletion Activates β-Cell Replication by Cell Competitive Culling of Compromised β-Cells under stress", *bioRxiv,* 2021.

Montemurro, et al. "iAPP toxicity activates HiFa/PFKFB3 signaling delaying β-cells loss at the expense of β-cell function," *Nature Communications,* vol. 10, No. 1, pp. 2679, 2019.

Nauta, et al. "Hypoxic signaling during tissue repair and regenerative medicine", *Int J Mol Sci.,* vol. 15, pp. 19791-19815, 2014.

Onnis et al.,"Development of HIF-1 inhibitors for cancer therapy." *J. Cell. Mol. Med.* Sep. 13, 2009 (9a): 2780-2786.

Spijker et al., "Loss of β-Cell Identity Occurs in Type 2 Diabetes and is Associated with Islet Amyloid Deposits," *Diabetes,* vol. 65, pp. 2928-2938, 2015.

Zehetner, et al. "PVHL is a regulator of glucose metabolism and insulin secretion in pancreatic beta cells", *Genes Dev,* vol. 22, pp. 3135-3146, 2008.

Hiroshi, N. et al., "Activation of the HIF1 [alpha]/PFKFB3 stress response pathway in beta cells in type 1 diabetes", *Diabetologia,* 63(1), pp. 149-161, 19.

Changtao, J. et al., "Disruption of Hypoxia-Inducible Factor 1 in Adipocytes Improves Insulin Sensitivity and Decreases Adiposity in High-Fat Diet-Fed Mice", *Diabetes,* 60(10); pp. 2484-2495, 2011.

* cited by examiner

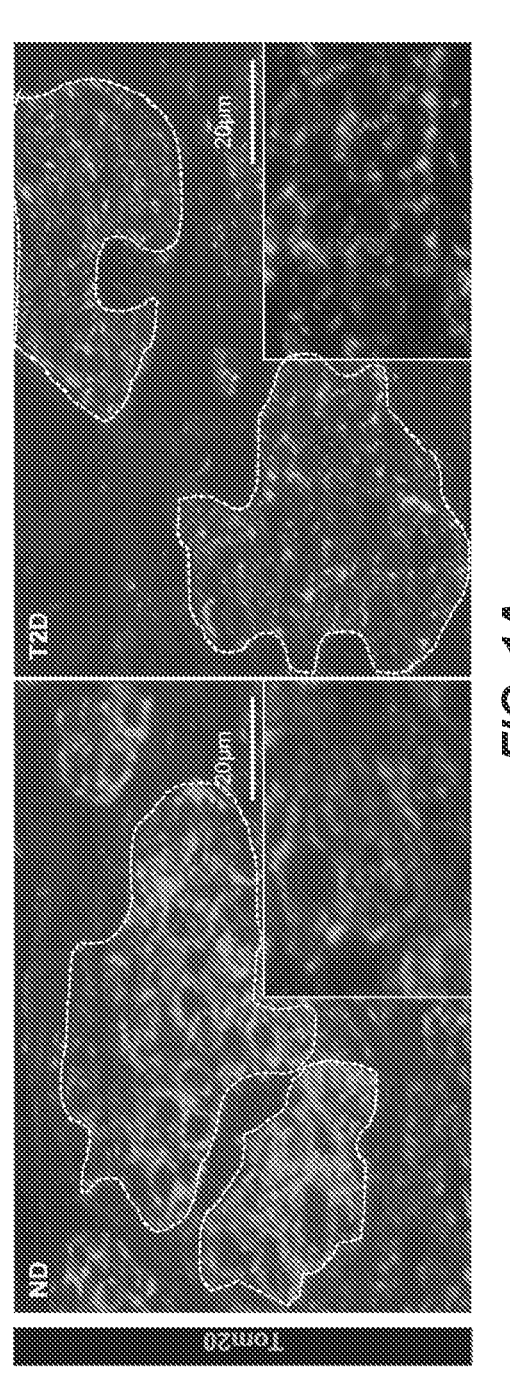
*FIG. 1A*
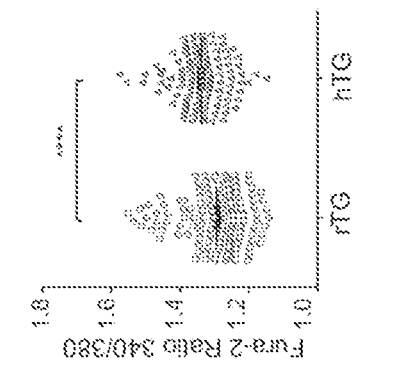
*FIG. 1C*
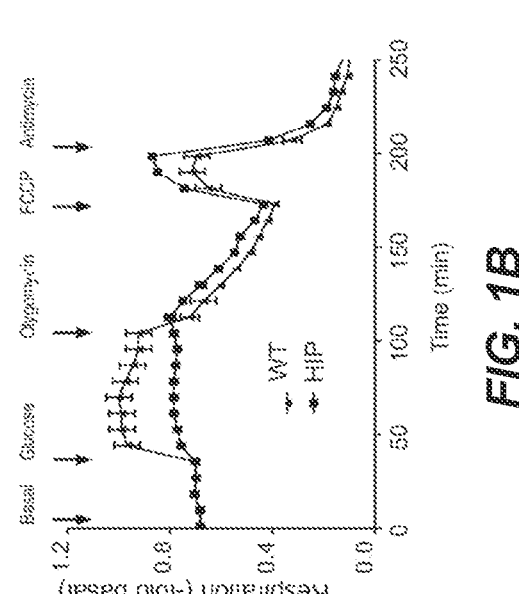
*FIG. 1B*
*FIG. 1D*

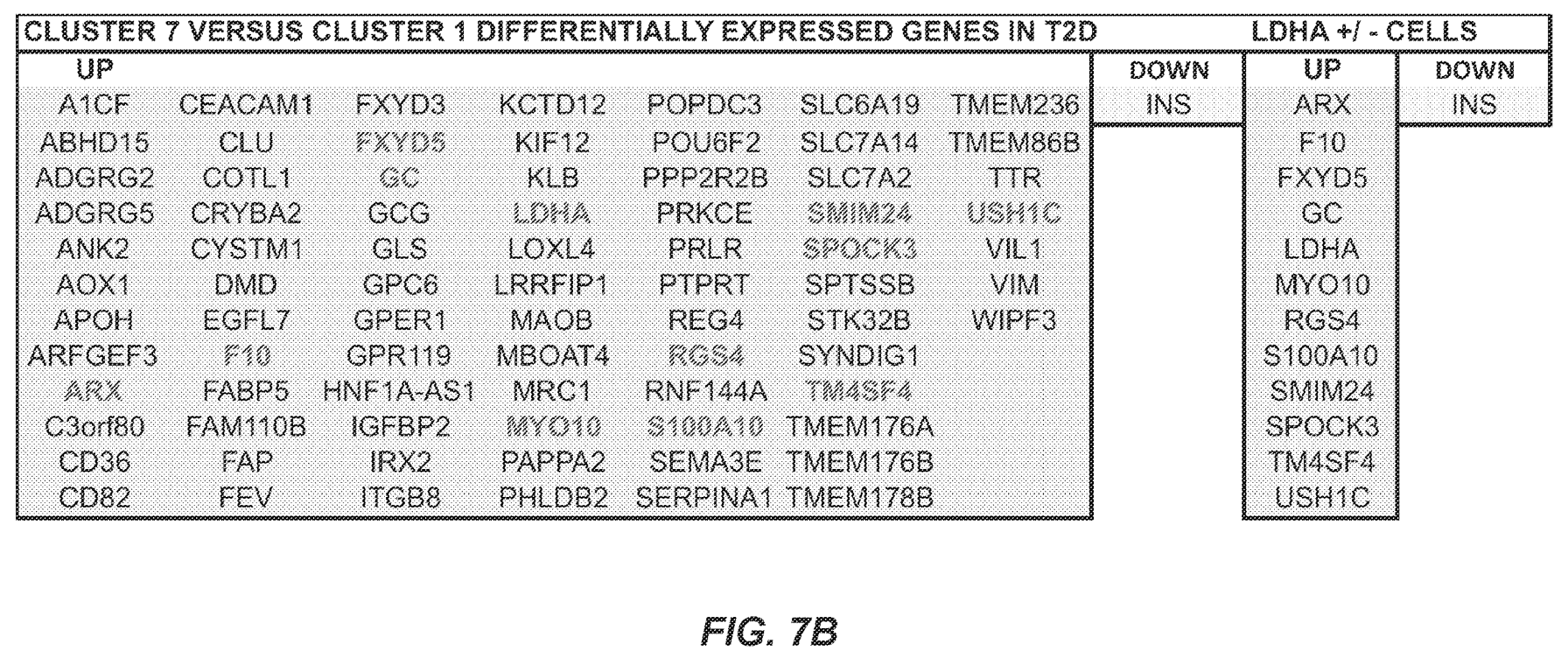

| CLUSTER 7 VERSUS CLUSTER 1 DIFFERENTIALLY EXPRESSED GENES IN T2D | | | | | | | | DOWN | LDHA +/- CELLS | | DOWN |
|---|---|---|---|---|---|---|---|---|---|---|---|
| UP | | | | | | | | INS | UP | | INS |
| A1CF | CEACAM1 | FXYD3 | KCTD12 | POPDC3 | SLC6A19 | TMEM236 | | | ARX | | |
| ABHD15 | CLU | FXYD5 | KIF12 | POU6F2 | SLC7A14 | TMEM86B | | | F10 | | |
| ADGRG2 | COTL1 | GC | KLB | PPP2R2B | SLC7A2 | TTR | | | FXYD5 | | |
| ADGRG5 | CRYBA2 | GCG | LDHA | PRKCE | SMIM24 | USH1C | | | GC | | |
| ANK2 | CYSTM1 | GLS | LOXL4 | PRLR | SPOCK3 | VIL1 | | | LDHA | | |
| AOX1 | DMD | GPC6 | LRRFIP1 | PTPRT | SPTSSB | VIM | | | MYO10 | | |
| APOH | EGFL7 | GPER1 | MAOB | REG4 | STK32B | WIPF3 | | | RGS4 | | |
| ARFGEF3 | F10 | GPR119 | MBOAT4 | RGS4 | SYNDIG1 | | | | S100A10 | | |
| ARX | FABP5 | HNF1A-AS1 | MRC1 | RNF144A | TM4SF4 | | | | SMIM24 | | |
| C3orf80 | FAM110B | IGFBP2 | MYO10 | S100A10 | TMEM176A | | | | SPOCK3 | | |
| CD36 | FAP | IRX2 | PAPPA2 | SEMA3E | TMEM176B | | | | TM4SF4 | | |
| CD82 | FEV | ITGB8 | PHLDB2 | SERPINA1 | TMEM178B | | | | USH1C | | |

*FIG. 7B*

HIF1α insulin DAPI

PFKFB3^WT/hIAPP-/-
PFKFB3^WT/hIAPP+/-
PFKFB3^βKO/hIAPP+/-

HIF1α positive β-cells (%)

30.0    20.0    10.0    0.0

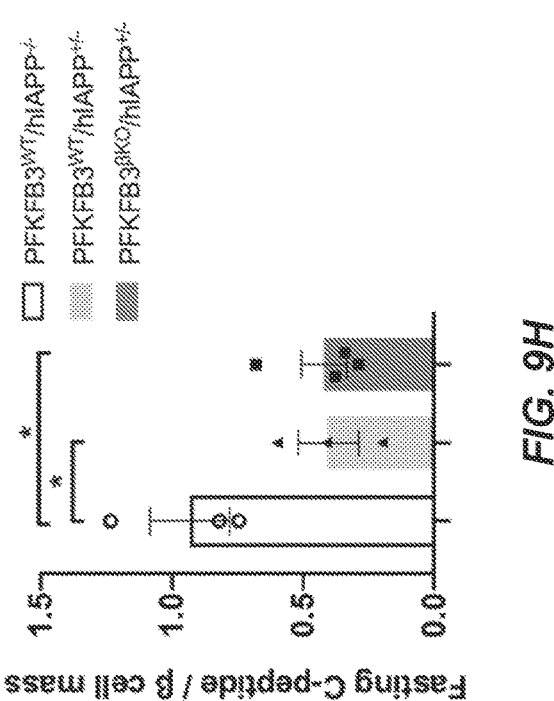
FIG. 9H
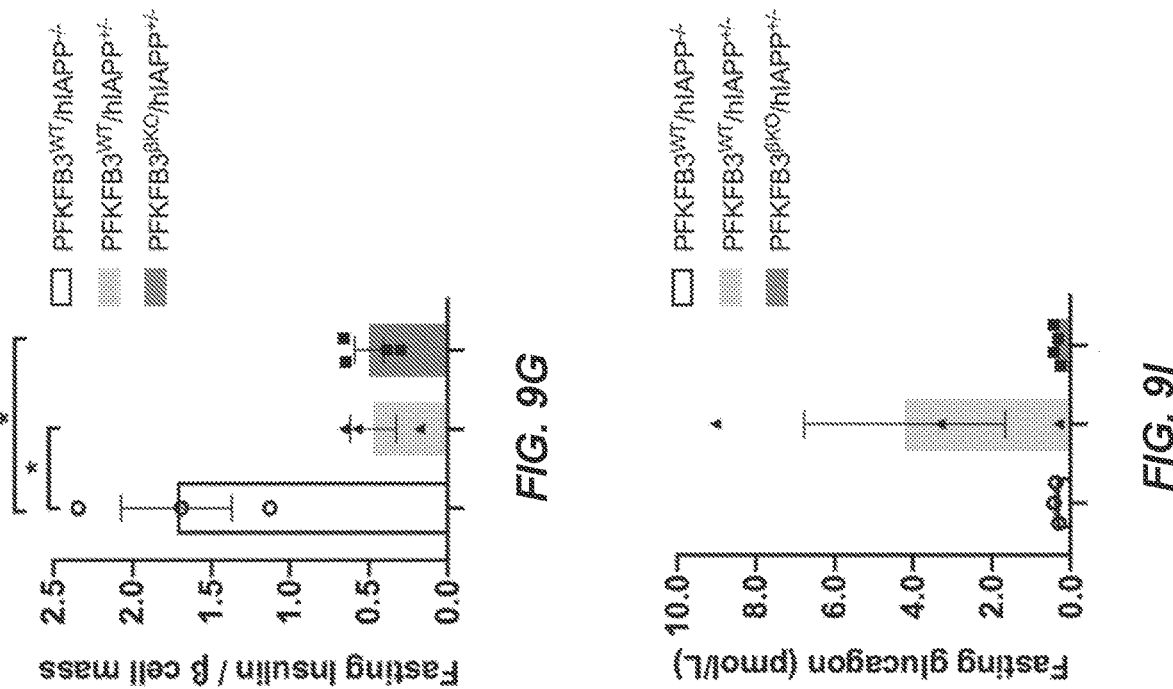
FIG. 9G
FIG. 9I

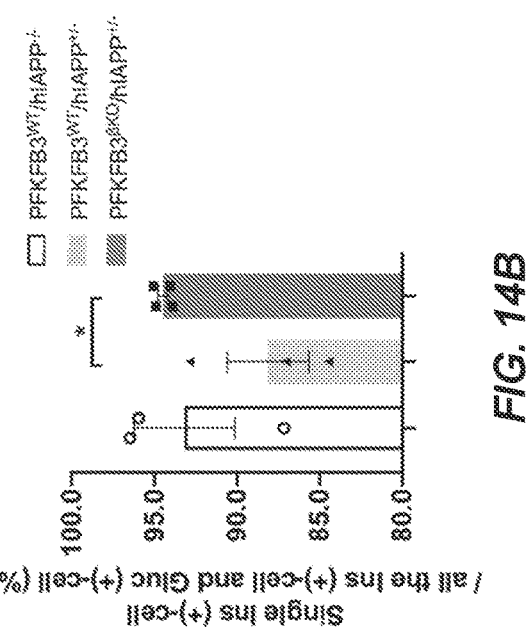
*FIG. 14A*
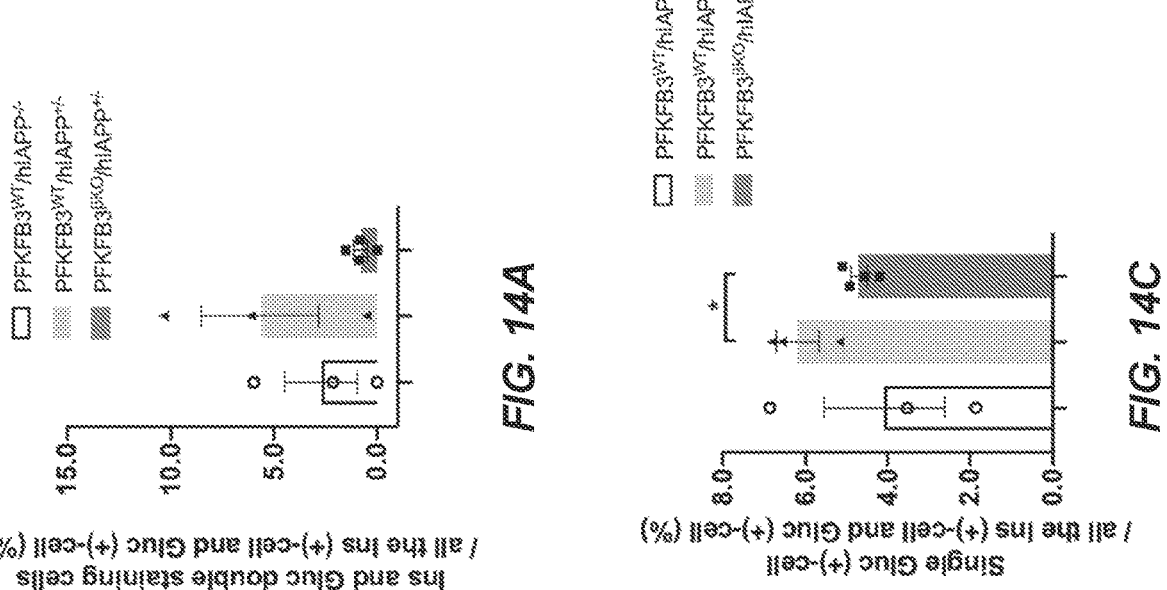
*FIG. 14B*
*FIG. 14C*

Body weight of 1 week before HFD

Body weight of base line

β-cell
cluster differences
in health:

β-cell
cluster differences
in Type-2 diabetes:

LDHA+ vs. LDHA –
β-cell
differences
in health:

LDHA+ vs. LDHA –
β-cell
differences
in Type-2 diabetes:

Cluster 1
β-cell
differences in T2D
versus health .

LDHA-
β-cell
differences in T2D
versus health :

METHODS AND COMPOSITIONS FOR DIABETES TREATMENT AND β-CELL REGENERATION

This application is a national phase application under 35 U.S.C. § 371 of International Application No. PCT/US2021/046267 filed Aug. 17, 2021, which claims benefit of priority of U.S. Provisional Application No. 63/067,187, filed Aug. 18, 2020, and U.S. Provisional Application No. 63/169,776, filed Apr. 1, 2021, all of which are hereby incorporated by reference in their entirety.

SEQUENCE LISTING

The instant application contains a Sequence Listing which has been submitted in ASCII format and is hereby incorporated by reference in its entirety. Said ASCII copy, created on Aug. 16, 2021, is named UCLA_P0116WO_Seq_Listing.txt and is 22,602 bytes in size.

BACKGROUND

I. Field of the Invention

Aspects of this invention relate to at least the fields of molecular biology and medicine.

II. Background

There is a progressive decline in β-cell function in type-2 diabetes (T2D) that is partly related to the accumulation of the toxic oligomers of islet amyloid pancreatic polypeptide (IAPP) [3-5]. Despite well-documented β-cell stress (altered mitochondrial network and activity, $Ca^{2+}$ toxicity, oxidative and DNA damage) [6-9] there is a surprisingly slow rate of β-cell attrition, with preservation of β-cell mass between 35% and 76% even decades after onset of T2D [4]. However, relative preservation of β-cell mass contrasts with an early loss of β-cell glucose responsiveness prior to the onset of T2D. This indicates that, although viable, most β-cells in T2D are dysfunctional.

Upon acute injury, in cells of healthy tissue, hypoxia inducible factor-1-alpha (HIF1α) initiates a sequence of steps that are required for successful tissue repair [10, 11]. First, there is a profound metabolic remodeling that is mediated by the HIF1α target 6-pho sphofructo-2-kinase/fructose-2,6-biphosphatase 3 (PFKFB3), from mitochondrial-dependent oxidative phosphorylation to high flux via aerobic glycolysis, generating ATP irrespective of oxygen availability. Energy diversion to aerobic glycolysis permits DNA repair by an increase in nucleotide synthesis via pentose phosphate pathway [12]. High flux glycolysis also enables the mitochondrial network to adopt the defensive fragmented perinuclear posture, which protects mitochondria from $Ca^{2+}$ toxicity incurred by injury [13]. Second, cells that retain DNA damage are eliminated by apoptosis and those without DNA damage are used to regenerate lost tissue. Tissue regeneration is accomplished either by progenitor stem cell expansion, by replication after dedifferentiation or by trans-differentiation. Third, once tissue regeneration is completed, the injury signals that induced the HIF1α-PFKFB3 pathway abate and the cells readopt their functional metabolic status.

Unlike in healthy tissue, β-cells in humans with T2D remain trapped in the pro-survival phase of the HIF1α injury/repair response with altered metabolism and the mitochondrial network which slow down the rate of cell attrition at the expense of β-cell function [2]. In spite of extensive research it is still not clear why β-cells are unable to undergo successful regeneration. There exists a need for methods and compositions for inducing elimination of damaged cells and regeneration of healthy cells (e.g., β-cells) to improve insulin sensitivity and better treat subjects suffering from diabetes.

SUMMARY

Aspects of the present disclosure provide methods for treatment of diabetes and related conditions, including type 2 diabetes, and compositions useful in such methods. Embodiments of the present disclosure fulfill certain needs by providing methods and compositions for facilitating regeneration of healthy β-cells by inhibition of HIF1α activity, in some cases in combination with inhibition of PFKFB3 activity. Certain aspects are directed to methods for treatment of type 2 diabetes comprising providing a HIF1α inhibitor. Such methods may further comprise administration of a PFKFB3 inhibitor. Also disclosed, in some embodiments, are pharmaceutical compositions comprising a HIF1α inhibitor and a PFKFB3 inhibitor.

Embodiments of the present disclosure include methods for treating a subject for disorders associated with protein misfolding, methods for treating a subject for diabetes, methods for treating a subject for type 2 diabetes, methods for treating a subject for type 1 diabetes, methods for diagnosing type 2 diabetes, methods for determining sensitivity of a subject having type 2 diabetes to HIF1α inhibitor treatment, methods for improving insulin sensitivity, methods for targeting a HIF1α inhibitor to β-cells, methods for determining an expression level of PFKFB3, methods for killing damaged β-cells, methods for stimulating regeneration of healthy β-cells, compositions comprising one or more HIF1α inhibitors, compositions comprising one or more PFKFB3 inhibitors, and compositions comprising a HIF1α inhibitor and a PFKFB3 inhibitor. The disclosed methods can include at least 1, 2, 3, 4, 5, or more of the following steps: providing an effective amount of a HIF1α inhibitor, providing an effective amount of a PFKFB3 inhibitor, diagnosing a subject for type 2 diabetes, diagnosing a subject for type 1 diabetes, identifying a subject as having type 2 diabetes, identifying a subject as being at risk for type 2 diabetes, identifying a subject as having prediabetes, measuring an expression level of PFKFB3 in a subject, measuring an expression level of PFKFB3 in β-cells of a subject, determining a subject to have an increased PFKFB3 expression level in β-cells of the subject, and providing a subject with one or more additional treatments for type 2 diabetes. One or more of the foregoing steps may be excluded from embodiments of the present disclosure. A composition of the present disclosure can include 1, 2, 3, 4, or more of the following: a HIF1α inhibitor, a PFKFB3 inhibitor, a targeting molecule, a GLP-1 receptor antibody, metformin, a GLP-1 receptor agonist, a DPP-4 inhibitor, sulfonylurea, and one or more pharmaceutically acceptable excipients. One or more of the foregoing components may be excluded from embodiments of the present disclosure.

Disclosed herein, in some embodiments, is a method of treating a subject for type 2 diabetes, the method comprising administering an effective amount of a HIF1α inhibitor to the subject. Also disclosed herein, in some embodiments, is a method of treating a subject for type 2 diabetes comprising administering an effective amount of a HIF1α inhibitor to a subject determined to have an increased expression level of PFKFB3 in β-cells from the subject relative to an expression level of PFKFB3 in β-cells from a healthy subject who is not suffering from type 2 diabetes. In some embodiments, disclosed is a method of treating a subject for type 2 diabetes, the method comprising (a) determining a subject to have an expression level of PFKFB3 in β-cells from the subject relative to an expression level of PFKFB3 in β-cells from a healthy subject who is not suffering from type 2 diabetes; and (b) administering an effective amount of a HIF1α inhibitor to the subject. In some embodiments, disclosed is a method of stimulating regeneration of healthy β-cells in a subject with type 2 diabetes, where the healthy β-cells do not express PFKFB3, the method comprising administering an effective amount of a HIF1α inhibitor to the subject.

In some embodiments, the HIF1α inhibitor promotes HIF1α degradation. In some embodiments, the HIF1α inhibitor inhibits HIF1α/HIF1β dimer formation. In some embodiments, the HIF1α inhibitor reduces HIF1α transcriptional activity. In some embodiments, the HIF1α inhibitor is KC7F2, IDF-11774, aminoflavone, AJM290, AW464, tanespimycin, alvespimycin, PX-478, or FM19G11. In some embodiments, the HIF1α inhibitor is a nucleic acid inhibitor. In some embodiments, the HIF1α inhibitor is an antisense oligonucleotide. In some embodiments, the HIF1α inhibitor is EZN-2698. In some embodiments, the HIF1α inhibitor is an siRNA or a short hairpin RNA. In some embodiments, the HIF1α inhibitor is resveratrol, rapamycin, everolimus, CCI779, silibinin, digoxin, YC-1, phenethyl isothiocyanite, chetomin, flavopiridol, bortezomib, amphotericin B, Bay 87-2243, PX-478, or ganetasipib. In some embodiments, the HIF1α inhibitor is an anti-HIF1α antibody or antibody-like molecule. In some embodiments, the HIF1α inhibitor is a nanobody. In some embodiments, the HIF1α inhibitor is administered intravenously, intramuscularly, intraperitoneally, subcutaneously, intra-articularly, intrasynovially, intrathecally, orally, topically, through inhalation, or through a combination of two or more routes of administration.

In some embodiments, the method further comprises administering a PFKFB3 inhibitor to the subject. In some embodiments, the PFKFB3 inhibitor is 3-(3-Pyridinyl)-1-(4-pyridinyl)-2-propen-1-one (3-PO) or an analog thereof. In some embodiments, the PFKFB3 inhibitor is an analog of 3-PO, wherein the analog is 1-(4-pyridinyl)-3-(2-quinolinyl)-2-propen-1-one (PFK 15). In some embodiments, the PFKFB3 inhibitor is BrAcNHEtOP, YN1, YZ9, PQP, PFK-158, Compound 26, KAN0436151, or KAN0436067. In some embodiments, the PFKFB3 inhibitor is a nucleic acid inhibitor. In some embodiments, the PFKFB3 inhibitor is an antisense oligonucleotide. In some embodiments, the PFKFB3 inhibitor is an siRNA or a short hairpin RNA. In some embodiments, the PFKFB3 inhibitor is operatively linked to a targeting molecule configured to bind to β-cells of the subject. In some embodiments, the HIF1α inhibitor is operatively linked to a targeting molecule configured to bind to β-cells of the subject. In some embodiments, the targeting molecule is an antibody. In some embodiments, the targeting molecule is an antibody-like molecule. In some embodiments, the targeting molecule is configured to bind to a GLP-1 receptor. In some embodiments, the HIF1α a inhibitor and the PFKFB3 inhibitor are administered to the subject sequentially. In some embodiments, the HIF1α inhibitor and the PFKFB3 inhibitor are administered to the subject substantially simultaneously.

In some embodiments, administering the effective amount of the HIF1α inhibitor increases insulin sensitivity in the subject. In some embodiments, the subject does not have or has not been diagnosed with cancer. In some embodiments, the subject has been diagnosed with type 2 diabetes. In some embodiments, the method further comprises, prior to the administering, diagnosing the subject with the type 2 diabetes. In some embodiments, the subject was previously treated for type 2 diabetes. In some embodiments, the subject was determined to be resistant to the previous treatment. In some embodiments, the subject does not have or has not been diagnosed with diabetic nephropathy or diabetic retinopathy. In some embodiments, the method further comprises measuring an expression level of PFKFB3 in β-cells from the subject. In some embodiments, the expression level of PFKFB3 in the β-cells from the subject is increased relative to an expression level of PFKFB3 in β-cells from a healthy subject who is not suffering from type 2 diabetes.

Embodiments of the disclose also include a method of increasing insulin sensitivity in a subject, the method comprising administering an effective amount of a HIF1α inhibitor to the subject. In some embodiments, the subject suffers from prediabetes. In some embodiments, the subject suffers from insulin resistance. Also disclosed, in some embodiments, is a method for stimulating cell death in damaged β-cells expressing PFKFB3, the method comprising providing a HIF1α inhibitor to the β-cells. In some embodiments, disclosed is a method for stimulating regeneration in β-cells that do not express PFKFB3, the method comprising providing a HIF1α inhibitor to the β-cells. In some embodiments, the HIF1α inhibitor is provided to the β-cells in vitro. In some embodiments, the HIF1α inhibitor is provided to the β-cells in vivo.

In certain aspects, disclosed herein is a method for killing PFKFB3-expressing damaged β-cells in a subject with diabetes, the method comprising administering an effective amount of a HIF1α inhibitor to the subject. Also disclosed, in some embodiments, is a method of treating a subject for diabetes, the method comprising administering an effective amount of a HIF1α inhibitor to the subject. In some embodiments, the diabetes is type 1 diabetes. In some embodiments, the diabetes is type 2 diabetes.

Certain embodiments are directed to methods for diagnosis of a disease or disorder. In some embodiments, disclosed is a method for diagnosing a subject for type 2 diabetes, the method comprising: (a) measuring an expression level of PFKFB3 in β-cells from the subject; (b) comparing the expression level to an expression level of PFKFB3 in β-cells from a healthy subject who is not suffering from type 2 diabetes; and (c) determining the expression level of PFKFB3 in β-cells from the subject to be increased relative to the expression level of PFKFB3 in β-cells from the healthy subject, thereby diagnosing the subject for type 2 diabetes.

Further disclosed herein, in some embodiments, are various pharmaceutical compositions. In some embodiments, disclosed is a pharmaceutical composition comprising (a) a HIF1α inhibitor and (b) a PFKFB3 inhibitor. The HIF1α inhibitor may be any HIF1α inhibitor, examples of which are disclosed herein. The PFKFB3 inhibitor may be any PFKFB3 inhibitor, examples of which are disclosed herein.

Also disclosed, in some embodiments, is a method of eliminating bihormonal cells from a population of cells, the method comprising administering an effective amount of a PFKFB3 inhibitor to the population of cells. In some embodiments, the PFKFB3 inhibitor is administered to the population of cells in vitro. In some embodiments, the PFKFB3 inhibitor is administered to the population of cells in vivo. The PFKFB3 inhibitor may be any PFKFB3 inhibitor, examples of which are disclosed herein. Further disclosed, in some embodiments, is a method of eliminating bihormonal cells from a population of cells, the method comprising administering an effective amount of a HIF1α inhibitor to the population of cells. The HIF1α inhibitor may be any HIF1α inhibitor, examples of which are disclosed herein. some embodiments, the HIF1α inhibitor is administered to the population of cells in vitro. In some embodiments, the HIF1α inhibitor is administered to the population of cells in vivo. In some embodiments, the population of cells is a population of pancreatic islet cells. In some embodiments, the population of cells is a population of differentiated stem cells. In some embodiments, the differentiated stem cells are differentiated induced pluripotent stem cells (iPSCs). In some embodiments, the differentiated stem cells are embryonic stem cells (ESCs).

Throughout this application, the term "about" is used to indicate that a value includes the inherent variation of error for the measurement or quantitation method.

The use of the word "a" or "an" when used in conjunction with the term "comprising" may mean "one," but it is also consistent with the meaning of "one or more," "at least one," and "one or more than one."

The phrase "and/or" means "and" or "or". To illustrate, A, B, and/or C includes: A alone, B alone, C alone, a combination of A and B, a combination of A and C, a combination of B and C, or a combination of A, B, and C. In other words, "and/or" operates as an inclusive or.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. Compositions and methods "consisting essentially of" any of the ingredients or steps disclosed limits the scope of the claim to the specified materials or steps which do not materially affect the basic and novel characteristic of the claimed invention. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that embodiments described herein in the context of the term "comprising" may also be implemented in the context of the term "consisting of" or "consisting essentially of."

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary, Detailed Description, Claims, and Brief Description of the Drawings.

Any method in the context of a therapeutic, diagnostic, or physiologic purpose or effect may also be described in "use" claim language such as "Use of" any compound, composition, or agent discussed herein for achieving or implementing a described therapeutic, diagnostic, or physiologic purpose or effect.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1D show results demonstrating that β-cells in T2D patients and rodent models of diabetes (hIAPP transgenic rat (HIP) and mouse (hTG)) show reduced cellular fitness. FIG. 1A shows confocal images of islet-cells in T2D versus no disease (ND) immunostained for mitochondria marker Tom20, indicating reduced mitochondrial area and perinuclear distribution of fragmented mitochondria in islets from T2D donors. FIG. 1B shows oxygen consumption rate (OCR) presented as a -fold of basal respiration as measured by Seahorse, demonstrating decline in isolated islets from 4.5 months old HIP compared to WT rats after stimulation with high glucose (16.7 mM). FIG. 1C shows cytosolic Ca2+ as measured with FURA2 AM, demonstrating an increase in the islets from hIAPP (hTG) compared to control rodent IAPP (rTG) transgenic mice. FIG. 1D shows immunoblotting analysis of the whole cell extracts (WCE) and nuclear fractions from 3 human non-diabetic (ND) and 3 T2D donor islets, revealing an increase in PFKFB3 and HIF1α concomitant with an increase in markers of injury: tumor suppressor p53, p21WAF1 and γH2A.X (marker of genotoxic stress).

FIG. 2A shows immunofluorescence images of islets (nPOD collection) from non-diabetic (ND) and T2D subjects immunostained for PFKFB3, insulin, and nuclei. FIG. 2B shows a schematic of PFKFB3 controlling $Ca^{2+}$ homeostasis, mitochondria and metabolome in stressed β-cells. FIGS. 2C and 2D show quantification of cell death by TUNEL positive INS 832/13 cells after HIF1α inhibition (FIG. 2C) or PFKFB3 siRNA silencing (FIG. 2D) in presence or absence of hIAPP expression.

FIG. 3A shows the experimental timeline. FIG. 3B shows immunofluorescence images of islets from PFKFB3$^{WT}$ and PFKFB3$^{βKO}$ on hIAPP+/− background and on a high fat diet (HFD) immunostained for PFKFB3 (red), insulin (green) and nuclei (blue). PFKFB3$^{WT}$ hIAPP$^{+/+}$ was used as a positive control.

FIG. 4A shows fasting blood glucose. FIG. 4B shows intraperitoneal glucose tolerance test (IP-GTT) results. FIG. 4C Plasma C-peptide and glucagon measured at the end of the experimental protocol and FIG. 4D Insulin tolerance test (ITT).

FIG. 5A shows representative immunofluorescence images of islets from PFKFB3$^{WT}$ and PFKFB3$^{\beta KO-}$ mice on hIAPP+/- or hIAPP-/- background and on a high fat diet (HFD) immunostained for MCM2, insulin, and nuclei. FIG. 5B shows fractional β-cell area. FIG. 5C shows β-/α-cell ratio. FIG. 5D shows β-cell death measured by TUNEL assay. FIG. 5E shows β-cell replication as measured by minichromosome maintenance protein 2 (MCM2) immunostaining and quantification (n=4, SEM *p<0.05).

FIG. 6A shows representative immunofluorescence images of islets from PFKFB3$^{WT}$ and PFKFB3$^{\beta KO-}$ mice on hIAPP+/- or hIAPP-/- background and on a high fat diet (HFD) immunostained for HIF1α, insulin, and nuclei. FIG. 6B shows quantification of HIF1α-positive β-cells after immunostaining with specific antibodies. FIG. 6C shows quantification of c-Myc-positive β-cells after immunostaining with specific antibodies (n=4, SEM *p<0.05).

FIGS. 7A and 7B show results demonstrating that LDHA positive β-cell subpopulation is enriched of insulin secretion associated genes in T2D. FIG. 7A shows UMAP clustering of β-cells from published RNA-Seq data [1] identifies cluster 7 subpopulation that overlaps with LDHA positive β-cells. FIG. 7B shows a table of differentially expressed genes that are either upregulated (UP) or downregulated (DOWN) in cluster 7 versus 1 and LDHA positive-versus negative β-cells.

FIG. 8A shows representative immunofluorescence images of islets from PFKFB3$^{WT}$ and PFKFB3$^{\beta KO}$ on hIAPP+/- background and on a high fat diet (HFD) immunostained for PFKFB3 (red), insulin (green) and nuclei (blue) FIG. 8B shows quantification of images in FIG. 8A. FIG. 8C shows representative immunofluorescence images of islets from PFKFB3$^{WT}$ and PFKFB3$^{\beta KO-}$ mice on hIAPP+/- or hIAPP-/- background and on a high fat diet (HFD) immunostained for HIF1α, insulin and nuclei. FIG. 8D shows quantification of images in FIG. 8A (n=3, n=4 for PFKFB3$^{\beta KO}$ hIAPP+/-, SEM *p<0.05).

FIGS. 9A-9I show results demonstrating that PFKFB3$^{\beta KO}$ IAPP$^{+/-}$ mice under high fat diet (HFD) demonstrate increased impaired glucose tolerance and similar insulin—but reduced glucagon plasma levels relative to PFKFB3$^{WT}$ IAPP$^{+/-}$ mice. FIG. 9A shows results from an intra-peritoneal glucose tolerance test (IP-GTT) at 9 weeks post onset of high fat diet (HFD). FIG. 9B shows quantification of the area under the curve (AUC) as mg/dL×min in the experimental groups in FIG. 9A. FIG. 9C shows results from an intra-peritoneal glucose tolerance test (IP-GTT) at 12 weeks post onset of HFD. FIG. 9D shows quantification of the area under the curve (AUC) as mg/dL×min in the experimental groups in FIG. 9C. FIG. 9E shows results from an insulin tolerance test at 9 weeks after onset of HFD FIG.

9F shows quantification of the area under the curve (AUC) as mg/dL×min in the experimental groups in FIG. 9E. FIGS. 9G and 9H show fasting plasma insulin (FIG. 9G) and C-peptide (FIG. 9H) presented relative to β-cell mass (12 weeks post onset of HFD). FIG. 9I shows fasting plasma glucagon (12 weeks post onset of HFD) (n=3, n=4 for PFKFB3$^{\beta KO}$ hIAPP+/-, SEM *p<0.05).

FIG. 10A shows quantification of fractional β-cell area (%) FIG. 10B shows quantification of β-cell mass (mg). FIG. 10C shows quantification of β-cell death as measured by labelling with TUNEL assay (%) represented relative to fractional β-cell area. FIG. 10D shows quantification of β-cell relative to a-cell number in indicated experimental groups. FIG. 10E shows representative immunofluorescence images of islets from PFKFB3$^{WT}$ and PFKFB3$^{\beta KO-}$ mice on hIAPP+/- or hIAPP-/- background and on a high fat diet (HFD) immunostained for cleaved caspase-3, insulin and nuclei. FIG. 10F shows quantification of images from FIG. 10E. (n=3, n=4 for PFKFB3$^{\beta KO}$ hIAPP+/-, SEM *p<0.05).

FIG. 11A shows representative immunofluorescence images of islets from PFKFB3$^{WT}$ and PFKFB3$^{\beta KO-}$ mice on hIAPP+/- or hIAPP-/- background and on a high fat diet (HFD) immunostained for MCM2, insulin and nuclei. FIG. 11B shows quantification of images under FIG. 11A. FIG. 11C shows representative immunofluorescence images of islets from PFKFB3$^{WT}$ and PFKFB3$^{\beta KO-}$ mice on hIAPP+/- or hIAPP-/- background and on a high fat diet (HFD) immunostained for c-Myc, insulin and nuclei. FIG. 11D shows quantification of cytoplasmic c-Myc (Myc-nick) indicating cells undergoing hIAPP-induced calpain activation (damage) as revealed by immunostaining in FIG. 11C (n=3, n=4 for PFKFB3$^{\beta KO}$ hIAPP+/-, SEM *p<0.05).

FIG. 12A shows UMAP-2 cluster distribution of pancreatic cells from healthy and T2D donors. FIG. 12B shows UMAP-2 distribution of α-cells (alpha), β-cells (beta), cells with low counts, cells with uncertain identity, acinar cells and ductal cells based on the identity markers. FIG. 12C shows UMAP-2 distribution of pancreatic cells in 9 pancreatic subpopulations based on the expression levels of the identity markers. FIG. 12D shows UMAP-2 distribution of lactate dehydrogenase positive and negative pancreatic cells (LDHA, HIF1α target indicating HIF1α signature).

FIGS. 14A-14E show results demonstrating that PFKFB3$^{\beta KO}$ IAPP$^{+/-}$ mice show decrease of double positive insulin+/glucagon+ cells. FIG. 14A shows quantification of the ratio between single insulin positive β-cells relative to all single positive β- and α-cells (%). FIG. 14B shows quantification of the ratio between single glucagon positive α-cells relative to all single positive β- and α-cells (%). FIG. 14C shows quantification of the ratio between double insulin (INS+) and glucagon (GCG+) positive cells relative to all single insulin or glucagon positive β- and α-cells, respectively (%). FIG. 14D shows cell composition of single insulin positive β-cells, single glucagon positive α-cells and double insulin and glucagon positive cells in indicated experimental groups. WT, homozygous (hom) hIAPP$^{+/+}$ mice without HFD with prediabetes (pre-DM) and diabetes (DM) (WT, hom TG-preDM and hom TG-DM) were used for comparison to the study experimental groups (n=3, n=4 for PFKFB3$^{βKO}$ hIAPP+/−, SEM *p<0.05). FIG. 14E shows cell composition of single insulin positive β-cells, single glucagon positive α-cells and double insulin positive and glucagon positive cells in indicated experimental groups (n=3, n=4 for PFKFB3$^{βKO}$ DS, SEM *p<0.05).

DETAILED DESCRIPTION

Figures 2A, 2B:
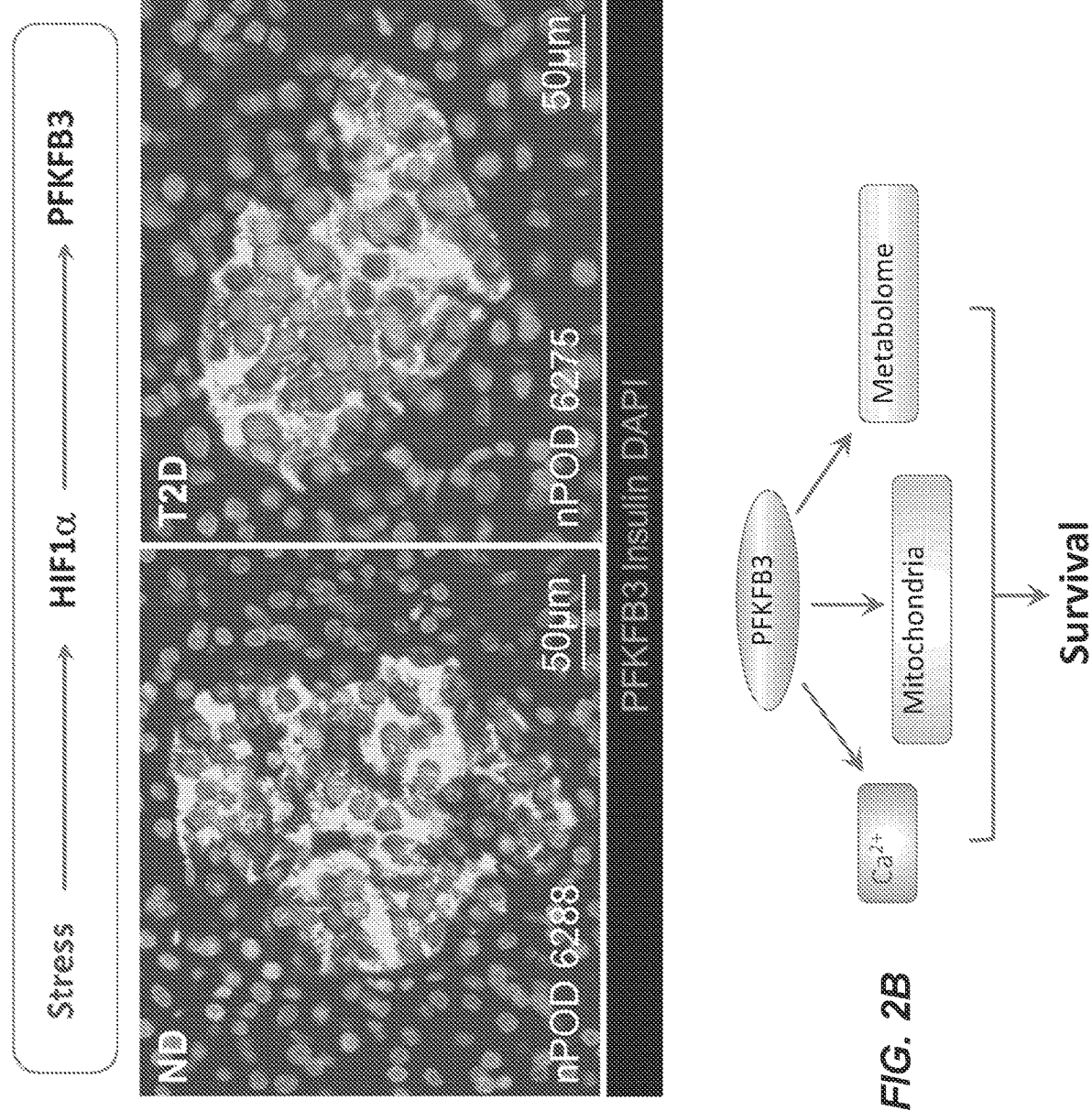
FIGS. 2A-2D show results demonstrating that β-cells in humans with T2D show metabolic remodelling by the pro-survival HIF1α-PFKFB3 pathway.

The present disclosure is based, at least in part, on the identification of β-cell dysfunction in T2D as resulting from a failure of affected β-cells to undergo purifying selection by cell competition with remaining healthy β-cells due to activation of the HIF1α-PFKFB3 injury/repair response. Without wishing to be bound by theory, it is believed that injured β-cells with remodeled metabolism become entrapped via high glycolysis disengaged from the TCA cycle that renders β-cells non-responsive to glucose and that chronic activation of the HIF1α-PFKFB3 pathway prevents homeostatic cell competition necessary for purging damaged β-cells. Given that the survival of injured β-cells in T2D depends on the HIF1α-PFKFB3 pathway, it is believed that that the HIF1α-PFKFB3 injury/repair pathway helps injured β-cells to escape selection by cell competition and that inhibited cell competition by remodeled metabolism impedes β-cell regeneration. Disclosed herein, in some embodiments, are methods and compositions for facilitating β-cell regeneration by inhibition of the HIF1α-PFKFB3 pathway, including HIF1α inhibition, PFKFB3 inhibition, and the combination thereof. Aspects of the disclosure address various needs in the art by providing for treatment of subjects suffering from diabetes, including type-1 diabetes and type-2 diabetes.

I. Therapeutic Methods

Aspects of the present disclosure are directed to methods and compositions for treatment of certain diseases and disorders. In some embodiments, disclosed are methods for treatment of subjects having disorders associated with (e.g., characterized by) protein misfolding. In some embodiments, disorders associated with protein misfolding include diabetes and associated conditions (e.g., prediabetes, type 1 diabetes, type 2 diabetes). Although often described with regards to the treatment or prevention of type 2 diabetes, it is understood that the disclosed methods and compositions may also be used for treating or preventing other disorders associated with protein misfolding, including type 1 diabetes and prediabetes.

In some embodiments, disclosed herein is a method for treating a subject for type 2 diabetes (T2D) and/or preventing a subject from developing T2D, the method comprising providing one or more agents capable of inhibiting the HIF1α-PFKFB3 pathway in cells of the subject. In some embodiments, a subject has been diagnosed for T2D. In some embodiments, a subject is at risk for developing T2D. In some embodiments, a subject has prediabetes. In some embodiments, a subject has T2D subtype 1, subtype 2, or subtype 3. T2D subtypes are known in the art and described in, for example, Li L, Cheng W Y, Glicksberg B S, et al. *Sci Transl Med.* 2015; 7(311):311ra174, incorporated herein by reference in its entirety. In some embodiments, a subject has T2D subtype 1. In some embodiments, a subject has T2D subtype 2. In some embodiments, a subject has T2D subtype 3. In some embodiments, a subject does not have T2D subtype 1. In some embodiments, a subject does not have T2D subtype 2. In some embodiments, a subject does not have T2D subtype 3.

As recognized herein, inhibition of the HIF1α-PFKFB3 pathway enhances killing of unhealthy β-cells and contributes to regeneration of healthy β-cells in T2D. In some embodiments, unhealthy β-cells describe β-cells expressing PFKFB3 (e.g., having a level of expression of PFKFB3 higher than β-cells from a subject that does not have T2D). In some embodiments, healthy β-cells describe β-cells that do not express PFKFB3 or have an expression level of PFKFB3 that is not significantly different from β-cells from a subject that does not have T2D. Treating a subject for T2D may comprise improving symptoms of T2D in the subject, for example increasing insulin sensitivity in the subject.

Methods for treating a subject for T2D may comprise providing an effective amount of a HIF1α inhibitor. In some embodiments, providing a HIF1α inhibitor reduces PFKFB3 levels in β-cells of the subject. Methods for treating a subject for T2D may comprise providing an effective amount of a PFKFB3 inhibitor. In some embodiments, the disclosed methods comprise providing both a HIF1α inhibitor and a PFKFB3 inhibitor to a subject. The HIF1α inhibitor and the PFKFB3 inhibitor may be administered sequentially or substantially simultaneously. The HIF1α inhibitor and the PFKFB3 inhibitor may be provided in the same composition or provided in separate compositions.

In some embodiments, a subject treated as described herein does not have cancer or has not been diagnosed with cancer. In some embodiments, a subject treated as described herein does not have or has not been diagnosed with diabetic nephropathy or diabetic retinopathy.

Aspects of the disclosed methods comprise, in further embodiments, measuring an expression level of PFKFB3 in a subject. In some embodiments, a PFKFB3 expression level is measured in β-cells from a subject. In some embodiments, a PFKFB3 expression level is used to identify a subject as having T2D. In some embodiments, a PFKFB3 expression level is used to determine whether a subject will be sensitive to a treatment comprising a HIF1α and/or PFKFB3 inhibitior. In some embodiments, β-cells from a subject are determined to have a PFKFB3 expression level that is increased relative to a healthy or control subject. In some embodiments, a healthy subject is a subject who does not have diabetes or prediabetes. In some embodiments, a healthy subject is a subject who does not have T2D. In some embodiments, β-cells from a subject are determined to have a PFKFB3 expression level that is increased relative to control cells from the subject.

In some embodiments, a subject is treated with a HIF1α inhibitor and/or a PFKFB3 inhibitor together with one or more additional therapies, e.g., type 2 diabetes therapies. In some embodiments, a subject is treated with a HIF1α inhibitor and/or a PFKFB3 inhibitor together with a GLP-1 receptor agonist. In some embodiments, a subject is treated with a HIF1α inhibitor and/or a PFKFB3 inhibitor together with metformin. In some embodiments, a subject is treated with a HIF1α inhibitor and/or a PFKFB3 inhibitor together with insulin. In some embodiments, a subject is treated with a HIF1α inhibitor and/or a PFKFB3 inhibitor together with a DPP-4 inhibitor.

II. HIF1α

Hypoxia inducible factor 1-alpha (HIF1α; also HIF1A) is a transcription factor involved in transcriptional regulation of various genes, including those involved in adaptive response to hypoxia.

The following sequence exemplifies the HIF1α mRNA in humans (SEQ ID NO: 1):

```
AGTGCACAGTGCTGCCTCGTCTGAGGGGACAGGAGGATCACCCT

CTTCGTCGCTTCGGCCAGTGTGTCGGGCTGGGCCCTGACAAGCC
```

```
ACCTGAGGAGAGGCTCGGAGCCGGGCCCGGACCCCGGCGATTGC

CGCCCGCTTCTCTCTAGTCTCACGAGGGGTTTCCCGCCTCGCAC

CCCCACCTCTGGACTTGCCTTTCCTTCTCTTCTCCGCGTGTGGA

GGGAGCCAGCGCTTAGGCCGGAGCGAGCCTGGGGGCCGCCCGCC

GTGAAGACATCGCGGGGACCGATTCACCATGGAGGGCGCCGGCG

GCGCGAACGACAAGAAAAAGATAAGTTCTGAACGTCGAAAGAA

AAGTCTCGAGATGCAGCCAGATCTCGGCGAAGTAAAGAATCTGA

AGTTTTTTATGAGCTTGCTCATCAGTTGCCACTTCCACATAATG

TGAGTTCGCATCTTGATAAGGCCTCTGTGATGAGGCTTACCATC

AGCTATTTGCGTGTGAGGAAACTTCTGGATGCTGGTGATTTGGA

TATTGAAGATGACATGAAAGCACAGATGAATTGCTTTTATTTGA

AAGCCTTGGATGGTTTTGTTATGGTTCTCACAGATGATGGTGAC

ATGATTTACATTTCTGATAATGTGAACAAATACATGGGATTAAC

TCAGTTTGAACTAACTGGACACAGTGTGTTTGATTTTACTCATC

CATGTGACCATGAGGAAATGAGAGAAATGCTTACACACAGAAAT

GGCCTTGTGAAAAAGGGTAAAGAACAAAACACACAGCGAAGCTT

TTTTCTCAGAATGAAGTGTACCCTAACTAGCCGAGGAAGAACTA

TGAACATAAAGTCTGCAACATGGAAGGTATTGCACTGCACAGGC

CACATTCACGTATATGATACCAACAGTAACCAACCTCAGTGTGG

GTATAAGAAACCACCTATGACCTGCTTGGTGCTGATTTGTGAAC

CCATTCCTCACCCATCAAATATTGAAATTCCTTTAGATAGCAAG

ACTTTCCTCAGTCGACACAGCCTGGATATGAAATTTTCTTATTG

TGATGAAAGAATTACCGAATTGATGGGATATGAGCCAGAAGAAC

TTTTAGGCCGCTCAATTTATGAATATTATCATGCTTTGGACTCT

GATCATCTGACCAAAACTCATCATGATATGTTTACTAAAGGACA

AGTCACCACAGGACAGTACAGGATGCTTGCCAAAAGAGGTGGAT

ATGTCTGGGTTGAAACTCAAGCAACTGTCATATATAACACCAAG

AATTCTCAACCACAGTGCATTGTATGTGTGAATTACGTTGTGAG

TGGTATTATTCAGCACGACTTGATTTTCTCCCTTCAACAAACAG

AATGTGTCCTTAAACCGGTTGAATCTTCAGATATGAAAATGACT

CAGCTATTCACCAAAGTTGAATCAGAAGATACAAGTAGCCTCTT

TGACAAACTTAAGAAGGAACCTGATGCTTTAACTTTGCTGGCCC

CAGCCGCTGGAGACACAATCATATCTTTAGATTTTGGCAGCAAC

GACACAGAAACTGATGACCAGCAACTTGAGGAAGTACCATTATA

TAATGATGTAATGCTCCCCTCACCCAACGAAAAATTACAGAATA

TAAATTTGGCAATGTCTCCATTACCCACCGCTGAAACGCCAAAG

CCACTTCGAAGTAGTGCTGACCCTGCACTCAATCAAGAAGTTGC

ATTAAAATTAGAACCAAATCCAGAGTCACTGGAACTTTCTTTTA

CCATGCCCCAGATTCAGGATCAGACACCTAGTCCTTCCGATGGA

AGCACTAGACAAAGTTCACCTGAGCCTAATAGTCCCAGTGAATA
```

-continued

```
TTGTTTTTATGTGGATAGTGATATGGTCAATGAATTCAAGTTGG

AATTGGTAGAAAAACTTTTTGCTGAAGCACAGAAGCAAAGAAC

CCATTTTCTACTCAGGACACAGATTTAGACTTGGAGATGTTAGC

TCCCTATATCCCAATGGATGATGACTTCCAGTTACGTTCCTTCG

ATCAGTTGTCACCATTAGAAAGCAGTTCCGCAAGCCCTGAAAGC

GCAAGTCCTCAAAGCACAGTTACAGTATTCCAGCAGACTCAAAT

ACAAGAACCTACTGCTAATGCCACCACTACCACTGCCACCACTG

ATGAATTAAAAACAGTGACAAAAGACCGTATGGAAGACATTAAA

ATATTGATTGCATCTCCATCTCCTACCCACATACATAAAGAAAC

TACTAGTGCCACATCATCACCATATAGAGATACTCAAAGTCGGA

CAGCCTCACCAAACAGAGCAGGAAAAGGAGTCATAGAACAGACA

GAAAAATCTCATCCAAGAAGCCCTAACGTGTTATCTGTCGCTTT

GAGTCAAAGAACTACAGTTCCTGAGGAAGAACTAAATCCAAAGA

TACTAGCTTTGCAGAATGCTCAGAGAAAGCGAAAAATGGAACAT

GATGGTTCACTTTTTCAAGCAGTAGGAATTGGAACATTATTACA

GCAGCCAGACGATCATGCAGCTACTACATCACTTTCTTGGAAAC

GTGTAAAAGGATGCAAATCTAGTGAACAGAATGGAATGGAGCAA

AAGACAATTATTTTAATACCCTCTGATTTAGCATGTAGACTGCT

GGGGCAATCAATGGATGAAAGTGGATTACCACAGCTGACCAGTT

ATGATTGTGAAGTTAATGCTCCTATACAAGGCAGCAGAAACCTA

CTGCAGGGTGAAGAATTACTCAGAGCTTTGGATCAAGTTAACTG

AGCTTTTTCTTAATTTCATTCCTTTTTTTTGGACACTGGTGGCTC

ATTACCTAAAGCAGTCTATTTATATTTTCTACATCTAATTTTAG

AAGCCTGGCTACAATACTGCACAAACTTGGTTAGTTCAATTTTG

ATCCCCTTTCTACTTAATTTACATTAATGCTCTTTTTTAGTATG

TTCTTTAATGCTGGATCACAGACAGCTCATTTTCTCAGTTTTTT

GGTATTTAAACCATTGCATTGCAGTAGCATCATTTTAAAAAATG

CACCTTTTTATTTATTTATTTTTGGCTAGGGAGTTTATCCCTTT

TTCGAATTATTTTTAAGAAGATGCCAATATAATTTTTGTAAGAA

GGCAGTAACCTTTCATCATGATCATAGGCAGTTGAAAAATTTTT

ACACCTTTTTTTTCACATTTTACATAAATAATAATGCTTTGCCA

GCAGTACGTGGTAGCCACAATTGCACAATATATTTTCTTAAAAA

ATACCAGCAGTTACTCATGGAATATATTCTGCGTTTATAAAACT

AGTTTTTAAGAAGAAATTTTTTTTGGCCTATGAAATTGTTAAAC

CTGGAACATGACATTGTTAATCATATAATAATGATTCTTAAATG

CTGTATGGTTTATTATTTAAATGGGTAAAGCCATTTACATAATA

TAGAAAGATATGCATATATCTAGAAGGTATGTGGCATTTATTTG

GATAAAATTCTCAATTCAGAGAAATCATCTGATGTTTCTATAGT

CACTTTGCCAGCTCAAAAGAAAACAATACCCTATGTAGTIGTGG

AAGTTTATGCTAATATTGTGTAACTGATATTAAACCTAAATGTT

CTGCCTACCCTGTTGGTATAAAGATATTTTGAGCAGACTGTAAA
```

-continued

```
CAAGAAAAAAAAAATCATGCATTCTTAGCAAAATTGCCTAGTAT

GTTAATTTGCTCAAAATACAATGTTTGATTTTATGCACTTTGTC

GCTATTAACATCCTTTTTTTCATGTAGATTTCAATAATTGAGTA

ATTTTAGAAGCATTATTTTAGGAATATATAGTTGTCACAGTAAA

TATCTTGTTTTTTCTATGTACATTGTACAAATTTTTCATTCCTT

TTGCTCTTTGTGGTTGGATCTAACACTAACTGTATTGTTTTGTT

ACATCAAATAAACATCTTCTGTGGACCAGG
```

The protein sequence is exemplified by the following (SEQ ID NO:2):

```
MEGAGGANDKKKISSERRKEKSRDAARSRRSKESEVFYELAHQL

PLPHNVSSHLDKASVMRLTISYLRVRKLLDAGDLDIEDDMKAQM

NCFYLKALDGFVMVLTDDGDMIYISDNVNKYMGLTQFELTGHSV

FDFTHPCDHEEMREMLTHRNGLVKKGKEQNTQRSFFLRMKCTLT

SRGRTMNIKSATWKVLHCTGHIHVYDTNSNQPQCGYKKPPMTCL

VLICEPIPHPSNIEIPLDSKTFLSRHSLDMKFSYCDERITELMG

YEPEELLGRSIYEYYHALDSDHLTKTHHDMFTKGQVTTGQYRML

AKRGGYVWVETQATVIYNTKNSQPQCIVCVNYVVSGIIQHDLIF

SLQQTECVLKPVESSDMKMTQLFTKVESEDTSSLFDKLKKEPDA

LTLLAPAAGDTIISLDFGSNDTETDDQQLEEVPLYNDVMLPSPN

EKLQNINLAMSPLPTAETPKPLRSSADPALNQEVALKLEPNPES

LELSFTMPQIQDQTPSPSDGSTRQSSPEPNSPSEYCFYVDSDMV

NEFKLELVEKLFAEDTEAKNPFSTQDTDLDLEMLAPYIPMDDDF

QLRSFDQLSPLESSSASPESASPQSTVTVFQQTQIQEPTANATT

TTATTDELKTVTKDRMEDIKILIASPSPTHIHKETTSATSSPYR

DTQSRTASPNRAGKGVIEQTEKSHPRSPNVLSVALSQRTTVPEE

ELNPKILALQNAQRKRKMEHDGSLFQAVGIGTLLQQPDDHAATT

SLSWKRVKGCKSSEQNGMEQKTIILIPSDLACRLLGQSMDESGL

PQLTSYDCEVNAPIQGSRNLLQGEELLRALDQVN
```

A. HIF1α Inhibitors

A HIF1α inhibitor may refer to any member of the class of compound or agents having an IC$_{50}$ of 200 μM or lower concentration for a HIF1α activity, for example, at least or at most or about 200, 100, 80, 50, 40, 20, 10, 5, 1 μM, 100, 10, 1 nM or lower concentration (or any range or value derivable therefrom). A HIF1α inhibitor may refer to any compound or agent that inhibits the expression of HIF1α. Examples of inhibitors HIF1α activity or function may include, but are not limited to, agents that prevent HIF1α/HIF1β dimerization, agents that reduce or eliminate protein expression, agents that promote HIF1α degradation (e.g., proteosomal degradation), agents that prevent HIF1α from interacting with DNA, and agents that inhibit HIF1α transcriptional activity. In some embodiments, a HIF1α inhibitor is an agent that binds directly to HIF1α. In some embodiments, a HIF1α inhibitor does not bind directly to HIF1α. Example HIF1α inhibitors are described in, for example, Onnis et al., J. Cell. Mol. Med. 2009 13(9a):

2780-2786, incorporated herein by reference in its entirety. Methods and compositions of the disclosure may comprise one or more HIF1α inhibitors. It is specifically contemplated that one or more of the disclosed HIF1α inhibitors may be excluded from certain embodiments of the disclosure. Also contemplated herein are pharmaceutically acceptable salts and prodrugs of the described HIF1α inhibitors. Although certain example HIF1α inhibitors are described herein, it is contemplated that any HIF1α inhibitor may be implemented in certain embodiments of the disclosure.

In some embodiments, a HIF1α inhibitor is operatively linked (e.g., covalently linked, non-covalently linked, etc.) to a targeting molecule. A targeting molecule describes a molecule designed to bind to a particular biological or cellular target. A targeting molecule may be used to specifically direct or target an agent (e.g., a therapeutic agent such as a HIF1α inhibitor) to a particular biological tissue or cell type (e.g., β-cells). In some embodiments, a targeting molecule is configured to bind to β-cells of a subject. In some embodiments, the targeting molecule is configured to bind to a glucagon-like peptide-1 (GLP-1) receptor, thereby targeting the HIF1α inhibitor to β-cells of the subject. In some embodiments, the targeting molecule is an antibody, antibody fragment, or antibody-like molecule.

B. HIF1α Inhibitory Nucleic Acids

Inhibitory nucleic acids or any ways of inhibiting gene expression of HIF1α known in the art are contemplated in certain embodiments. Examples of an inhibitory nucleic acid include but are not limited to antisense nucleic acids such as: siRNA (small interfering RNA), short hairpin RNA (shRNA), double-stranded RNA, and any other antisense oligonucleotide. Also included are ribozymes or nucleic acids encoding any of the inhibitors described herein. An inhibitory nucleic acid may inhibit the transcription of a gene or prevent the translation of a gene transcript in a cell. An inhibitory nucleic acid may be from 16 to 1000 nucleotides long, and in certain embodiments from 18 to 100 nucleotides long. The nucleic acid may have nucleotides of at least or at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 50, 60, 70, 80, 90 or any range derivable therefrom.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

Inhibitory nucleic acids are well known in the art. For example, siRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

Particularly, an inhibitory nucleic acid may be capable of decreasing the expression of HIF1α by at least 10%, 20%, 30%, or 40%, 50%, 60%, 70%, 75%, 80%, 90%, 95% or more or any range or value derivable therein.

In further embodiments, there are synthetic nucleic acids that are HIF1α inhibitors. An inhibitor may be between 17 to 25 nucleotides in length and may comprise a 5' to 3' sequence that is at least 90% complementary to any portion of the 5' to 3' sequence of a mature HIF1α mRNA. In certain embodiments, an inhibitor molecule is 17, 18, 19, 20, 21, 22, 23, 24, or 25 nucleotides in length, or any range derivable therein. Moreover, an inhibitor molecule has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to any portion of the 5' to 3' sequence of a mature HIF1α mRNA, particularly a mature, naturally occurring mRNA. One of skill in the art could use a portion of the probe sequence that is complementary to the sequence of a mature mRNA as the sequence for an mRNA inhibitor. Moreover, that portion of the probe sequence can be altered so that it is still 90% complementary to the sequence of a mature mRNA.

Example HIF1α inhibitory nucleic acids include EZN-2698.

C. HIF1α Inhibitory Polypeptides

In certain embodiments, disclosed herein is a HIF1α inhibitor polypeptide. In some embodiments, the HIF1α inhibitor polypeptide is a HIF1α antibody. In some embodiments, the anti-HIF1α antibody is a monoclonal antibody or a polyclonal antibody. In some embodiments, the antibody is a chimeric antibody, an affinity matured antibody, a humanized antibody, or a human antibody. In some embodiments, the inhibitor polypeptide is an antibody-like molecule. In some embodiments, the antibody-like is a nanobody. In some embodiments, the antibody is an antibody fragment. In some embodiments, the antibody fragment comprises a Fab, Fab', Fab'-SH, F(ab')2, or scFv. In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a mouse. In one embodiment, an antigen binding sequence is synthetic, e.g., obtained by mutagenesis (e.g., phage display screening, etc.). In one embodiment, a chimeric antibody has murine V regions and human C region. In one embodiment, the murine light chain V region is fused to a human kappa light chain or a human IgG1 C region.

Examples of antibody fragments include, without limitation: (i) the Fab fragment, consisting of VL, VH, CL and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker which allows the two domains to associate to form a binding domain; (viii) bi-specific single chain Fv dimers (see U.S. Pat. No. 5,091,513) and (ix) diabodies, multivalent or multispecific fragments constructed by gene fusion (U.S. Patent Pub. 2005/0214860). Fv, scFv or diabody molecules may be stabilized by the incorporation of disulphide bridges linking the VH and VL domains. Minibodies comprising a scFv joined to a CH3 domain may also be made (Hu et al, 1996).

In some embodiments, disclosed is the use of anti-HIF1α nanobodies, e.g., in treatment of diabetes.

D. HIF1α Inhibitory Small Molecules

As used herein, a "small molecule" refers to an organic compound that is either synthesized via conventional organic chemistry methods (e.g., in a laboratory) or found in nature. Typically, a small molecule is characterized in that it contains several carbon-carbon bonds, and has a molecular weight of less than about 1500 grams/mole. In certain embodiments, small molecules are less than about 1000 grams/mole. In certain embodiments, small molecules are less than about 550 grams/mole. In certain embodiments, small molecules are between about 200 and about 550 grams/mole. In certain embodiments, small molecules exclude peptides (e.g., compounds comprising 2 or more amino acids joined by a peptidyl bond). In certain embodiments, small molecules exclude nucleic acids.

For example, a small molecule HIF1α inhibitor may be any small molecule that is determined to inhibit HIF1α function or activity. Such small molecules may be determined based on functional assays in vitro or in vivo. Certain HIF1α inhibitory molecules (i.e., HIF1α inhibitors) are known in the art and include, for example, KC7F2, IDF-11774, aminoflavone, AJM290, AW464, tanespimycin, alvespimycin, PX-478, FM19G11, resveratrol, rapamycin, everolimus, CCI779, silibinin, digoxin, YC-1, phenethyl isothiocyanite, chetomin, flavopiridol, bortezomib, amphotericin B, Bay 87-2243, PX-478, and ganetasipib.

One or more of the HIF1α inhibitors described herein may be excluded from certain embodiments of the present disclosure.

III. PFKFB3

PFKFB3 is also referred to as 6-phosphofructo-2-kinase/fructose-2,6-biphosphatase 3, 6PF-2-K/Fru-2,6-P2ase Brain/Placenta-Type Isozyme, renal carcinoma antigen NY-REN-56, 6PF-2-K/Fru-2,6-P2ase 3, PFK/FBPase 3, IPFK-2, Inducible 6-Phosphofructo-2-Kinase/Fructose-2,6-Bisphosphatase 3, Fructose-6-Phosphate,2-Kinase/Fructose-2,6-Bisphosphatase 3, 6-Phosphofructo-2-Kinase/Fructose-2,6-Bisphosphatase 3, IPFK2, and PFK2.

The following sequence exemplifies the PFKFB3 mRNA in humans (SEQ ID NO:3):

```
cccttcccc tccctcgccc gccccgccgc ccgcaggcgc cccgagtcgc ggggctgccg cttggacgtc gtcctgtctg ggtgtcgcgg gccggccccg cggggagcgc ccccggcgcg atgcccttca ggaaagcctg tgggccaaag ctgaccaact cccccaccgt catcgtcatg gtgggcctcc ccgcccgggg caagacctac atctccaaga agctgactcg ctacctcaac tggattggcg tccccacaaa agtgttcaac gtcggggagt atcgccggga ggctgtgaag cagtacagct cctacaactt cttccgcccc gacaatgagg aagccatgaa agtccggaag caatgtgcct tagctgcctt gagagatgtc aaaagctacc tggcgaaaga aggggacaa attgcggttt tcgatgccac caatactact agagagagga gacacatgat ccttcatttt gccaaagaaa atgactttaa ggcgtttttc atcgagtcgg tgtgcgacga ccctacagtt gtggcctcca atatcatgga agttaaaatc tccagcccgg attacaaaga ctgcaactcg gcagaagcca tggacgactt catgaagagg atcagttgct atgaagccag ctaccagccc ctcgaccccg acaaatgcga cagggacttg tcgctgatca aggtgattga cgtgggccgg aggttcctgg tgaaccgggt gcaggaccac atccagagcc
```

-continued

```
gcatcgtgta ctacctgatg aacatccacg tgcagccgcg taccatctac ctgtgccggc acggcgagaa cgagcacaac ctccagggcc gcatcggggg cgactcaggc ctgtccagcc ggggcaagaa gtttgccagt gctctgagca agttcgtgga ggagcagaac ctgaaggacc tgcgcgtgtg gaccagccag ctgaagagca ccatccagac ggccgaggcg ctgcggctgc cctacgagca gtggaaggcg ctcaatgaga tcgacgcggg cgtctgtgag gagctgacct acgaggagat cagggacacc taccctgagg agtatgcgct gcgggagcag gacaagtact attaccgcta ccccaccggg gagtcctacc aggacctggt ccagcgcttg gagccagtga tcatggagct ggagcggcag gagaatgtgc tggtcatctg ccaccaggcc gtcctgcgct gcctgcttgc ctacttcctg gataagagtg cagaggagat gccctacctg aaatgccctc ttcacaccgt cctgaaactg acgcctgtcg cttatggctg ccgtgtggaa tccatctacc tgaacgtgga gtccgtctgc acacaccggg agaggtcaga ggatgcaaag aagggaccta acccgctcat gagacgcaat agtgtcaccc cgctagccag ccccgaaccc accaaaaagc ctcgcatcaa cagctttgag gagcatgtgg cctccacctc ggccgccctg cccagctgcc tgcccccgga ggtgcccacg cagctgcctg gacaaaacat gaaaggctcc cggagcagcg ctgactcctc caggaaacac tgaggcagac gtgtcggttc cattccattt ccatttctgc agcttagctt gtgtcctgcc ctccgcccga ggcaaaacgt atcctgagga cttcttccgg agagggtggg gtggagcagc gggggagcct tggccgaaga gaaccatgct tggcaccgtc tgtgtcccct cggccgctgg acaccagaaa gccacgtggg tccctggcgc cctgccttta gccgtggggc ccccacctcc actctctggg tttcctagga atgtccagcc tcggagacct tcacaaagcc ttgggagggt gatgagtgct ggtcctgaca ggaggccgct ggggacactg tgctgtttg tttcgtttct gtgatctccc ggcacgtttg gagctgggaa gaccacactg gtggcagaat cctaaaatta aaggaggcag gctcctagtt gctgaaagtt aaggaatgtg taaaacctcc acgtgactgt ttggtgcatc ttgacctggg aagacgcctc atgggaacga acttggacag gtgttgggtt gaggcctctt ctgcaggaag tccctgagct gagacgcaag ttggctgggt ggtccgcacc ctggctctcc tgcaggtcca cacaccttcc aggcctgtgg cctgcctcca aagatgtgca agggcaggct ggctgcacgg ggagagggaa gtattttgcc gaaatatgag aactggggcc tcctgctccc agggagctcc agggcccctc tctcctccca cctggacttg gggggaactg
```

-continued

```
agaaacactt tcctggagct gctggctttt gcactttttt gatggcagaa gtgtgacctg agagtcccac cttctcttca ggaacgtaga tgttgggggtg tcttgccctg gggggcttgg aacctctgaa ggtgggggagc ggaacacctg gcatccttcc ccagcacttg cattaccgtc cctgctcttc ccaggtgggg acagtggccc aagcaaggcc tcactcgcag ccacttcttc aagagctgcc tgcacactgt cttggagcat ctgccttgtg cctggcactc tgccggtgcc ttgggaaggt cggaagagtg gactttgtcc tggccttccc ttcatggcgt ctatgacact tttgtggtga tggaaagcat gggacctgtc gtctcagcct gttggtttct cctcattgcc tcaaaccctg gggtaggtgg gacgggggt ctcgtgccca gatgaaacca tttggaaact cggcagcaga gtttgtccaa atgacccttt tcaggatgtc tcaaagcttg tgccaaaggt cacttttctt tcctgccttc tgctgtgagc cctgagatcc tcctcccagc tcaagggaca ggtcctgggt gagggtggga gatttagaca cctgaaactg ggcgtggaga gaagagccgt tgctgtttgt tttttgggaa gagctttttaa agaatgcatg ttttttttcct ggttggaatt gagtaggaac tgaggctgtg cttcaggtat ggtacaatca agtgggggat tttcatgctg aaccattcaa gccctccccg cccgttgcac ccactttggc tggcgtctgc tggagaggat gtctctgtcc gcattcccgt gcagctccag gctcgcgcag ttttctctct ctccctggat gttgagtctc atcagaatat gtgggtaggg ggtggacgtg cacgggtgca tgattgtgct taacttggtt gtatttttcg atttgacatg gaaggcctgt tgctttgctc ttgagaatag tttctcgtgt ccccctcgca ggcctcattc tttgaacatc gactctgaag tttgatacag atagggggctt gatagctgtg gtcccctctc ccctctgact acctaaaatc aatacctaaa tacagaagcc ttggtctaac acgggacttt tagtttgcga agggcctaga tagggagaga ggtaacatga atctggacag ggagggagat actatagaaa ggagaacact gcctactttg caagccagtg acctgccttt tgaggggaca ttggacgggg gccggggggcg ggggttgggt ttgagctaca gtcatgaact tttggcgtct actgattcct ccaactctcc accccacaaa ataacgggga ccaatatttt taactttgcc tatttgtttt tgggtgagtt tccccccctcc ttattctgtc ctgagaccac gggcaaagct cttcattttg agagagaaga aaaactgttt ggaaccacac caatgatatt tttctttgta atacttgaaa tttatttttt tattattttg atagcagatg tgctatttat ttatttaata tgtataagga
```

-continued

```
gcctaaacaa tagaaagctg tagagattgg gtttcattgt taattggttt gggagcctcc tatgtgtgac ttatgacttc tctgtgttct gtgtatttgt ctgaattaat gacctgggat ataaagctat gctagctttc aaacaggaga tgcctttcag aaatttgtat attttgcagt tgccagacca ataaaatacc tggttgaaat acatggacga agtaaa.
```

The protein sequence is exemplified by the following (SEQ ID NO:4):

```
MPFRKACGPKLTNSPTVIVMVGLPARGKTYISKKLTRYLNWIGVP

TKVFNVGEYRREAVKQYSSYNFFRPDNEEAMKVRKQCALAALRD

VKSYLAKEGGQIAVFDATNTTRERRHMILHFAKENDFKAFFIES

VCDDPTVVASNIMEVKISSPDYKDCNSAEAMDDFMKRISCYEAS

YQPLDPDKCDRDLSLIKVIDVGRRFLVNRVQDHIQSRIVYYLMN

IHVQPRTIYLCRHGENEHNLQGRIGGDSGLSSRGKKFASALSKF

VEEQNLKDLRVWTSQLKSTIQTAEALRLPYEQWKALNEIDAGVC

EELTYEEIRDTYPEEYALREQDKYYYRYPTGESYQDLVQRLEPV

IMELERQENVLVICHQAVLRCLLAYFLDKSAEEMPYLKCPLHTV

LKLTPVAYGCRVESIYLNVESVCTHRERSEDAKKGPNPLMRRNS

VTPLASPEPTKKPRINSFEEHVASTSAALPSCLPPEVPTQLPGQ

NMKGSRSSADSSRKH.
```

The above protein and mRNA sequence represents one isoform (isoform 2) of the gene, but other isoforms are known in the art. For example, the Genbank numbers below represent additional isoforms. The sequences associated with these Genbank numbers are incorporated by reference for all purposes.

| Isoform | GenBank mRNA | GenBank protein |
|---|---|---|
| 6-phosphofructo-2-kinase/ fructose-2,6- bisphosphatase 3 isoform 2 | NM_001145443.2 | NP_001138915.1 |
| 6-phosphofructo-2-kinase/ fructose-2,6- bisphosphatase 3 isoform 3 | NM_001282630.2 | NP_001269559.1 |
| 6-phosphofructo-2-kinase/ fructose-2,6- bisphosphatase 3 isoform 4 | NM_001314063.1 | NP_001300992.1 |
| 6-phosphofructo-2-kinase/ fructose-2,6- bisphosphatase 3 isoform 5 | NM_001323016.1 | NP_001309945.1 |
| 6-phosphofructo-2-kinase/ fructose-2,6- bisphosphatase 3 isoform 6 | NM_001323017.1 | NP_001309946.1 |
| 6-phosphofructo-2-kinase/ fructose-2,6- bisphosphatase 3 isoform 1 | NM_004566.3 | NP_004557.1 |

The protein encoded by this gene belongs to a family of bifunctional proteins that are involved in both the synthesis and degradation of fructose-2,6-bisphosphate, a regulatory molecule that controls glycolysis in eukaryotes. The encoded protein has a 6-phosphofructo-2-kinase activity that catalyzes the synthesis of fructose-2,6-bisphosphate (F2, 6BP), and a fructose-2,6-biphosphatase activity that catalyzes the degradation of F2,6BP. This protein is required for cell cycle progression and prevention of apoptosis. It functions as a regulator of cyclin-dependent kinase 1, linking glucose metabolism to cell proliferation and survival in tumor cells.

A. PFKFB3 Inhibitors

A PFKFB3 inhibitor may refer to any member of the class of compound or agents having an $IC_{50}$ of 200 µM or lower concentration for a PFKFB3 activity, for example, at least or at most or about 200, 100, 80, 50, 40, 20, 10, 5, 1 µM, 100, 10, 1 nM or lower concentration (or any range or value derivable therefrom) or any compound or agent that inhibits the expression of PFKFB3. Examples of PFKFB3 activity or function may include, but not be limited to, regulation of glycolysis, kinase activity, regulation of CDK1, 6-phospho-fructo-2-kinase activity, fructose-2,6-bisphosphate 2-phosphatase activity, ATP binding activity, and enzyme catalysis activity. In some embodiments, the inhibition can be a decrease as compared with a control level or sample. In further embodiments, a functional assay such as MTT assay, cell proliferation assay, Ki67 immunofluoresence, apoptosis assay, or glycolysis assay may be used to test the PFKFB3 inhibitors. Methods and compositions of the disclosure may comprise one or more PFKFB3 inhibitors. It is specifically contemplated that one or more of the disclosed PFKFB3 inhibitors may be excluded from certain embodiments of the disclosure. Also contemplated herein are pharmaceutically acceptable salts and prodrugs of the described PFKFB3 inhibitors. Although certain example PFKFB3 inhibitors are described herein, it is contemplated that any PFKFB3 inhibitor may be implemented in certain embodiments of the disclosure.

In some embodiments, a PFKFB3 inhibitor is operatively linked (e.g., covalently linked, non-covalently linked, etc.) to a targeting molecule. A targeting molecule describes a molecule designed to bind to a particular biological or cellular target. A targeting molecule may be used to specifically direct or target an agent (e.g., a therapeutic agent such as a PFKFB3 inhibitor) to a particular biological tissue or cell type (e.g., β-cells). In some embodiments, a targeting molecule is configured to bind to β-cells of a subject. In some embodiments, the targeting molecule is configured to bind to a glucagon-like peptide-1 (GLP-1) receptor, thereby targeting the PFKFB3 inhibitor to β-cells of the subject. In some embodiments, the targeting molecule is an antibody or antibody-like molecule.

B. PFKFB3 Inhibitory Nucleic Acids

Inhibitory nucleic acids or any ways of inhibiting gene expression of PFKFB3 known in the art are contemplated in certain embodiments. Examples of an inhibitory nucleic acid include but are not limited to antisense nucleic acids such as: siRNA (small interfering RNA), short hairpin RNA (shRNA), double-stranded RNA, an any other antisense oligonucleotide. Also included are ribozymes or nucleic acids encoding any of the inhibitors described herein. An inhibitory nucleic acid may inhibit the transcription of a gene or prevent the translation of a gene transcript in a cell. An inhibitory nucleic acid may be from 16 to 1000 nucleotides long, and in certain embodiments from 18 to 100 nucleotides long. The nucleic acid may have nucleotides of at least or at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 50, 60, 70, 80, 90 or any range derivable therefrom.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

Inhibitory nucleic acids are well known in the art. For example, siRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

Particularly, an inhibitory nucleic acid may be capable of decreasing the expression of PFKFB3 by at least 10%, 20%, 30%, or 40%, 50%, 60%, 70%, 75%, 80%, 90%, 95% or more or any range or value derivable therein.

In further embodiments, there are synthetic nucleic acids that are PFKFB3 inhibitors. An inhibitor may be between 17 to 25 nucleotides in length and comprises a 5' to 3' sequence that is at least 90% complementary to any portion of the 5' to 3' sequence of a mature PFKFB3 mRNA. In certain embodiments, an inhibitor molecule is 17, 18, 19, 20, 21, 22, 23, 24, or 25 nucleotides in length, or any range derivable therein. Moreover, an inhibitor molecule has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to any portion of the 5' to 3' sequence of a mature PFKFB3 mRNA, particularly a mature, naturally occurring mRNA. One of skill in the art could use a portion of the probe sequence that is complementary to the sequence of a mature mRNA as the sequence for an mRNA inhibitor. Moreover, that portion of the probe sequence can be altered so that it is still 90% complementary to the sequence of a mature mRNA.

Inhibitor nucleic acids for PFKFB3 are also commercially available. For example, the following miRNAs may inhibit PFKFB3: hsa-mir-26b-5p (MIRT028775), hsa-mir-330-3p (MIRT043840), hsa-mir-6779-5p (MIRT454747), hsa-mir-6780a-5p (MIRT454748), hsa-mir-3689c (MIRT454749), hsa-mir-3689b-3p (MIRT454750), hsa-mir-3689a-3p (MIRT454751), hsa-mir-30b-3p (MIRT454752), hsa-mir-1273h-5p (MIRT454753), hsa-mir-6778-5p (MIRT454754), hsa-mir-1233-5p (MIRT454755), hsa-mir-6799-5p (MIRT454756), hsa-mir-7106-5p (MIRT454757), hsa-mir-6775-3p (MIRT454758), hsa-mir-1291 (MIRT454759), hsa-mir-765 (MIRT454760), hsa-mir-423-5p (MIRT454761), hsa-mir-3184-5p (MIRT454762), hsa-mir-6856-5p (MIRT454763), hsa-mir-6758-5p (MIRT454764), hsa-mir-3185 (MIRT527973), hsa-mir-6892-3p (MIRT527974), hsa-mir-6840-5p (MIRT527975), and hsa-mir-6865-3p (MIRT527976).

siRNAs and shRNAs are also commercially available from, for example, Santa Cruz biotechnology (sc-44011 and sc-44011-SH, respectively).

C. PFKFB3 Inhibitory Polypeptides

In certain embodiments, disclosed herein is a PFKFB3 inhibitor peptide. In some embodiments, the PFKFB3 inhibitor polypeptide is a PFKFB3 antibody. In some embodiments, the anti-PFKFB3 antibody is a monoclonal antibody or a polyclonal antibody. In some embodiments, the antibody is a chimeric antibody, an affinity matured antibody, a humanized antibody, or a human antibody. In some embodiments, the antibody is an antibody-like molecule. In some embodiments, the antibody is an antibody fragment. In some embodiments, the antibody fragment comprises a Fab, Fab', Fab'-SH, F(ab')2, or scFv. In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a mouse. In one embodiment, an antigen binding sequence is synthetic, e.g., obtained by mutagenesis (e.g., phage display screening, etc.). In one embodiment, a chimeric antibody has murine V regions and human C region. In one embodiment, the murine light chain V region is fused to a human kappa light chain or a human IgG1 C region.

Examples of antibody fragments include, without limitation: (i) the Fab fragment, consisting of VL, VH, CL and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker which allows the two domains to associate to form a binding domain; (viii) bi-specific single chain Fv dimers (see U.S. Pat. No. 5,091,513) and (ix) diabodies, multivalent or multispecific fragments constructed by gene fusion (U.S. Patent Pub. 2005/0214860). Fv, scFv or diabody molecules may be stabilized by the incorporation of disulphide bridges linking the VH and VL domains. Minibodies comprising a scFv joined to a CH3 domain may also be made (Hu et al, 1996).

D. PFKFB3 Inhibitory Small Molecules

As used herein, a "small molecule" refers to an organic compound that is either synthesized via conventional organic chemistry methods (e.g., in a laboratory) or found in nature. Typically, a small molecule is characterized in that it contains several carbon-carbon bonds, and has a molecular weight of less than about 1500 grams/mole. In certain embodiments, small molecules are less than about 1000 grams/mole. In certain embodiments, small molecules are less than about 550 grams/mole. In certain embodiments, small molecules are between about 200 and about 550 grams/mole. In certain embodiments, small molecules exclude peptides (e.g., compounds comprising 2 or more amino acids joined by a peptidyl bond). In certain embodiments, small molecules exclude nucleic acids.

For example, a small molecule PFKFB3 inhibitor may be any small molecule that is determined to inhibit PFKFB3 function or activity. Such small molecules may be determined based on functional assays in vitro or in vivo. In some embodiments, a PFKFB3 inhibitor of the present disclosure is a PFKFB3 inhibitory molecule. PFKFB3 inhibitory molecules are known in the art and described in, for example, U.S. Patent publications 20130059879, 20120177749, 20100267815, 20100267815, and 20090074884, which are herein incorporated by reference.

Example inhibitory compounds include: (1H-Benzo[g] indol-2-yl)-phenyl-methanone; (3H-Benzo[e]indol-2-yl)-phenyl-methanone; (3H-Benzo[e]indol-2-yl)-(4-methoxy-phenyl)-methanone; (3H-Benzo[e]indol-2-yl)-pyridin-4-yl-methanone; HCl salt of (3H-Benzo[e]indol-2-yl)-pyridin-4-yl-methanone; (3H-Benzo[e]indol-2-yl)-(3-methoxy-phenyl)-methanone; (3H-Benzo[e]indol-2-yl)-pyridin-3-yl-methanone; (3H-Benzo[e]indol-2-yl)-(2-methoxy-phenyl)-methanone; (3H-Benzo[e]indol-2-yl)-(2-hydroxy-phenyl)-methanone; (3H-Benzo[e]indol-2-yl)-(4-hydroxy-phenyl)-methanone; (5-Methyl-3H-benzo[e]indol-2-yl)-phenyl-methanone; Phenyl-(7H-pyrrolo [2,3-h]quinolin-8-yl)- methanone; (3H-Benzo[e]indol-2-yl)-(3-hydroxy-phenyl)-methanone; (3H-benzo[e]indol-2-yl)-(2-chloro-pyridin-4-yl)-methanone; (3H-benzo[e]indol-2-yl)-(1-oxy-pyridin-4-yl)-methanone; Phenyl-(6,7,8,9-tetrahydro-3H-benzo[e] indol-2-yl)-methanone; (3H-Benzo[e]indol-2-yl)-(4-hydroxy-3-methoxylthenyl)-methanone; (3H-Benzo[e] indol-2-yl)-(4-benzyloxy-3-methoxy-phenyl)-methanone; 4-(3H-Benzo[e]indole-2-carbonyl)-benzoic acid methyl ester; 4-(3H-Benzo[e]indole-2-carbonyl)-benzoic acid; (4-Amino-phenyl)-(3H-benzo[e]indol-2-yl)-methanone; 5-(3H-Benzo[e]indole-2-carbonyl)-2-benzyloxy-benzoic acid methyl; 5-(3H-Benzo[e]indole-2-carbonyl)-2-benzy-loxy-benzoic Acidmethanone; (3H-Benzo[e]indol-2-yl)-(2-methoxy-pyridin-4-yl)-methanone; (5-Fluoro-3H-benzo[e] indol-2-yl)-(3-methoxy-phenyl)-methanone; (5-Fluoro-3H-benzo[e]indol-2-yl)-pyridin-4-yl-methanone; (4-Benzy-loxy-3-methoxy-phenyl)-(5-fluoro-3H-benzo[e]indol-2-yl)-methanone; (5-Fluoro-3H-benzo[e]indol-2-yl)-(4-hydroxy-3-methoxy-phenyl)-methanone; (3H-Benzo[e]indol-2-yl)-(3-hydroxymethyl-phenyl)-methanone; Cyclohexyl-(5-fluoro-3H-benzo[e]indol-2-yl)-methanone; (5-Fluoro-3H-benzo[e]indol-2-yl)-(3-fluoro-4-hydroxy-phenyl)-meth-anone; (3H-Benzo[e]indol-2-yl)-p-tolyl-methanone; (3H-Benzo[e]indol-2-yl)-(3-methoxy-phenyl)-methanol; (3H-Benzo[e]indol-2-yl)-pyridin-4-yl-methanol; 3H-Benzo[e] indole-2-carboxylic acid phenylamide; 3H-Benzo[e]indole-2-carboxylic acid (3-methoxy-phenyl)-amide; (3H-Benzo[e] indol-2-yl)-(4-dimethylamino-phenyl)-methanone; (4-Amino-3-methoxy-phenyl)-(3H-benzo[e]indol-2-yl)-methanone; (4-Amino-3-methoxy-phenyl)-(5-hydroxy-3H-benzo[e]indol-2-yl)-methanone; (4-Amino-3-methoxy-phe-nyl)-(5-methoxy-3H-benzo[e]indol-2-yl)-methanone; N-[4-(3H-Benzo[e]indole-2-carbonyl)-phenyl]-methanesu-lfonamide; 3H-Benzo[e]indole-2-carboxylic acid (4-amino-phenyl)-amide; (4-Amino-phenyl)-(5-methoxy-3H-benzo [e]indol-2-yl)-methanone; (4-Amino-2-fluoro-phenyl)-(5-methoxy-3H-benzo[e]indol-2-yl)-methanone; (4-Amino-3-fluoro-phenyl)-(5-methoxy-3H-benzo[e]indol-2-yl)-methanone; (4-Amino-2-methoxy-phenyl)-(5-methoxy-3H-benzo[e]indol-2-yl)-methanone; (4-Amino-phenyl)-(9-methoxy-3H-benzo[e]indol-2-yl)-methanone; (4-Amino-3-methoxy-phenyl)-(9-methoxy-3H-benzo[e]indol-2-yl)-methanone; (4-Amino-2-methoxy-phenyl)-(9-methoxy-3H-benzo[e]indol-2-yl)-methanone; (4-Amino-3-fluoro-phenyl)-(9-methoxy-3H-benzo[e]indol-2-yl)-methanone; (4-Amino-2-fluoro-phenyl)-(9-methoxy-3H-benzo[e]indol-2-yl)-methanone; (4-Amino-3-fluoro-phenyl)-(3H-benzo[e] indol-2-yl)-methanone; (4-Amino-2-fluoro-phenyl)-(3H-benzo[e]indol-2-yl)-methanone; (4-Amino-phenyl)-(7-methoxy-3H-benzo[e]indol-2-yl)-methanone; (4-Amino-phenyl)-(5-hydroxy-3-methyl-3H-benzo[e]indol-2-yl)-methanone; (7-Amino-5-fluoro-9-hydroxy-3H-benzo[e] indol-2-yl)-(3-methyl-pyridin-4-yl)-methanone; (5-Amino-3H-pyrrolo[3,2-f]isoquinolin-2-yl)-(3-methoxy-pyridin-4-yl)-methanone; (4-Amino-2-methyl-phenyl)-(9-hydroxy-3H-pyrrolo[2,3-c]quinolin-2-yl)-methanone; and (4-Amino-phenyl)-(7-methanesulfonyl-3H-benzo[e]indol-2-yl)-methanone.

Further example inhibitory compounds include: 1-Pyri-din-4-yl-3-quinolin-4-yl-propenone; 1-Pyridin-4-yl-3-qui-nolin-3-yl-propenone; 1-Pyridin-3-yl-3-quinolin-2-yl-pro-penone; 1-Pyridin-3-yl-3-quinolin-4-yl-propenone; 1-Pyridin-3-yl-3-quinolin-3-yl-propenone; 1-Naphthalen-2-yl-3-quinolin-2-yl-propenone; 1-Naphthalen-2-yl-3-quino-lin-3-yl-propenone; 1-Pyridin-4-yl-3-quinolin-3-yl-prope-none; 3-(4-Hydroxy-quinolin-2-yl)-1-pyridin-4-yl-propenone; 3-(8-Hydroxy-quinolin-2-yl)-1-pyridin-3-ylpropenone; 3-Quinolin-2-yl-1-p-tolyl-propenone; 3-(8-Hydroxy-quinolin-2-yl)-1-pyridin-4-yl-propenone; 3-(8-Hydroxy-quinolin-2-yl)-1-p-tolyl-propenone; 3-(4-Hydroxy-quinolin-2-yl)-1-p-tolyl-propenone; 1-Phenyl-3-quinolin-2-yl-propenone; 1-Pyridin-2-yl-3-quinolin-2-yl-propenone; 1-(2-Hydroxy-phenyl)-3-quinolin-2-yl-propenone; 1-(4-Hydroxy-phenyl)-3-quinolin-2-yl-propenone; 1-(2-Amino-phenyl)-3-quinolin-2-yl-propenone; 1-(4-Amino-phenyl)-3-quinolin-2-yl-prop enone; 4-(3-Quinolin-2-yl-acryloyl)-benzamide; 4-(3-Qui-nolin-2-yl-acryloyl)-benzoic acid; 3-(8-Methyl-quinolin-2-yl)-1-pyridin-4-yl-propenone; 1-(2-Fluoro-pyridin-4-yl)-3-quinolin-2-yl-propenone; 3-(8-Fluoro-quinolin-2-yl)-1-pyridin-4-yl-propenone; 3-(6-Hydroxy-quinolin-2-yl)-1-pyridin-4-yl-propenone; 3-(8-Methylamino-quinolin-2-yl)-1-pyridin-4-yl-propenone; 3-(7-Methyl-quinolin-2-yl)-1-pyridin-4-yl-propenone; and 1-Methyl-4-[3-(8-methyl-quinolin-2-yl)-acrylo yl]-pyridinium.

Further example inhibitory compounds include: PFK15 (1-(4-pyridinyl)-3-(2-quinolinyl)-2-propen-1-one); (2S)—N-[4-[[3-Cyano-1-(2-methylpropyl)-1H-indol-5-yl]oxy] phenyl]-2-pyrrolidinecarboxamide 3PO (3-(3-Pyridinyl)-1-(4-pyridinyl)-2-propen-1-one); (2S)—N-[4-[[3-Cyano-1-[(3,5-dimethyl-4-isoxazolyl)methyl]-1H-indol-5-yl]oxy] phenyl]-2-pyrrolidinecarboxamide; and Ethyl 7-hydroxy-2-oxo-2H-1-benzopyran-3-carboxylate.

Further example inhibitory compounds include: N-bro-moacetylethanolamine phosphate (BrAcNHEtOP), 7,8-di-hydroxy-3-(4-hydroxyphenyl) chromen-4-one (YN1), ethyl 7-hydroxy-2-oxochromene-3-carboxylate (YZ9), 1-(3-pyridinyl)-3-(2-quinolinyl)-2-propen-1-one (PQP), PFK-158, Compound 26 (Boyd et al. J. Med Chem 2015), KAN0436151, and KAN0436067.

One or more of the PFKFB3 inhibitory molecules described herein may be excluded from certain embodiments of the present disclosure.

IV. Elimination of Bihormonal Cells

Aspects of the present disclosure are directed to methods for elimination of bihormonal cells from a population of cells, as well as compositions for use thereof. As used herein, the term "bihormonal cells" (also "polyhormonal cells") refers to cells which produce oth insulin (i.e., are "insulin+") and glucagon (i.e., are "glucacon+"). Such bihor-monal cells are recognized in the art and are described in, for example, J E, Erener S. et al., Stem Cell Res. 2014 January; 12(1):194-208 and Alvarez-Dominguez J R, et al. Cell Stem Cell. 2020 January 2; 26(1):108-122.e10, each of which is incorporated by reference herein.

As disclosed herein, inhibition of PFKFB3 and/or HIF1α can be used to eliminate bihormonal cells from a population of, for example, pancreatic islet cells. Accordingly, aspects of the disclosure are directed to methods for eliminatin of bihormonal cells from a population of cells comprising providing a PFKFB3 inhibitor and/or a HIF1α inhibitor. In some embodiments, the inhibitor is provided to the popula-tion of cells in vitro. In some embodiments, the inhibitor is provided to the population of cells in vivo. In some embodi-ments, the population of cells comprises differentiated stem cells. Such differentiated stem cells include, for example, pancreatic islet cells derived from differentiated stem cells and bihormonal cells derived from differentiated stem cells. In some embodiments, the stem cells are induced pluripotent stem cells (iPSCs). In some embodiments, the stem cells are embryonic stem cells. In some embodiments, the stem cells are obtained from a patient having, at risk of having, or suspected of having Type 1 diabetes or Type 2 diabetes. The disclosed methods may further comprise, after providing the PFKFB3 inhibitor and/or HIF1α inhibitor, administering the population of cells to a subject. In some embodiments, the subject has, is at risk of having, or is suspected of having Type 1 diabetes or Type 2 diabetes. In some embodiments, the population of cells are autologous to the subject. In some embodiments, the population of cells are not autologous to the subject.

V. Pharmaceutical Compositions

Embodiments include methods for treating diabetes with compositions comprising a HIF1α inhibitor and/or a PFKFB3 inhibitor. In some embodiments, a disclosed com-position comprises a HIF1α inhibitor. In some embodi-ments, a disclosed composition comprises a PFKFB3 inhibi-tor. In some embodiments, a disclosed composition comprises a HIF1α inhibitor and a PFKFB3 inhibitor. Administration of the compositions will typically be via any common route. This includes, but is not limited to oral, parenteral, orthotopic, intradermal, subcutaneous, intramus-cular, intraperitoneal, intranasal, intratumoral, or intrave-nous injection. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, or about 25% to about 70%. In some embodi-ments, the compositions are administered orally.

Typically, compositions are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner.

The manner of application may be varied widely. Any of the conventional methods for administration of a pharma-ceutical composition are applicable. These are believed to include oral application on a solid physiologically accept-able base or in a physiologically acceptable dispersion, parenterally, by injection and the like. The dosage of the pharmaceutical composition will depend on the route of administration and will vary according to the size and health of the subject.

In many instances, it will be desirable to have multiple administrations of at most about or at least about 3, 4, 5, 6, 7, 8, 9, 10 or more. The administrations may range from 2 day to twelve week intervals, more usually from one to two week intervals. The course of the administrations may be followed by assays for HIF1α and/or PFKFB3 activity.

The phrases "pharmaceutically acceptable" or "pharma-cologically acceptable" refer to molecular entities and com-positions that do not produce an adverse, allergic, or other untoward reaction when administered to an animal, or human. As used herein, "pharmaceutically acceptable car-rier" includes any and all solvents, dispersion media, coat-ings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

"Pharmaceutically acceptable salts" means salts of com-pounds (e.g., inihbitors, PFKFB3 inhibitors) of the present invention which are pharmaceutically acceptable, as defined above, and which possess the desired pharmacological activ-ity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic: sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, make acid, malonic acid, mandelic acid, methanesulfonic acid, muconic acid, o-4-hydroxybenzoyl)benzoic acid, oxalic acid, p-chlorobenzenesulfonic acid, phenyl-substituted alkapoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, and Use (P. H, Stahl & C. G Wermuth eds., *Verlag Helvetica Chimica Acta,* 2002).

The disclosed compositions may include a prodrug. "Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates oxalates, salicylates, propionates, succinates, fumarases, maleates, methylene-bis-β-hydroxynaphthoate, gentisates, isethionates, di-p-toluoyltartrates, methanesulfonates, ethanesulfonates, benzenesuifonates, p-toluenesulfonates, cyclohexylsulfamates, quinates, esters of amino acids, and the like. Similarly, a compound comprising an amine group may be administered as an amide that is converted by hydrolysis in vivo to the amine compound.

The HIF1α inhibitors and/or a PFKFB3 inhibitors can be formulated for parenteral administration, e.g., formulated for injection via the intravenous, intradermal, intramuscular, sub-cutaneous, or even intraperitoneal routes. In some embodiments, the composition is administered by intravenous injection. The preparation of an aqueous composition that contains an active ingredient will be known to those of skill in the art in light of the current disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredients in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

Upon formulation, solutions will be administered in a manner compatible with the dosage formulation and in such amount as is therapeutically or prophylactically effective. The formulations are easily administered in a variety of dosage forms, such as the type of injectable solutions described above.

As an example, for a human adult (weighing approximately 70 kilograms), from about 0.1 mg to about 3000 mg (including all values and ranges there between), or from about 5 mg to about 1000 mg (including all values and ranges there between), or from about 10 mg to about 100 mg (including all values and ranges there between), of a compound are administered. It is understood that these dosage ranges are by way of example only, and that administration can be adjusted depending on the factors known to the skilled artisan.

In certain embodiments, a subject is administered about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or µg/kg or micrograms/kg/minute or mg/kg/min or micrograms/kg/hour or mg/kg/hour, or any range derivable therein.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of a condition. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of the condition (or any range derivable therein). The patient may be treated for 1, 2, 3, 4, 5, 6, 7, 8, 9, 10 or more days (or any range derivable therein) or until symptoms of an the condition have disappeared or been reduced or after 6, 12, 18, or 24 hours or 1, 2, 3, 4, or 5 days after symptoms of an infection have disappeared or been reduced.

VI. Administration of Therapeutic Compositions and Combinations

The therapy provided herein may comprise administration of a combination of therapeutic agents, such as a first treatment (e.g., HIF1α inhibitor) and a second treatment (e.g., a PFKFB3 inhibitor). The therapies may be administered in any suitable manner known in the art. For example, the first and second treatment may be administered sequentially (at different times) or concurrently (at the same time). In some embodiments, the first and second treatments are administered in a separate composition. In some embodiments, the first and second treatments are in the same composition.

Embodiments of the disclosure relate to compositions and methods comprising therapeutic compositions. The different therapies may be administered in one composition or in more than one composition, such as 2 compositions, 3 compositions, or 4 compositions. Various combinations of the agents may be employed.

The therapeutic agents of the disclosure may be administered by the same route of administration or by different routes of administration. In some embodiments, the therapy is administered intravenously, intramuscularly, subcutaneously, topically, orally, transdermally, intraperitoneally, intraorbitally, by implantation, by inhalation, intrathecally, intraventricularly, or intranasally. In some embodiments, the antibiotic is administered intravenously, intramuscularly, subcutaneously, topically, orally, transdermally, intraperitoneally, intraorbitally, by implantation, by inhalation, intrathecally, intraventricularly, or intranasally. The appropriate dosage may be determined based on the type of disease to be treated, severity and course of the disease, the clinical condition of the individual, the individual's clinical history and response to the treatment, and the discretion of the attending physician.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some embodiments, a unit dose comprises a single administrable dose.

The quantity to be administered, both according to number of treatments and unit dose, depends on the treatment effect desired. An effective dose is understood to refer to an amount necessary to achieve a particular effect. In the practice in certain embodiments, it is contemplated that doses in the range from 10 mg/kg to 200 mg/kg can affect the protective capability of these agents. Thus, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200, 300, 400, 500, 1000 µg/kg, mg/kg, µg/day, or mg/day or any range derivable therein. Furthermore, such doses can be administered at multiple times during a day, and/or on multiple days, weeks, or months.

In certain embodiments, the effective dose of the pharmaceutical composition is one which can provide a blood level of about 1 µM to 150 µM. In another embodiment, the effective dose provides a blood level of about 4 µM to 100

μM; or about 1 μM to 100 μM; or about 1 μM to 50 μM; or about 1 μM to 40 μM; or about 1 μM to 30 μM; or about 1 μM to 20 μM; or about 1 μM to 10 μM; or about 10 μM to 150 μM; or about 10 μM to 100 μM; or about 10 μM to 50 μM; or about 25 μM to 150 μM; or about 25 μM to 100 μM; or about 25 μM to 50 μM; or about 50 μM to 150 μM; or about 50 μM to 100 μM (or any range derivable therein). In other embodiments, the dose can provide the following blood level of the agent that results from a therapeutic agent being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 μM or any range derivable therein. In certain embodiments, the therapeutic agent that is administered to a subject is metabolized in the body to a metabolized therapeutic agent, in which case the blood levels may refer to the amount of that agent. Alternatively, to the extent the therapeutic agent is not metabolized by a subject, the blood levels discussed herein may refer to the unmetabolized therapeutic agent.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

It will be understood by those skilled in the art and made aware that dosage units of μg/kg or mg/kg of body weight can be converted and expressed in comparable concentration units of μg/ml or mM (blood levels), such as 4 μM to 100 μM. It is also understood that uptake is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein.

VII. Detecting a Genetic Signature

Particular embodiments concern the methods of detecting a genetic signature in an individual. In some embodiments, the method for detecting the genetic signature may include selective oligonucleotide probes, arrays, allele-specific hybridization, molecular beacons, restriction fragment length polymorphism analysis, enzymatic chain reaction, flap endonuclease analysis, primer extension, 5'-nuclease analysis, oligonucleotide ligation assay, single strand conformation polymorphism analysis, temperature gradient gel electrophoresis, denaturing high performance liquid chromatography, high-resolution melting, DNA mismatch binding protein analysis, surveyor nuclease assay, sequencing, or a combination thereof, for example. The method for detecting the genetic signature may include fluorescent in situ hybridization, comparative genomic hybridization, arrays, polymerase chain reaction, sequencing, or a combination thereof, for example. The detection of the genetic signature may involve using a particular method to detect one feature of the genetic signature and additionally use the same method or a different method to detect a different feature of the genetic signature. Multiple different methods independently or in combination may be used to detect the same feature or a plurality of features. In some embodiments, the disclosed methods comprise detecting an expression level of PFKFB3 in cells (e.g., β-cells) from a subject.

A. DNA Sequencing

In some embodiments, DNA may be analyzed by sequencing. The DNA may be prepared for sequencing by any method known in the art, such as library preparation, hybrid capture, sample quality control, product-utilized ligation-based library preparation, or a combination thereof. The DNA may be prepared for any sequencing technique. In some embodiments, sequencing, may be performed to cover approximately 70%, 75%, 80%, 85%, 90%, 95%, 99%, or greater percentage of targets at more than 20×, 25×, 30×, 35×, 40×, 45×, 50×, or greater than 50× coverage. In some embodiments, DNA sequencing is used to determine an expression level of PFKFB3 in cells (e.g., β-cells) from a subject.

B. RNA Sequencing

In some embodiments, RNA may be analyzed by sequencing. The RNA may be prepared for sequencing by any method known in the art, such as poly-A selection, cDNA synthesis, stranded or nonstranded library preparation, or a combination thereof. The RNA may be prepared for any type of RNA sequencing technique, including stranded specific RNA sequencing. In some embodiments, sequencing may be performed to generate approximately 10 M, 15 M, 20 M, 25 M, 30 M, 35 M, 40 M or more reads, including paired reads. The sequencing may be performed at a read length of approximately 50 bp, 55 bp, 60 bp, 65 bp, 70 bp, 75 bp, 80 bp, 85 bp, 90 bp, 95 bp, 100 bp, 105 bp, 110 bp, or longer. In some embodiments, raw sequencing data may be converted to estimated read counts (RSEM), fragments per kilobase of transcript per million mapped reads (FPKM), and/or reads per kilobase of transcript per million mapped reads (RPKM). In some embodiments, RNA sequencing is used to determine an expression level of PFKFB3 in cells (e.g., β-cells) from a subject.

C. Proteomics

In some embodiments, protein may be analyzed by mass spectrometry. The protein may be prepared for mass spectrometry using any method known in the art. Protein, including any isolated protein encompassed herein, may be treated with DTT followed by iodoacetamide. The protein may be incubated with at least one peptidase, including an endopeptidase, proteinase, protease, or any enzyme that cleaves proteins. In some embodiments, protein is incubated with the endopeptidase, LysC and/or trypsin. The protein may be incubated with one or more protein cleaving enzymes at any ratio, including a ratio of μg of enzyme to μg protein at approximately 1:1000, 1:100, 1:90, 1:80, 1:70, 1:60, 1:50, 1:40, 1:30, 1:20, 1:10, 1:1, or any range between. In some embodiments, the cleaved proteins may be purified, such as by column purification. In certain embodiments, purified peptides may be snap-frozen and/or dried, such as dried under vacuum. In some embodiments, the purified peptides may be fractionated, such as by reverse phase chromatography or basic reverse phase chromatography. Fractions may be combined for practice of the methods of the disclosure. In some embodiments, one or more fractions, including the combined fractions, are subject to phospho-peptide enrichment, including phospho-enrichment by affinity chromatography and/or binding, ion exchange chromatography, chemical derivatization, immunoprecipitation, co-precipitation, or a combination thereof. The entirety or a portion of one or more fractions, including the combined fractions and/or phospho-enriched fractions, may be subject to mass spectrometry. In some embodiments, the raw mass spectrometry data may be processed and normalized using at least one relevant bioinformatics tool. In some embodiments, proteomics is used to determine an amount of PFKFB3 in cells (e.g., β-cells) from a subject.

VIII. Kits

Certain aspects of the present invention also concern kits containing compositions of the disclosure or compositions to implement methods of the disclosure. In some embodiments, kits can be used to evaluate one or more biomarkers. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more probes, primers or primer sets, synthetic molecules or inhibitors, or any value or range and combination derivable therein. In some embodiments, there are kits for evaluating biomarker activity in a cell. In some embodiments, disclosed are kits for evaluating an expression level of one or more biomarker activities. In some embodiments, disclosed are kits for evaluating an expression level of PFKFB3 in β-cells from a subject.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using probes, synthetic nucleic acids, nonsynthetic nucleic acids, and/or inhibitors of the disclosure for prognostic or diagnostic applications are included as part of the disclosure. Specifically contemplated are any such molecules corresponding to any biomarker identified herein, which includes nucleic acid primers/primer sets and probes that are identical to or complementary to all or part of a biomarker, which may include noncoding sequences of the biomarker, as well as coding sequences of the biomarker. In certain aspects, negative and/or positive control nucleic acids, probes, and inhibitors are included in some kit embodiments.

Any embodiment of the disclosure involving specific biomarker by name is contemplated also to cover embodiments involving biomarkers whose sequences are at least 80, 81, 82, 83, 84, 85, 86, 87, 88, 89, 90, 91, 92, 93, 94, 95, 96, 97, 98, 99% identical to the mature sequence of the specified nucleic acid.

Embodiments of the disclosure include kits for analysis of a pathological sample by assessing biomarker profile for a sample comprising, in suitable container means, two or more biomarker probes, wherein the biomarker probes detect one or more of the biomarkers identified herein. The kit can further comprise reagents for labeling nucleic acids in the sample. The kit may also include labeling reagents, including at least one of amine-modified nucleotide, poly(A) polymerase, and poly(A) polymerase buffer. Labeling reagents can include an amine-reactive dye.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Analysis of β-Cells in Type-2 Diabetes

Methods

Histological Assessments

After excision of smaller pieces, pancreas was fixed in 4% paraformaldehyde (Electron Microscopy Sciences 19202, Hatfield, PA, USA) overnight in 4° C., paraffin-embedded, and sectioned at 4 μm thickness. For β-cell area, peroxidase- and hematoxylin staining were performed on deparaffinized sections that were sequentially incubated with rabbit anti-insulin antibody (Cell Signaling Technology C27C9, Danvers, MA, USA, 1:400), then with F(ab')$_2$ conjugates with Biotin-SP (Jackson ImmunoResearch 711-066-152, West Grove, PA, USA, 1:100 for IHC), after which steps the VECTASTAIN ABC Kits (HRP) (Vector Laboratories PK-4000, Burlingame, CA, USA), the DAB substrate Kits (HRP) (Vector Laboratories SK-4100, Burlingame, CA, USA), and Harris Hematoxylin were applied prior mounting the sections with Permount (Fisher SP15-100, Hampton, NH, USA). Morphometric analyses were performed using Image-Pro Plus 5.1 software on the Olympus IX70 inverted tissue culture microscope (Olympus, Center Valley, PA, USA). Imaging and data analysis was performed by two observers in a blinded fashion for the experimental mouse genotype of each section. The islet edges were manually circumscribed using a multichannel image. Insulin- and hematoxylin-positive areas were determined for each islet using pixel thresholding. The β-cell area was then calculated as insulin-positive areas/hematoxylin-positive areas×100%.

Immunofluorescence analysis was performed in Openlab 5.5.0 software on the Leica DM6000 B research microscope. The following antibodies were used: rabbit anti-PFKFB3 (Origene AP15137PU-N, Rockville, MD, USA, 1:100); mouse anti-MCM2 (BD Transduction Laboratories 610700, San Diego, CA, USA, 1:100); rabbit anti-cleaved caspase-3 (Cell Signaling Technology 9664S, Danvers, MA, USA, 1:400); guinea-pig anti-insulin (Abcam ab195956, Cambridge, MA, USA, 1:400); mouse anti-glucagon (Sigma-Aldrich G2654, St. Louis, MO, USA, 1:1000 for IF), mouse anti-c-Myc (Santa Cruz Biotechnology Inc 9E10 sc-40, Dallas, Texas, USA, 1:100); mouse anti-HIF1α (Novus Biologicals NB100-105, Centennial, CO, USA, 1:50). Secondary antibodies were: F(ab')$_2$ conjugates with FITC (Jackson ImmunoResearch 706-096-148, West Grove, PA, USA, 1:200 for IF); F(ab')$_2$ conjugates with Cy3 (Jackson ImmunoResearch 711-166-152, West Grove, PA, USA, 1:200 for IF) and F(ab')$_2$ conjugates with Alexa 647 (Jackson ImmunoResearch 715-606-150, West Grove, PA, USA, 1:100 for IF). The In Situ Cell Death Detection Kit (Roche Diagnostics Corporation 12156792910, Indianapolis, IN, USA) was used for determination of cell death by TUNEL assay. Vectashield with DAPI (Vector Laboratories H1200, Burlingame, CA, USA) was used to mount the slides.

Results

There is a progressive decline in β-cell function in T2D that is partly related to the accumulation of the toxic oligomers of hIAPP [3-5]. hIAPP forms membrane-permeable toxic oligomers that are implicated in misfolded protein stress in T2D. In response to misfolded protein stress by hIAPP, mitochondria in β-cells from humans with T2D acquired a defensive posture through mitochondrial network fragmentation (FIG. 1A) that led to attenuation of mitochondrial respiration of 30% (FIG. 1B). Change in mitochondrial form and function highly resemble neurons exposed to $Ca^{2+}$ toxicity thus reflecting an adaptation to high cytosolic $Ca^{2+}$. Indeed, islets from human IAPP transgenic mice (hTG) demonstrated higher cytosolic $Ca^{2+}$ levels compared to rodent IAPP (rTG) control littermates (FIG. 1C). Oxidative and DNA damage was evident in the subcellular fractions from the islets from donors with T2D relative to non-diabetic (ND) donors, as shown by the increase in the expression of DNA damage response proteins p53, $p21^{WAF1}$ and γH2A.X (FIG. 1D).

Figure 2D:
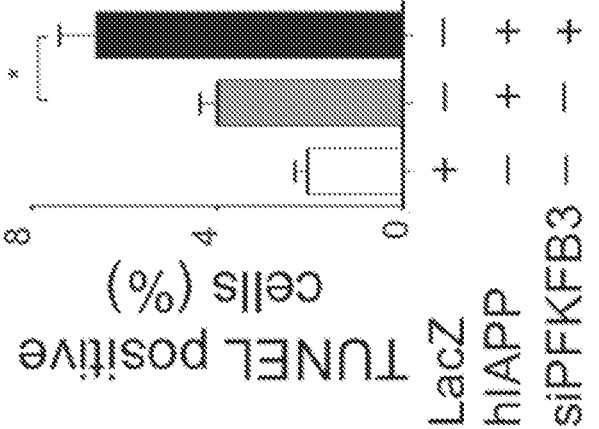
Figure 2C:
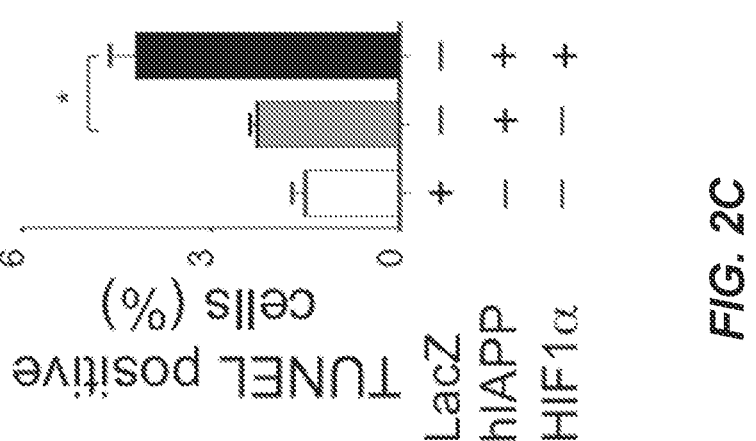

DNA damage response (p53/p21WAF1 axis and accumulation of γH2A.X) document damage of β-cells in T2D and rodent models of T2D. Stress by protein misfolding and the surge of cytosolic $Ca^{2+}$ triggered protective metabolic reprogramming of about one third of all β-cells in T2D (FIG. 2A) by a conserved HIF1α-PFKFB3 injury/repair program. PFKFB3 was identified as accountable for the $Ca^{2+}$ homeostasis, mitochondrial remodeling and metabolome changes in β-cells under stress (FIG. 2B), ultimately leading to survival of damaged β-cells. This was confirmed by in vitro analysis using INS 832/13 cells transfected with adenovirus to express hIAPP in the presence or absence of HIF1α inhibition or PFKFB3. HIF1α inhibition (FIG. 2C) or PFKFB3 post-transcriptional silencing (FIG. 2D) led to increased cell death in hIAPP expressing cells as evidenced by TUNEL assay.

Example 2—Analysis of PFKFB3$^{βKO}$ hIAPP$^{+/-}$+HFD Mice

Methods

Animals

Homozygous hIAPP$^{+/+}$ mice were a gift from Dr. Peter Butler's laboratory and was previously described [15]. A β-cell-specific inducible PFKFB3 knockout mouse model (RIP-CreERT:PFKFB3m) was developed by crossing mice that carry the floxed PFKFB3 gene (JAX Laboratories) with mice that express Cre recombinase under control of the rat insulin promoter (RIP-CreERT). Mice on a homozygous hIAPP$^{+/+}$ background were crossed with either PFKFB3$^{fl/fl}$ or RIP-CreERT mice and then crossed PFKFB3$^{fl/fl}$ hIAPP$^{+/-}$ and PFKFB3$^{fl/fl}$ RIP-CreERT mice together to generate the three experimental genotypes: RIP-CreERT PFKFB3$^{wt/wt}$ hIAPP$^{-/-}$, RIP-CreERT PFKFB3$^{wt/wt}$ hIAPP$^{+/-}$ and RIP-CreERT PFKFB3$^{fl/fl}$ hIAPP$^{+/-}$ hereto referred as PFKFB3$^{WT}$ hIAPP$^{-/-}$, PFKFB3$^{WT}$ hIAPP$^{+/-}$, and PFKFB3$^{βKO}$ hIAPP$^{+/-}$. All experimental groups were subjected to high fat diet. Cre-loxP recombination of the floxed sites in Pfkfb3 was induced by intra-peritoneal tamoxifen injection at the age of 20-27 weeks. The mice were given chow diet for 10 weeks post tamoxifen injection and then all mice were exposed for a high fat diet for another 13 weeks (HFD, Research Diets Inc, New Brunswick, NJ, USA) to induce diabetes in response to hIAPP$^{+/-}$ and HFD, since only male mice homozygous for hIAPP (hIAPP$^{+/+}$) develop diabetes spontaneously [15]. The mice were maintained on a 12 hours day/night cycle at UCLA Institutional Animal Care and Use Committee (ARC) approved mice colony facility. At 30-37 weeks of age, all mice were assigned to receive diet containing high amounts of fat (35% w/w or 60% calories from fat; number D12492). The fat composition of the high-fat diet was 32.2% saturated, 35.9% monounsaturated, and 31.9% polyunsaturated fats. Mice had ad libitum access to diet and water for the duration of the study. Bodyweight and fasting plasma glucose levels were assessed weekly, with additional measures being made on days that included glucose- and insulin tolerance tests (IP-GTT and ITT, respectively).

Insulin and Glucose Tolerance Tests

An intraperitoneal glucose tolerance test (IP-GTT) was performed at 9 and 12 weeks after HFD (19 and 22 weeks post tamoxifen injection). Tail vein blood glucose was collected prior to and 15, 30, 60, 90, 120 minutes post glucose bolus injection. Retro-orbital bleeding was used to collect the blood for the second IP-GTT prior to and 30 minutes after glucose bolus injection. The mice were anesthetized by brief exposure to isoflurane (10 seconds). The blood was collected in EDTA coated microcentrifuge tube and the plasma was obtained by centrifuging the samples for 10 minutes (5000 RCF, 10 min, 4° C.).

Glucose and Insulin Assays

Plasma glucose was determined using the glucose oxidase method and analysed with YSI 2300 STAT PLUS Glucose & L-Lactate Analyzer.

Fasted blood glucose was measured weekly after overnight fasting for 18 hours (after regular change of cages and bedding and withdrawal of food while providing water ad libitum) from a tail drawn blood using a freestyle blood glucose meter (Abbott Diabetes Care Inc, Alameda, CA, USA).

Insulin, c-peptide, and glucagon levels in plasma were determined using Ultrasensitive ELISA for mouse insulin (Mercodia 10-1247-01, Uppsala, Sweden), mouse c-peptide (Crystal Chem 90050, IL, USA), and mouse glucagon (Mercodia 10-1281-01, Uppsala, Sweden).

10 weeks after HFD (19 weeks after tamoxifen injection), intraperitoneal insulin tolerance test (0.75 IU/kg) (Lilly insulin Lispro, LLC, Indianapolis, USA) was performed in conscious mice fasted for 6 hours. Tail vein blood was collected prior to and at 0, 20, 40, 60 minutes post insulin administration for glucose measurement.

Pancreas Perfusion and Isolation

One week following IP-GTT and ITT, mice were euthanized by cervical dislocation. Medial cut was used to open the abdomen and chest cavities, while cut of the right ventricle was followed with a poke of the left ventricle with a needle to inject 10 ml cold phosphate buffered saline (PBS) slowly for perfusion of the pancreas. After perfusion, pancreas was placed in a cold PBS and separated it from other tissue including the surrounding fat. Pancreas was then weighed after absorbing the extra PBS with tissue.

Histological Assessments

After excision of smaller pieces, pancreas was fixed in 4% paraformaldehyde (Electron Microscopy Sciences 19202, Hatfield, PA, USA) overnight in 4° C., paraffin-embedded, and sectioned at 4 μm thickness. For β-cell area, peroxidase- and hematoxylin staining were performed on deparaffinized sections that were sequentially incubated with rabbit anti-insulin antibody (Cell Signaling Technology C27C9, Danvers, MA, USA, 1:400), then with F(ab')$_2$ conjugates with Biotin-SP (Jackson ImmunoResearch 711-066-152, West Grove, PA, USA, 1:100 for IHC), after which steps the VECTASTAIN ABC Kits (HRP) (Vector Laboratories PK-4000, Burlingame, CA, USA), the DAB substrate Kits (HRP) (Vector Laboratories SK-4100, Burlingame, CA, USA), and Harris Hematoxylin were applied prior mounting the sections with Permount (Fisher SP15-100, Hampton, NH, USA). Morphometric analyses were performed using Image-Pro Plus 5.1 software on the Olympus IX70 inverted tissue culture microscope (Olympus, Center Valley, PA, USA). Imaging and data analysis was performed by two observers in a blinded fashion for the experimental mouse genotype of each section. The islet edges were manually circumscribed using a multichannel image. Insulin- and hematoxylin-positive areas were determined for each islet using pixel thresholding. The β-cell area was then calculated as insulin-positive areas/hematoxylin-positive areas×100%.

Immunofluorescence analysis was performed in Openlab 5.5.0 software on the Leica DM6000 B research microscope. The following antibodies were used: rabbit anti-PFKFB3 (Origene AP15137PU-N, Rockville, MD, USA, 1:100); mouse anti-MCM2 (BD Transduction Laboratories 610700, San Diego, CA, USA, 1:100); rabbit anti-cleaved caspase-3 (Cell Signaling Technology 9664S, Danvers, MA, USA, 1:400); guinea-pig anti-insulin (Abcam ab195956, Cambridge, MA, USA, 1:400); mouse anti-glucagon (Sigma-Aldrich G2654, St. Louis, MO, USA, 1:1000 for IF), mouse anti-c-Myc (Santa Cruz Biotechnology Inc 9E10 sc-40, Dallas, Texas, USA, 1:100); mouse anti-HIF1α (Novus Biologicals NB100-105, Centennial, CO, USA, 1:50). Secondary antibodies were: F(ab')$_2$ conjugates with FITC (Jackson ImmunoResearch 706-096-148, West Grove, PA, USA, 1:200 for IF); F(ab')$_2$ conjugates with Cy3 (Jackson ImmunoResearch 711-166-152, West Grove, PA, USA, 1:200 for IF) and F(ab')$_2$ conjugates with Alexa 647 (Jackson ImmunoResearch 715-606-150, West Grove, PA, USA, 1:100 for IF). The In Situ Cell Death Detection Kit (Roche Diagnostics Corporation 12156792910, Indianapolis, IN, USA) was used for determination of cell death by TUNEL assay. Vectashield with DAPI (Vector Laboratories H1200, Burlingame, CA, USA) was used to mount the slides.

Statistical Analyses

Data are presented as an error of the mean (standard error, SEM) for the number of mice indicated. For the IP-GTT and ITT, areas under the curve (AUC) for glucose, insulin, C-peptide and glucagon were calculated using the trapezoidal rule. Mean data were compared between groups by analysis using student's t-test. P values less than 0.05 were considered statistically significant.

Results

Figure 3A:
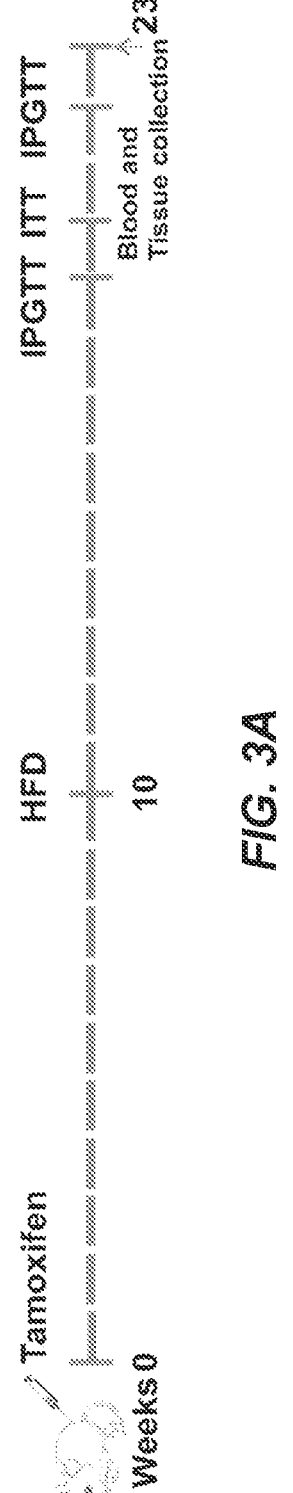
FIGS. 3A and 3B show the experimental protocol and results from validation of PFKFB3$^{βKO}$ on hIAPP+/− mice under high fat diet (HFD).
Figure 3B:
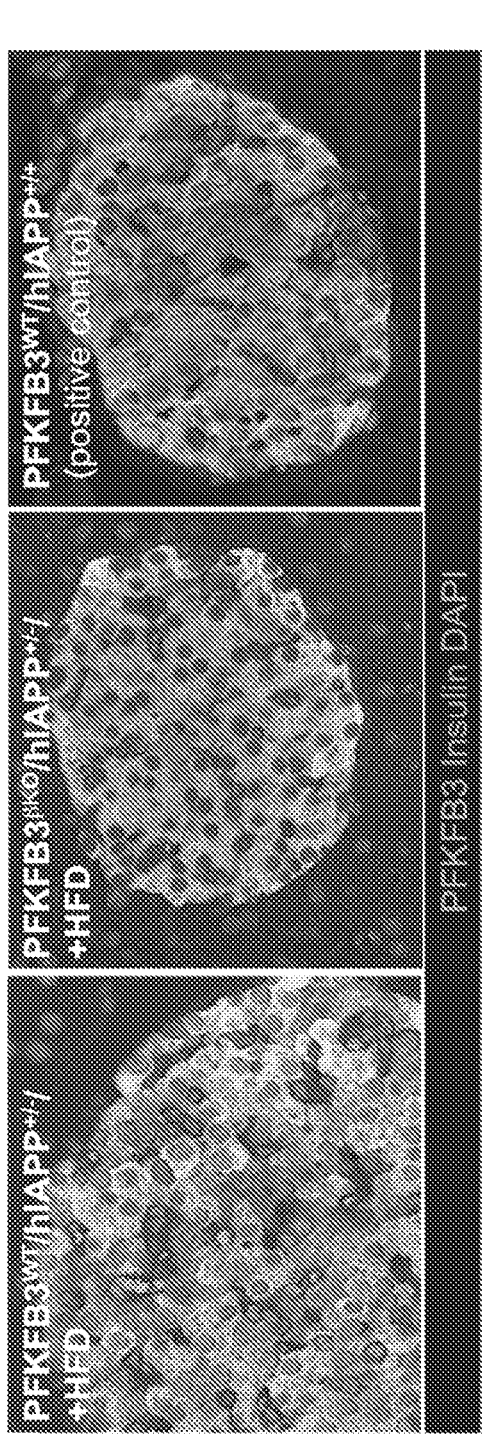

To mimic the impact of insulin resistance, misfolded protein stress, and old age as cumulative risk factors in diabetes and study the role of PFKFB3 in the preservation of damaged β-cells under high diabetogenic stress, mice were generated with β-cell-specific conditional disruption of Pfkfb3 gene on a hIAPP$^{+/-}$ background (see Methods section), exposed to a high fat diet for 13 weeks (PFKFB3$^{βKO}$ hIAPP$^{+/-}$+HFD), and compared to PFKFB3$^{WT}$ hIAPP$^{+/-}$+HFD and PFKFB3$^{WT}$ hIAPP$^{-/-}$+HFD controls (experimental timeline presented in FIG. 3A). Efficient disruption of PFKFB3 expression was confirmed by PFKFB3 immunostaining of the pancreatic sections of the mice from indicated experimental groups and using PFKFB3$^{WT}$ hIAPP$^{+/+}$ as a positive control (FIG. 3B).

Figures 4A, 4B, 4C, 4D:
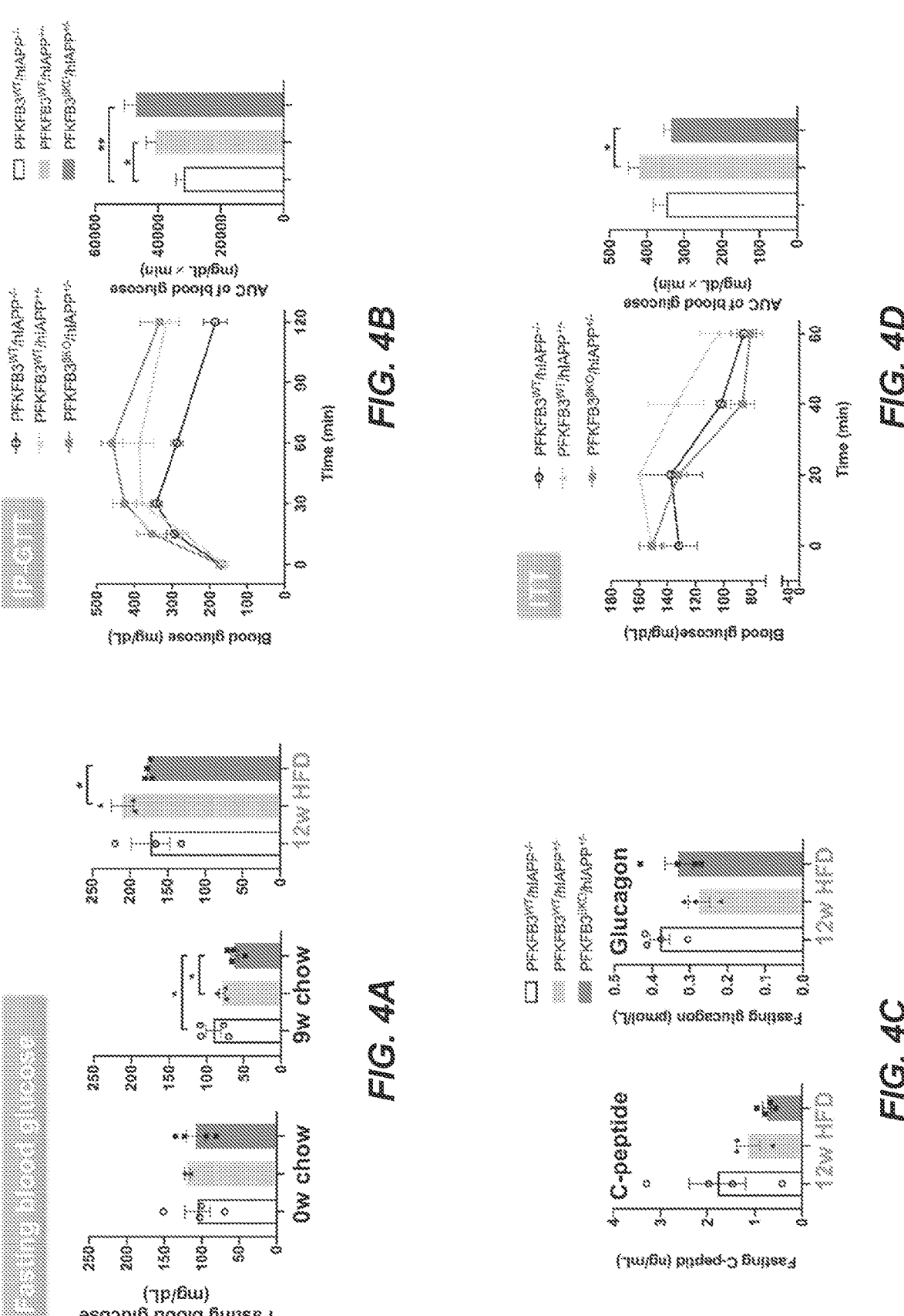
FIGS. 4A-4D show results demonstrating that PFKFB3$^{βKO}$IAPP+/− mice under high fat diet (HFD) demonstrate reduced fasting glucose, increased insulin sensitivity, and comparable impaired glucose tolerance and reduced C-peptide plasma levels to PFKFB3$^{WT}$ IAPP$^{+/-}$ mice.
Figure 5A:
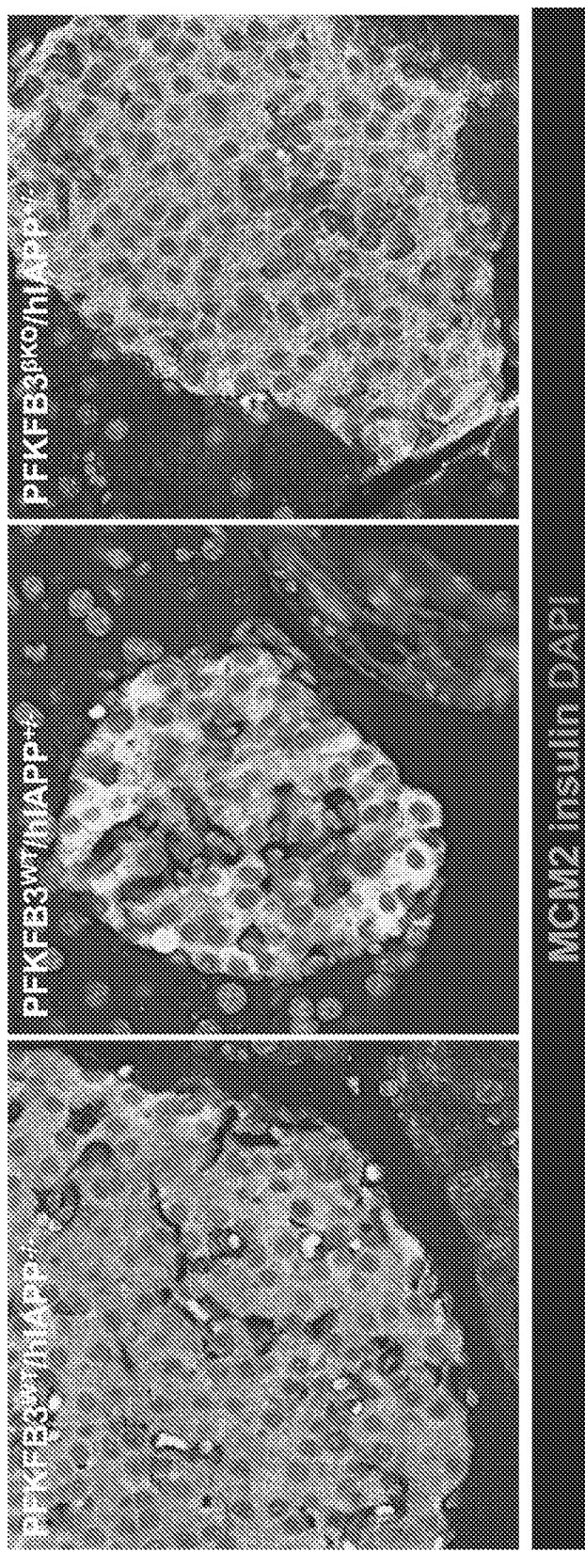
FIGS. 5A-5E show results demonstrating that PFKFB3$^{\beta KO}$ IAPP$^{+/-}$ mice show increased β-cell replication compared to PFKFB3$^{WT}$ IAPP$^{+/-}$ mice.
Figure 5C:
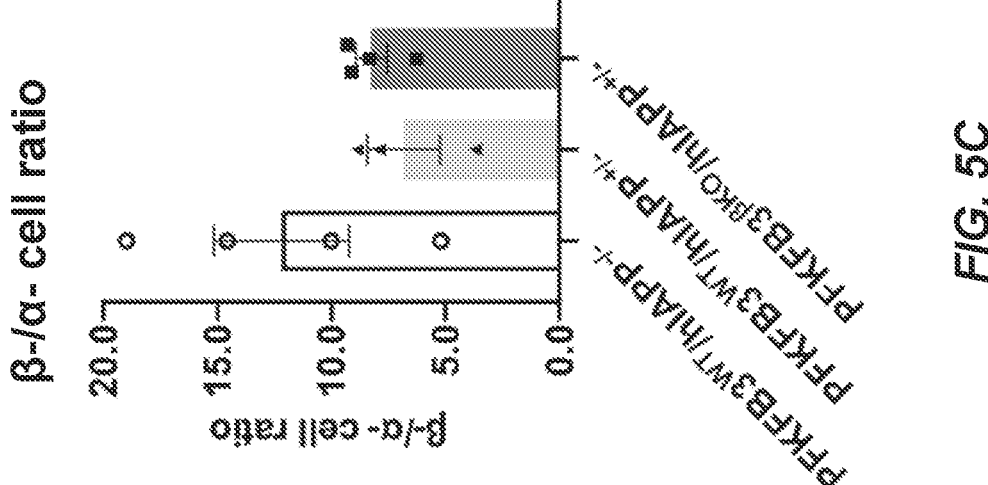
Figure 5B:
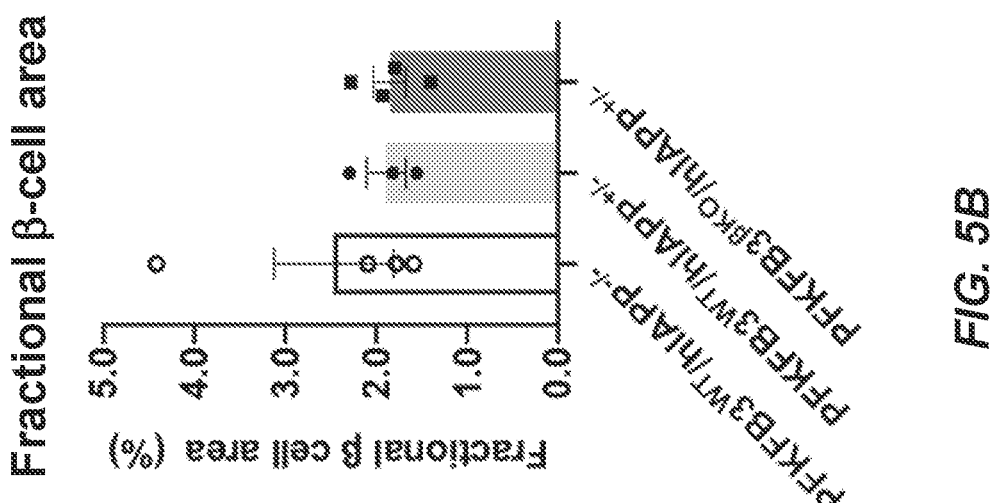

Analysis of the metabolic performance of PFKFB3$^{βKO}$ hIAPP$^{+/-}$+HFD mice revealed lower fasting glucose levels (FIG. 4A), increased insulin sensitivity (FIG. 4D) and increased comparable glucose intolerance (FIG. 4B), relative to PFKFB3$^{WT}$ hIAPP$^{+/-}$+HFD. PFKFB3$^{βKO}$ hIAPP$^{+/-}$+HFD and PFKFB3$^{WT}$ hIAPP$^{+/-}$+HFD mice both had reduced C-peptide levels when compared to PFKFB3$^{WT}$ hIAPP$^{-/-}$+HFD controls (FIG. 4C). These results together with increased insulin sensitivity suggested impaired insulin secretion in PFKFB3$^{βKO}$ hIAPP$^{+/-}$+HFD mice, potentially due to a failure to expand the β-cell mass under diabetogenic stress in the absence of PFKFB3. However, β-cell fractional area and mass were unaltered among the experimental groups (FIG. 5B).

Figure 5E:
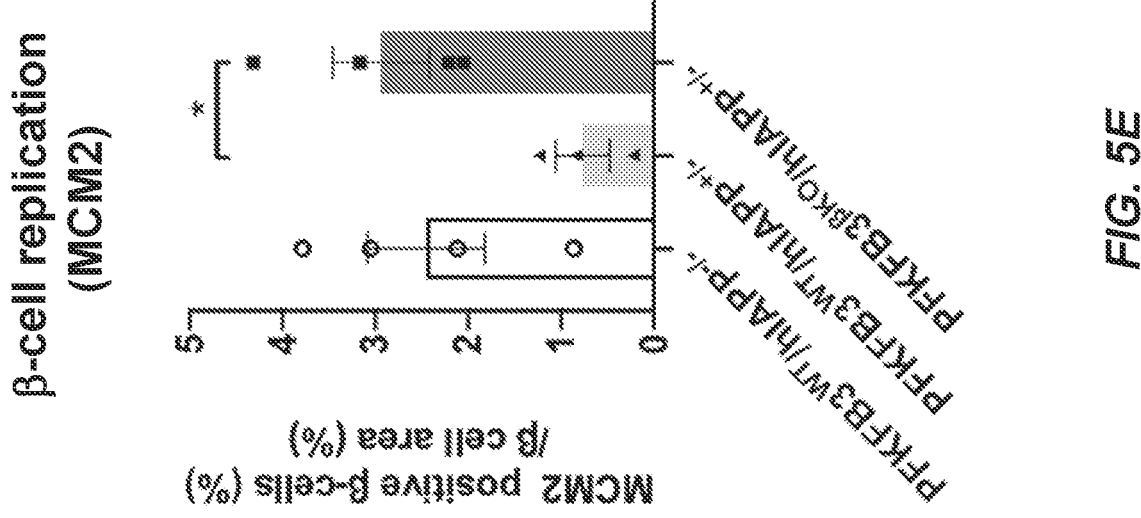
Figure 5D:
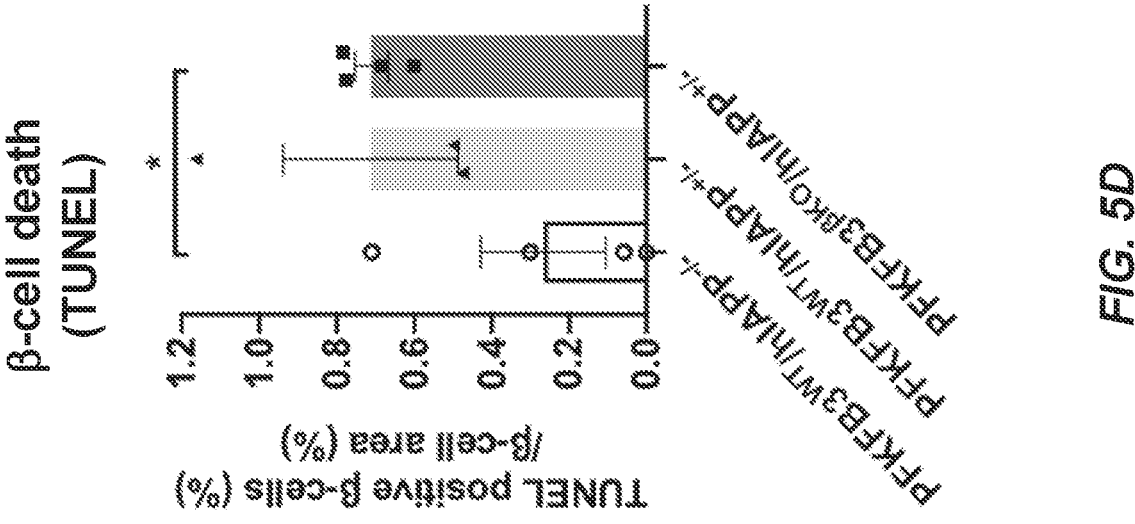

To investigate growth dynamics that ultimately led to comparable β-cell mass between PFKFB3$^{βKO}$ hIAPP$^{+/-}$+HFD- and PFKFB3$^{WT}$ hIAPP$^{+/-}$+HFD mice, TUNEL staining was performed to determine β-cell death and MCM2 immunostaining to determine β-cell replication. According to the TUNEL analysis, β-cell death was increased in the PFKFB3$^{βKO}$ hIAPP$^{+/-}$+HFD mice relative to PFKFB3$^{WT}$ hIAPP$^{-/-}$+HFD controls while it was comparable to PFKFB3$^{WT}$ hIAPP$^{+/-}$+HFD mice (FIG. 5D). Cell death was mainly attributable to β-cells since β-/α cell ratio tended to be reduced in both PFKFB3$^{βKO}$ hIAPP$^{+/-}$+HFD- and PFKFB3$^{WT}$ hIAPP$^{+/-}$+HFD mice (FIG. 5C). β-cells from PFKFB3$^{βKO}$ hIAPP$^{+/-}$+HFD mice exhibited a three-fold increase in MCM2 labeling (*p<0.05), indicating increased β-cell replication compared to hIAPP$^{+/-}$+HFD mice and similar to PFKFB3$^{WT}$ IAPP$^{-/-}$+HFD controls (FIGS. 5A and 5E). In spite of increase in both cell death and β-cell replication in PFKFB3$^{βKO}$ hIAPP$^{+/-}$+HFD mice, β-cell fractional area was comparable in all three groups (FIG. 5B).

Figure 6A:
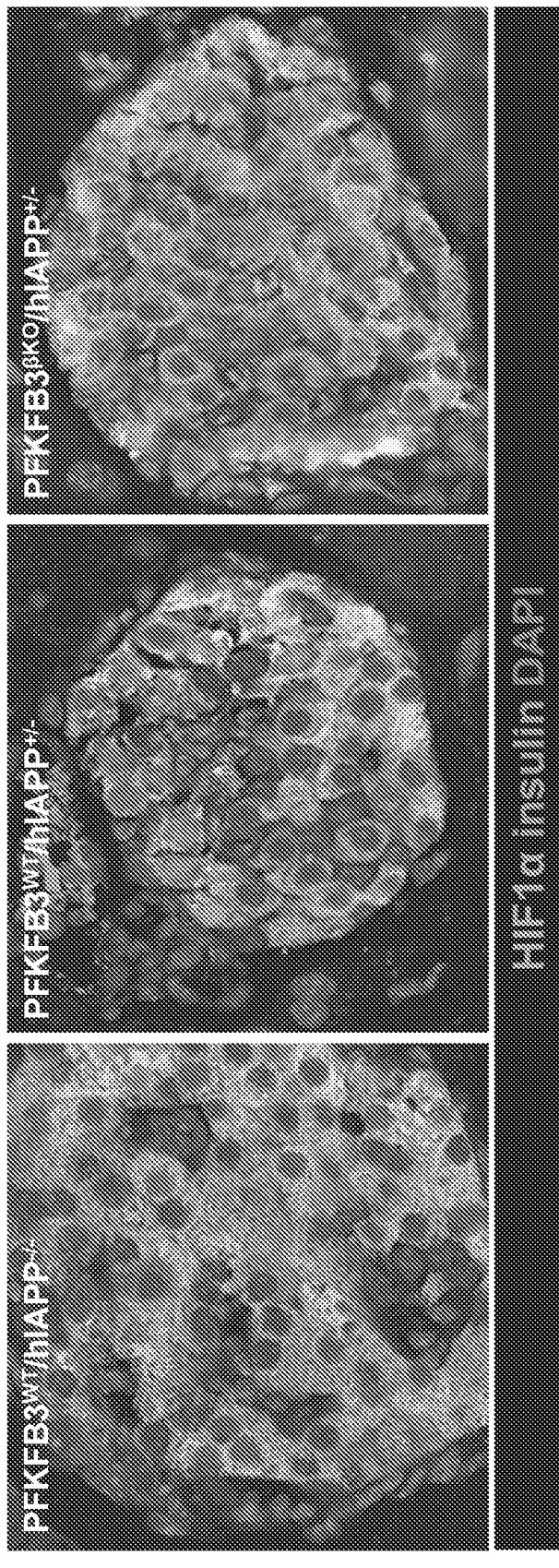
FIGS. 6A-6C show results demonstrating that PFKFB3$^{\beta KO}$ IAPP$^{+/-}$ mice show remaining HIF1α immunopositivity.
Figure 6C:
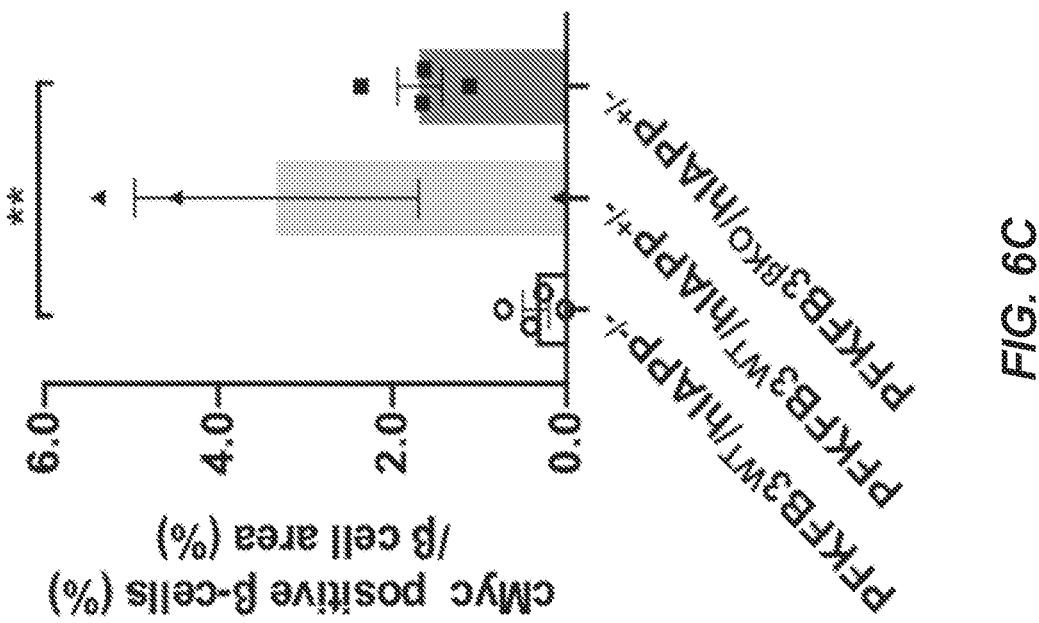
Figure 6B:
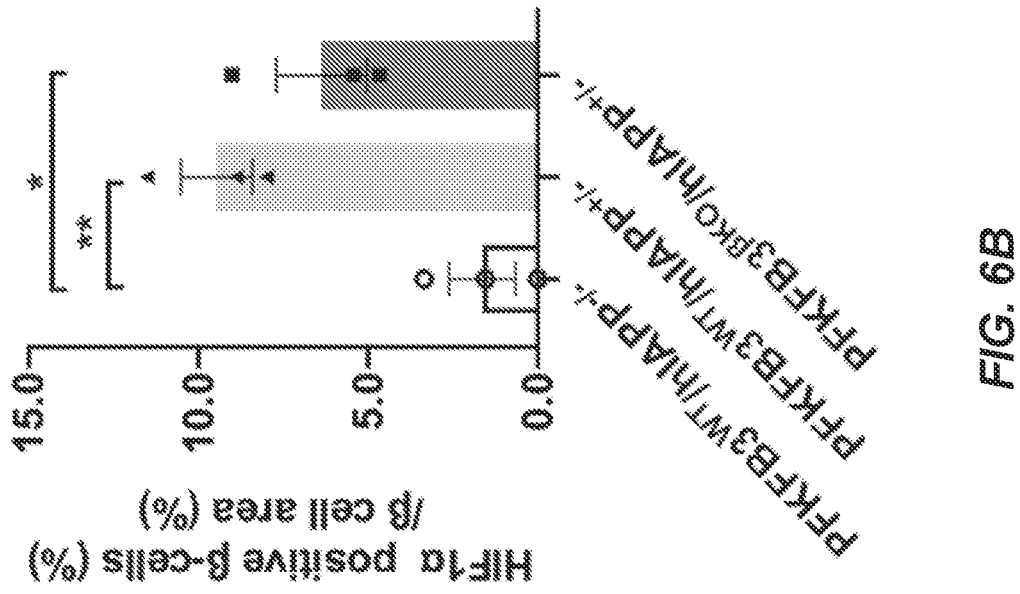

To clarify the failure to recover β-cell function in spite of recovery of β-cell mass, HIF1α immunostaining was performed in the pancreatic sections of PFKFB3$^{βKO}$ hIAPP$^{+/-}$+HFD mice and found that about 10% of all β-cells remain positive for HIF1α, indicating a fraction of HIF1α positive—but PFKFB3 negative β-cells that remain after PFKFB3 genetic depletion (FIGS. 6A and 6B). Remaining HIF1α immunostaining indicated ongoing damage (stress) that is responsible for failure to recover β-cell function. To determine whether there was ongoing damage in β-cells, a marker of β-cell damage, truncated c-myc called Myc-nick [14] was used. Albeit reduced to half, Myc-Nick expression was still sustained in PFKFB3$^{βKO}$ hIAPP$^{+/-}$+HFD mice (FIG. 6C). Together with sustained HIF1α-positive β-cell fraction, Myc-nick upregulation indicated a fraction of PFKFB3$^{βKO}$ cells that still have not recovered complete function despite PFKFB3 knockout. This indicated a role of HIF1α in loss of β-cell function even in the absence of PFKFB3.

Example 3—Analysis of RNA-Seq Data from Type-2 Diabetes Patients

Figure 7A:
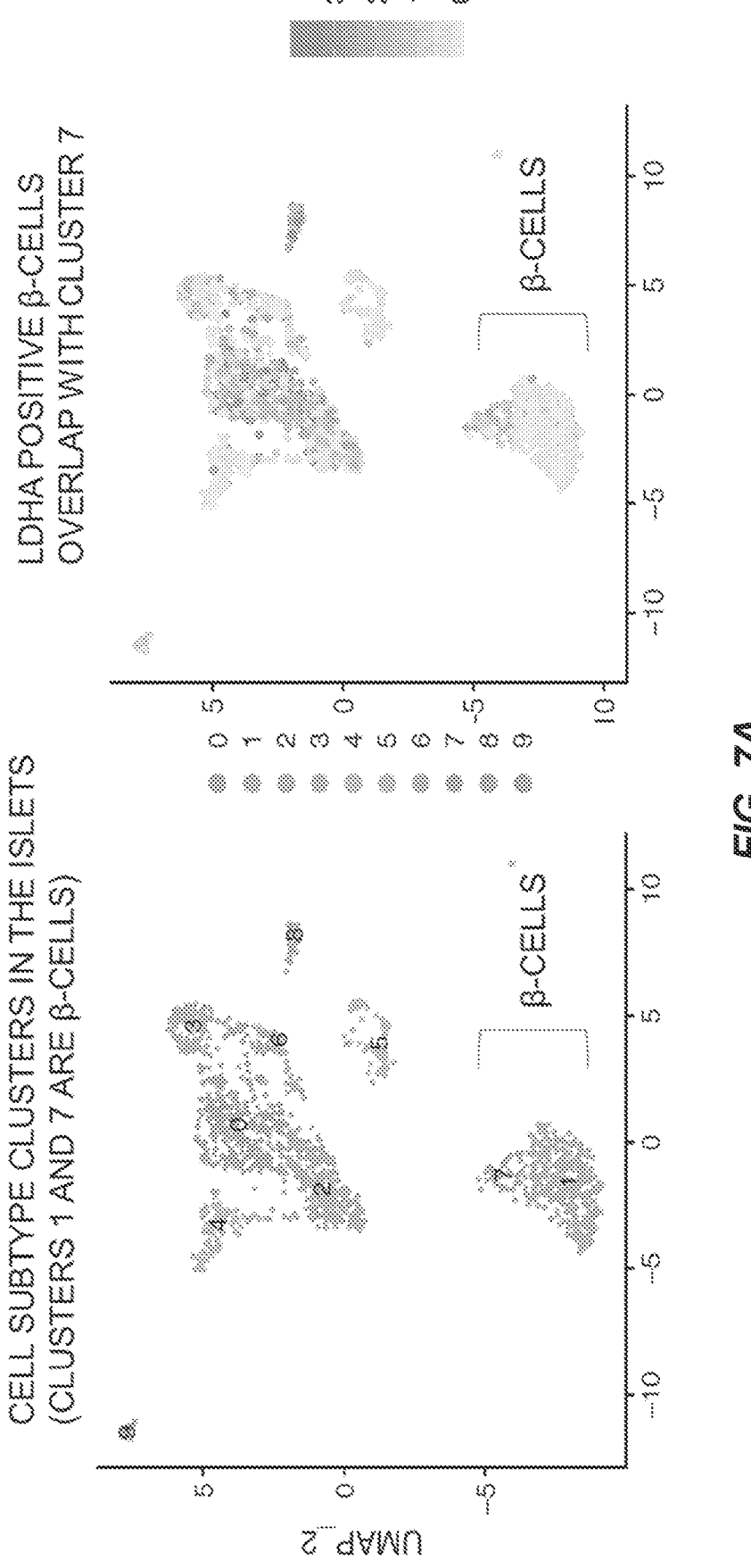

To characterize the potential contribution of HIF1α-positive β-cells to loss of function, published RNA Seq data from human T2D was analyzed [1]. β-cells from healthy and T2D donors were reclustered (umap cluster) and annotated to the specific cell types based on the gene markers such as insulin (INS) for β-cells (umap_celltype, FIG. 7A). β-cells were then separated into those from healthy and T2D conditions (umap_disease, not shown). For each condition, and for each gene (e.g LDHA as an example), cells were split into gene (e.g., LDHA) positive- and gene (e.g., LDHA) negative cells and differential expression analysis was performed between the two groups. LDHA expression was used to differentiate healthy from stressed β-cells since LDHA is transcriptional target of HIF1α that leads to the final step of aerobic glycolysis and metabolic remodeling of stressed β-cells. LDHA-positive cells overlapped with cluster 7 delineated β-cell subpopulation and co-aggregated with genes relevant for metabolism, Ca$^{2+}$ homeostasis and ion channel—as well as insulin secretion regulation (FIGS. 7A and 7B). These results pinpointed that, similar to the mouse model of diabetes, in humans with T2D a fraction of β-cells (LDHA-positive cells within the cluster 7) shows a genetic signature that partly explains loss of β-cell function.

Example 4—Analysis of the Role of HIF1α-PFKFB3 Signaling in Diabetogenic Stress Methods Animals Homozygous hIAPP$^{+/+}$ mouse was a gift from Dr. Peter Butler's laboratory and was previously described (Janson et al., 1996). A β-cell-specific inducible PFKFB3 knockout mouse model (RIP-CreERT:PFKFB3$^{fl/fl}$) was generated by crossing mice that carry the floxed Pfkfb3 gene (JAX Laboratories) with mice that express Cre recombinase under control of the rat insulin promoter (RIP-CreERT). Mice on a homozygous hIAPP$^{+/+}$ background were crossed with either PFKFB3$^{fl/f}$ or RIP-CreERT mice and then PFKFB3$^{fl/fl}$ hIAPP$^{+/-}$ and PFKFB3$^{fl/fl}$ RIP-CreERT mice were crossed together to generate the three experimental genotypes: RIP-CreERT PFKFB3$^{fl/fl}$ hIAPP$^{-/-}$, RIP-CreERT PFKFB3$^{wt/wt}$ hIAPP$^{+/-}$ and RIP-CreERT PFKFB3$^{fl/fl}$ hIAPP$^{+/-}$ hereto referred as PFKFB3$^{WT}$ hIAPP$^{-/-}$, PFKFB3$^{WT}$ hIAPP$^{+/-}$ (PFKFB3$^{WT}$ diabetogenic stress, or PFKFB3$^{WT}$ DS), and PFKFB3$^{βKO}$ hIAPP$^{+/-}$ (PFKFB3$^{βKO}$ DS) respectively. Cre-loxP recombination of the floxed sites in Pfkfb3 was induced by intra-peritoneal tamoxifen injection at the age of 20-27 weeks. The mice were under a chow diet for 10 weeks post tamoxifen injection and then under high fat diet for another 13 weeks (HFD, Research Diets Inc, New Brunswick, NJ, USA) to induce diabetes in response to hIAPP$^{+/-}$ and HFD, since only male mice homozygous for hIAPP (hIAPP$^{+/+}$) develop diabetes spontaneously (Janson et al., 1996). The mice were maintained on a 12 hours day/night cycle at UCLA Institutional Animal Care and Use Committee (ARC) approved mice colony facility. At 30-37 weeks of age, all mice were assigned to receive a diet containing high fat (35% w/w or 60% calories from fat; D12492). The fat composition of the high-fat diet was 32.2% saturated, 35.9% monounsaturated, and 31.9% polyunsaturated fats. Mice had ad libitum access to diet and water for the duration of the study. Body weight and fasting blood glucose levels were assessed weekly, with additional measures being made on days that included glucose- and insulin tolerance tests (IP-GTT and ITT, respectively).

Insulin and Glucose Tolerance Tests

Intra-peritoneal glucose tolerance test (IP-GTT) was performed at 9 and 12 weeks after HFD (19 and 22 weeks post tamoxifen injection). Tail vein blood glucose was collected prior to and 15, 30, 60, 90, 120 minutes post glucose bolus injection. Retro-orbital bleeding was used to collect the blood for the second IP-GTT prior to and 30 minutes after glucose bolus injection. The mice were anesthetized by brief exposure to isoflurane (10 seconds). The blood was collected in EDTA coated microcentrifuge tube and the plasma was obtained by centrifuging the samples for 10 minutes (5000 RCF, 10 min, 4° C.).

Glucose and Insulin Assays

Fasted blood glucose was measured weekly after overnight fasting for 18 hours (after the regular change of cages and bedding and withdrawal of food while providing water ad libitum) from a tail drawn blood using a freestyle blood glucose meter (Abbott Diabetes Care Inc, Alameda, CA, USA). When blood glucose exceeded the detection range of the blood glucose meter, plasma glucose was determined using the glucose oxidase method and analyzed with YSI 2300 STAT PLUS Glucose & L-Lactate Analyzer.

Insulin, C-peptide, and glucagon levels in plasma were determined using Ultrasensitive ELISA for mouse insulin (Mercodia 10-1247-01, Uppsala, Sweden), mouse C-peptide (Crystal Chem 90050, IL, USA), and mouse glucagon (Mercodia 10-1281-01, Uppsala, Sweden).

10 weeks after HFD (19 weeks after tamoxifen injection), intraperitoneal insulin tolerance test (0.75 IU/kg) (Lilly insulin Lispro, LLC, Indianapolis, USA) was performed in conscious mice fasted for 6 hours. Tail vein blood was collected prior to and at 0, 20, 40, 60 minutes post insulin administration for glucose measurement.

Pancreas Perfusion and Isolation

One week following IP-GTT and ITT, mice were euthanized by cervical dislocation. Medial cut was used to open the abdomen and chest cavities, while cut of the right ventricle was followed with a poke of the left ventricle with a needle to inject 10 ml cold phosphate buffered saline (PBS) slowly for perfusion of the pancreas. After perfusion, pancreas was placed in a cold PBS and separated from other tissue including the surrounding fat. Pancreas was then weighed after absorbing the extra PBS with tissue.

Histological Assessments

After excision of smaller pieces, pancreas was fixed in 4% paraformaldehyde (Electron Microscopy Sciences 19202, Hatfield, PA, USA) overnight at 4° C., paraffin-embedded, and sectioned at 4 μm thickness. For β-cell area, peroxidase- and hematoxylin staining were performed on deparaffinized sections that were sequentially incubated with rabbit anti-insulin antibody (Cell Signaling Technology C27C9, Danvers, MA, USA, 1:400), then with F(ab')$_2$ conjugates with Biotin-SP (Jackson ImmunoResearch 711-066-152, West Grove, PA, USA, 1:100 for IHC), after which steps the VECTASTAIN ABC Kits (HRP) (Vector Laboratories PK-4000, Burlingame, CA, USA), the DAB substrate Kits (HRP) (Vector Laboratories SK-4100, Burlingame, CA, USA), and Harris Hematoxylin were applied prior to mounting the sections with Permount (Fisher SP15-100, Hampton, NH, USA). Morphometric analyses were performed using Image-Pro Plus 5.1 software on the Olympus IX70 inverted tissue culture microscope (Olympus, Center Valley, PA, USA). Imaging and data analysis was performed by two observers in a blinded fashion for the experimental mouse genotype of each section. The islet edges were manually circumscribed using a multichannel image. Insulin- and hematoxylin-positive areas were determined for each islet using pixel thresholding. The β-cell area was then calculated as insulin-positive areas/hematoxylin-positive areas*100%.

Immunofluorescence analysis was performed in Openlab 5.5.0 software on the Leica DM6000 B research microscope. The following antibodies were used: rabbit anti-PFKFB3 (Abcam ab181861, Cambridge, MA, USA, 1:100); mouse anti-MCM2 (BD Transduction Laboratories 610700, San Diego, CA, USA, 1:100); rabbit anti-cleaved caspase-3 (Cell Signaling Technology 9664S, Danvers, MA, USA, 1:400); guinea-pig anti-insulin (Abcam ab195956, Cambridge, MA, USA, 1:400); mouse anti-glucagon (Sigma-Aldrich G2654, St. Louis, MO, USA, 1:1000), mouse anti-c-Myc (Santa Cruz Biotechnology Inc 9E10 sc-40, Dallas, Texas, USA, 1:100); mouse anti-HIF1α (Novus Biologicals NB100-105, Centennial, CO, USA, 1:50). Secondary antibodies were: F(ab')2 conjugates with FITC Donkey Anti-Guinea Pig IgG (H+L) (Jackson ImmunoResearch 706-096-148, West Grove, PA, USA, 1:200 for IF); F(ab')2 conjugates with Cy3 Donkey Anti-Rabbit IgG (H+L) (Jackson ImmunoResearch 711-166-152, West Grove, PA, USA, 1:200 for IF; F(ab')2 conjugates with Cy3 Donkey Anti-Mouse IgG (H+L) (Jackson ImmunoResearch 711-165-151, West Grove, PA, USA, 1:200 for IF) and F(ab')2 conjugates with Alexa 647 Donkey Anti-Mouse IgG (H+L) (Jackson ImmunoResearch 715-606-150, West Grove, PA, USA, 1:100 for IF). The In Situ Cell Death Detection Kit (Roche Diagnostics Corporation 12156792910, Indianapolis, IN, USA) was used for the determination of cell death by TUNEL assay. Vectashield with DAPI (Vector Laboratories H1200, Burlingame, CA, USA) was used to mount the slides.

Single-Cell RNA Sequencing Data Analysis

The single-cell RNA-seq dataset was obtained from GEO accession GSE124742, in which the healthy and type 2 diabetes cells were used. To identify different cell types and find signature genes for each cell type, the R package Seurat (version 3.1.2) was used to analyze the expression matrix. Cells with less than 100 genes and 500 UMIs detected were removed from further analysis. Seurat function Normalize-Data was used to normalize the raw counts. Variable genes were identified using the FindVariableGenes function. The Seurat ScaleData function was used to scale and center expression values in the dataset for dimensional reduction. Default parameters were used in the Seurat functions above. Principal component analysis (PCA) and uniform manifold approximation and projection (UMAP) were used to reduce the dimensions of the data, and the first two dimensions were used in plots. The FindClusters function was later used to cluster the cells. The FindAllMarkers function was used to determine the marker genes for each cluster, which were then used to define the cell types. Differential expression analysis between two group of cells was carried out using the FindMarkers function. The Wilcoxon rank sum test was performed in the differential analysis, and the Benjamini-Hochberg procedure was applied to adjust the false discovery rate.

Statistical Analyses

Data are presented as an error of the mean (standard error, SEM) for the number of mice indicated. For the IP-GTT and ITT, areas under the curve (AUC) for glucose, insulin, C-peptide and glucagon were calculated using the trapezoidal rule. Mean data were compared between groups by analysis using student's t-test. P values less than 0.05 were considered significant.

Results

To study and dissect the role of PFKFB3 from HIF1α in the survival of damaged β-cells under diabetogenic stress in vivo, mice were generated with β-cell-specific conditional disruption of Pfkfb3 gene on a hIAPP$^{+/-}$ background and were exposed to a high fat diet for 13 weeks (PFKFB3$^{\beta KO}$ hIAPP$^{+/-}$+HFD). Diabetogenic stress was deemed high since it involved insulin resistance (obesity) and exposure to misfolded proteins through hIAPP$^{+/-}$ expression, both impacted through high fat diet as well as old age all together known as cumulative risk factors in diabetes [16-18].

Figure 16C:
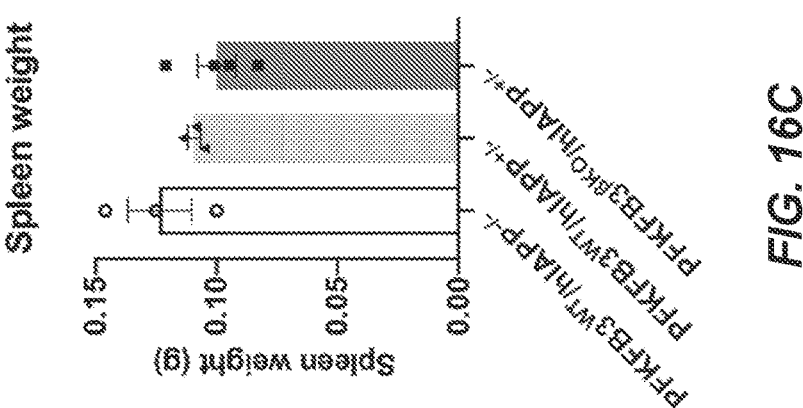
FIGS. 16A-16C show results demonstrating that organ weight among experimental groups during the course of experiment was unaffected. Weight (g) in indicated experimental groups of pancreas (FIG. 16A), liver (FIG. 16B), and spleen (FIG. 16C).
Figure 16B:
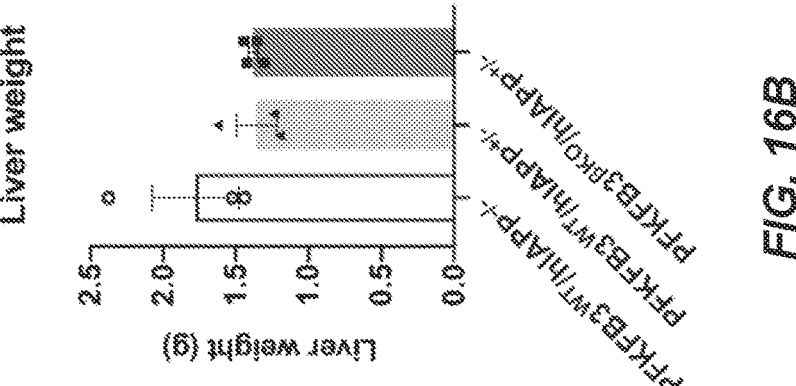
Figure 16A:
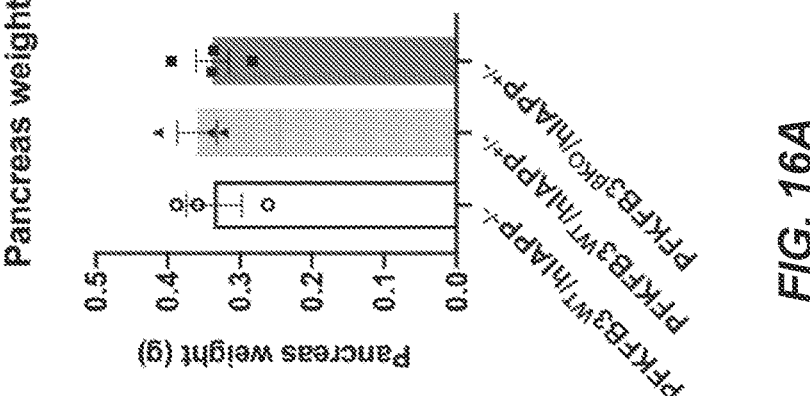
Figures 17A, 17B, 17C:
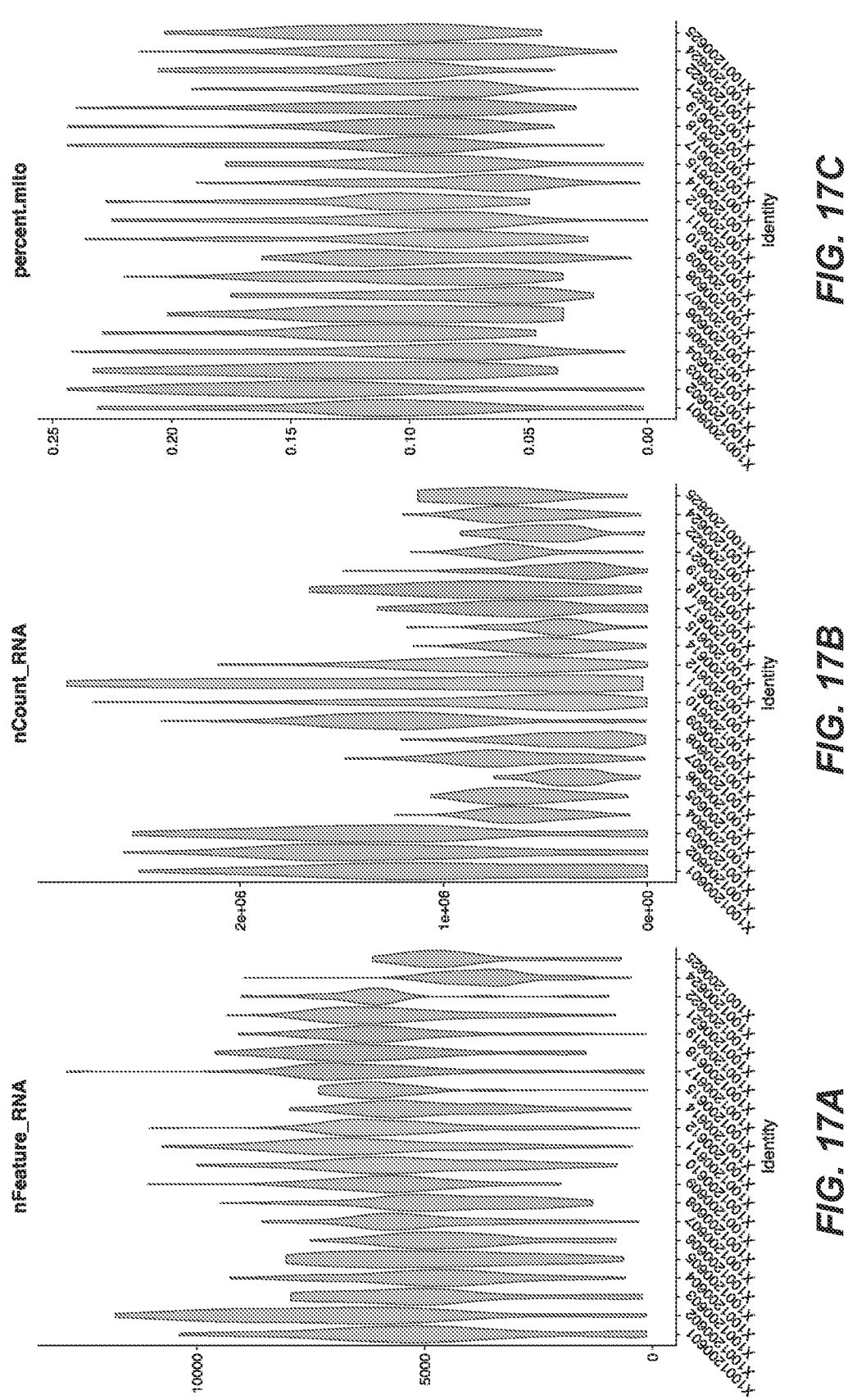
FIGS. 17A-17C show violin plots showing the distribution of number of genes (FIG. 17A), number of transcripts (FIG. 17B) and percentage of mitochondrial expression (FIG. 17C) in the cells from each donor.
Figures 18A, 18B, 18C:
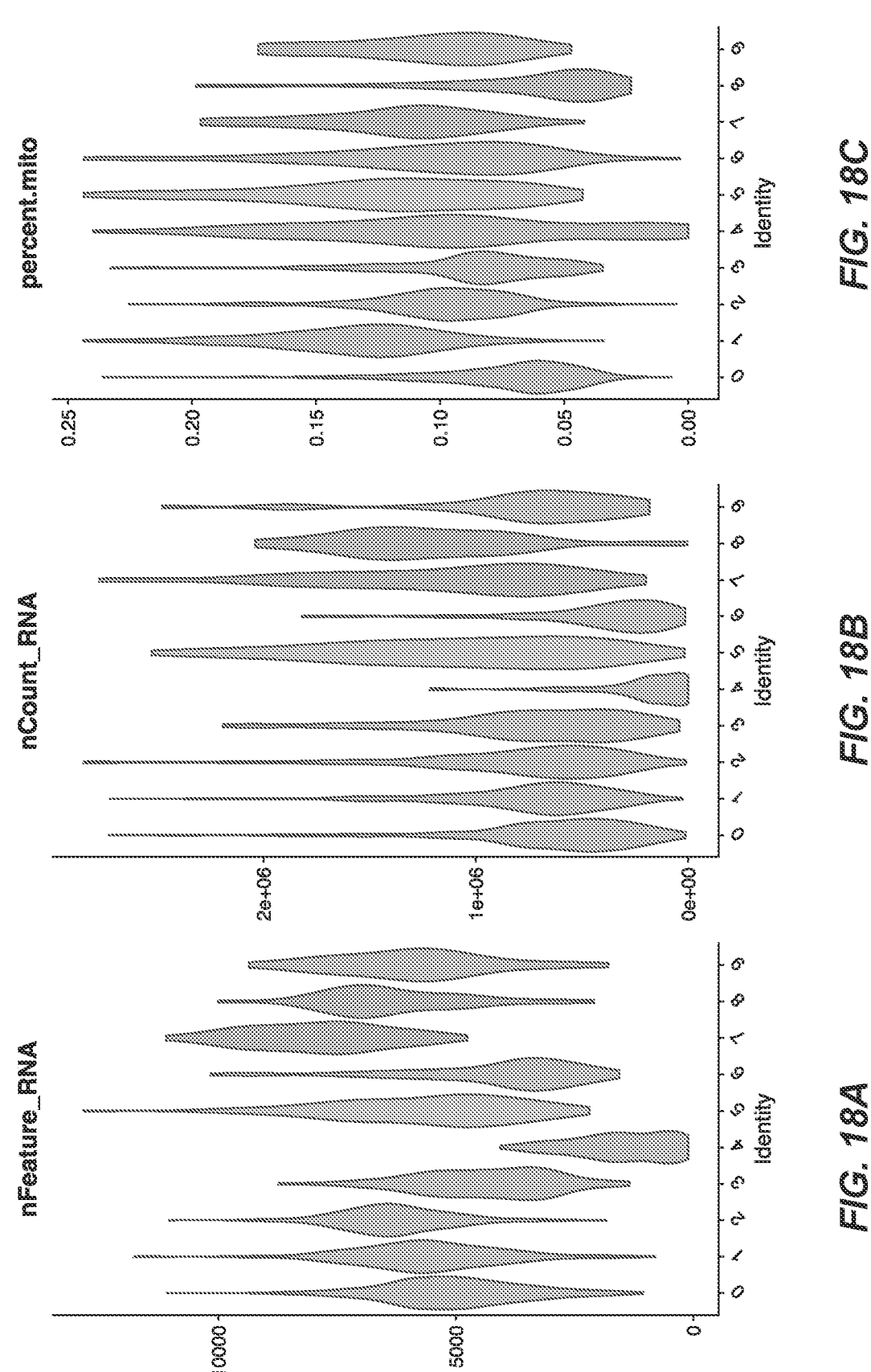
FIGS. 18A-18C show violin plots showing the distribution of number of genes (FIG. 18A) number of transcripts (FIG. 18B) and percentage of mitochondrial expression (FIG. 18C) in the cells from each cluster.

PFKFB3$^{fl/fl}$ hIAPP$^{+/-}$ mice were born at the expected Mendelian ratio. From one week before the monitoring of mice up to the end of the experiment, there was no difference in bodyweight among the different experimental groups (FIGS. 15A-15D). No difference was observed in the pancreas weight, but both spleen and liver showed lower weights in PFKFB3$^{WT}$ hIAPP$^{+/-}$+HFD mice and PFKFB3$^{\beta KO}$ hIAPP$^{+/-}$+HFD mice compared to PFKFB3$^{WT}$ hIAPP$^{-/-}$+HFD controls although not reaching a significant difference (FIGS. 16A-16C).

Figure 8A:
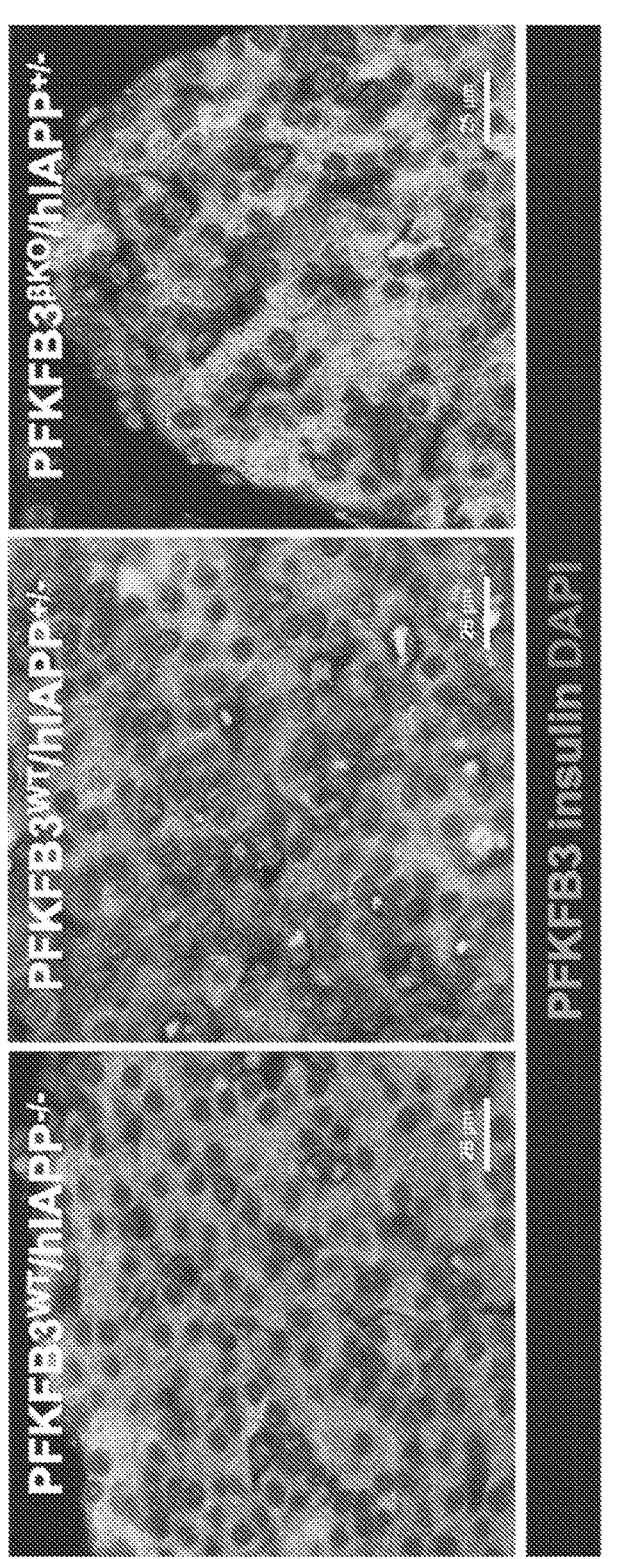
FIGS. 8A-8D show results demonstrating that HIF1α is upregulated in PFKFB3$^{\beta KO}$ hIAPP$^{+/-}$ mice under high fat diet (HFD).
Figure 8B:
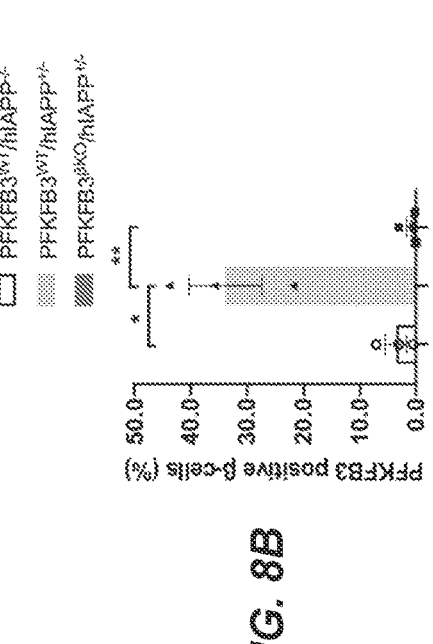

PFKFB3$^{\beta KO}$ hIAPP$^{+/-}$+HFD mice were compared to PFKFB3$^{WT}$ hIAPP$^{+/-}$+HFD and PFKFB3$^{WT}$ hIAPP$^{-/-}$+HFD controls. Efficient disruption of PFKFB3 expression was confirmed by PFKFB3 immunostaining of the pancreatic sections of the PFKFB3$^{\beta KO}$ hIAPP$^{+/-}$+HFD mice using PFKFB3$^{WT}$ hIAPP$^{+/+}$ as a positive control (FIG. 8A). Diabetogenic stress led to 33.9±6.4% PFKFB3 immunolabeling of β-cells in PFKFB3$^{WT}$ hIAPP$^{+/-}$+HFD mice (p<0.05), similar to that previously reported for humans with T2D [18]. PFKFB3 immunolabeling of β-cells from PFKFB3$^{WT}$ hIAPP$^{-/-}$+HFD treated mice was 3.7±1.9%, while in PFKFB3$^{\beta KO}$ hIAPP$^{+/-}$+HFD mice it was successfully abolished and accounted for 1.0±0.8% (FIGS. 8A and 8B).

To establish if PFKFB3 in this model is linked to HIF1α expression, pancreatic sections from all experimental groups were immunostained with HIF1α antibody. HIF1α expression increased to 18.4±4.2% in β-cells from PFKFB3$^{WT}$ hIAPP$^{+/-}$+HFD mice compared to PFKFB3$^{WT}$ hIAPP$^{-/-}$+HFD control (*p<0.05). In PFKFB3$^{\beta KO}$ hIAPP$^{+/-}$+HFD mice, 14.2±3.8% of all β-cells (FIGS. 8C and 8D) continued showing HIF1α immunopositive cytoplasm and nucleus. This clearly indicated that PFKFB3 knockout triggered a compensatory HIF1α expression in response to stress.

Figure 9B:
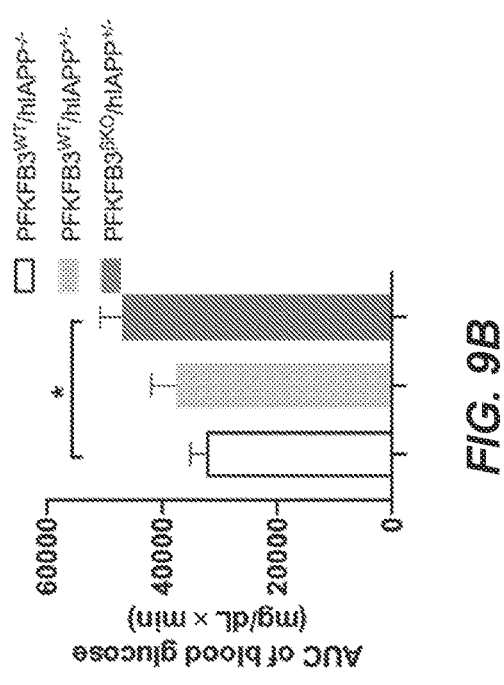
Figure 9A:
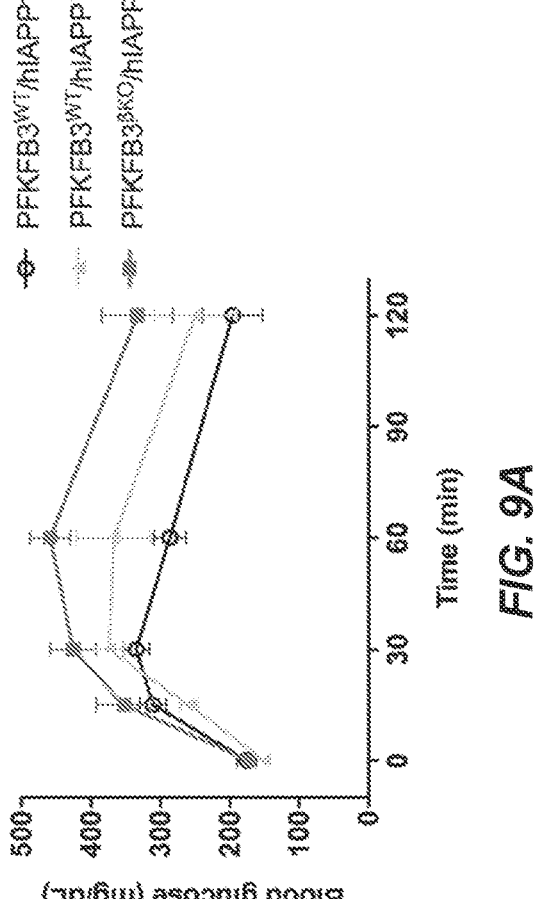
Figure 9C:
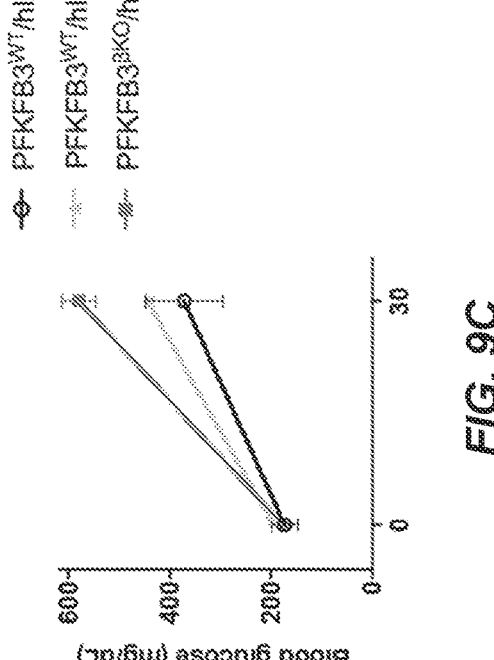
Figure 9E:
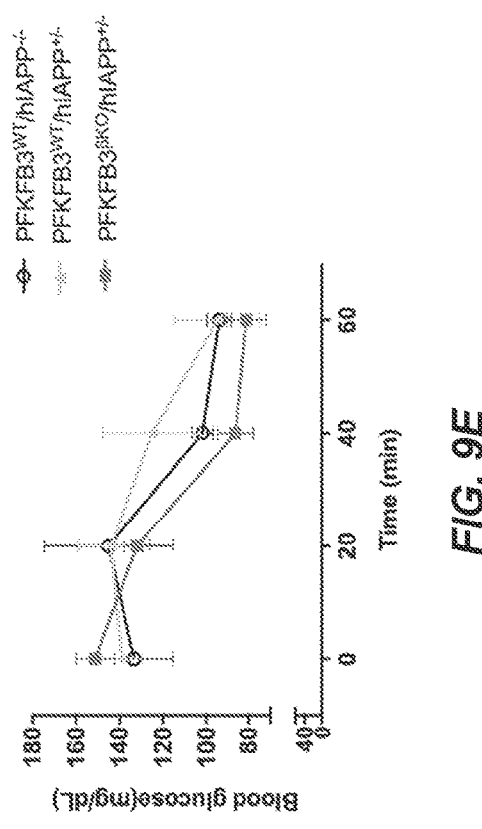
Figure 9D:
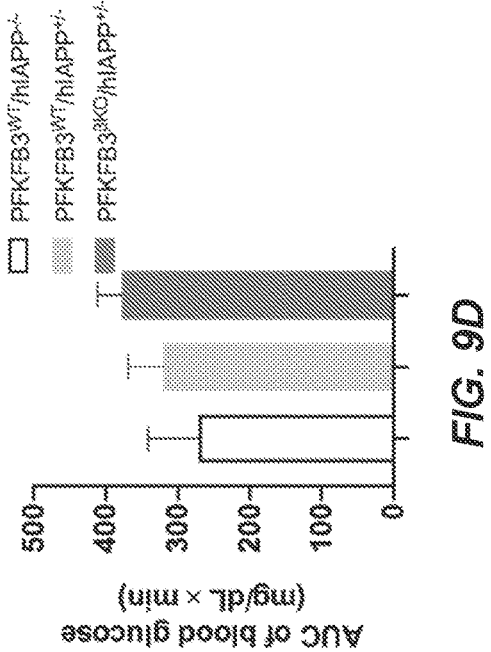
Figure 9F:
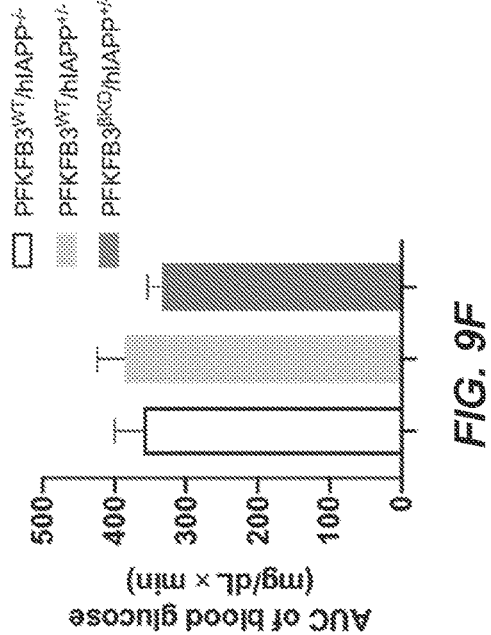

Analysis of the metabolic performance of PFKFB3$^{\beta KO}$ hIAPP$^{+/-}$+HFD mice revealed increased glucose intolerance at both 9 (*p<0.05, n=4) and 12 weeks after onset of high fat diet (FIGS. 9A-9D). Insulin tolerance test indicated higher insulin sensitivity in PFKFB3$^{\beta KO}$ hIAPP$^{+/-}$+HFD mice and although not significant but lower fasting glucose levels, a difference that became diminished among the experimental groups at the later time points. (FIGS. 9C and 9D). Plasma insulin levels mirrored C-peptide levels and were lower in PFKFB3$^{\beta KO}$ hIAPP$^{+/-}$+HFD and PFKFB3$^{WT}$ hIAPP$^{+/-}$+HFD compared to PFKFB3$^{WT}$ hIAPP$^{-/-}$+HFD controls (p<0.05) (FIGS. 9G-2H). Interestingly, although plasma insulin was low for PFKFB3$^{\beta KO}$ hIAPP$^{+/-}$+HFD and PFKFB3$^{WT}$ hIAPP$^{+/-}$+HFD mice, they later had much higher plasma glucagon levels while PFKFB3$^{\beta KO}$ hIAPP$^{+/-}$+HFD demonstrated a sharp reduction in comparison to PFKFB3$^{WT}$ hIAPP$^{+/-}$+HFD and the same levels as seen in PFKFB3$^{WT}$ hIAPP$^{-/-}$+HFD controls (FIG. 9I). These results together with increased insulin sensitivity suggested impaired insulin secretion in PFKFB3$^{\beta KO}$ hIAPP$^{+/-}$+HFD mice. The inventors next asked whether impaired insulin secretion in PFKFB3$^{\beta KO}$ hIAPP$^{+/-}$+HFD mice was due to a failure to expand the β-cell mass under diabetogenic stress in the absence of PFKFB3.

Figure 10B:
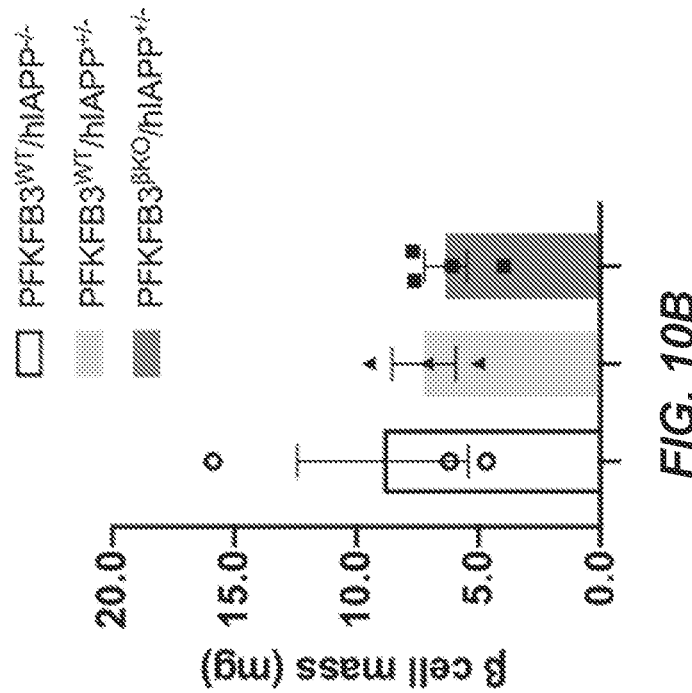
FIGS. 10A-10F show results demonstrating that PFKFB3$^{\beta KO}$ IAPP$^{+/-}$ mice show increased β-cell/a-cell ratio in spite of the increase in the cell death relative to PFKFB3$^{WT}$ IAPP$^{+/-}$ mice.
Figure 10A:
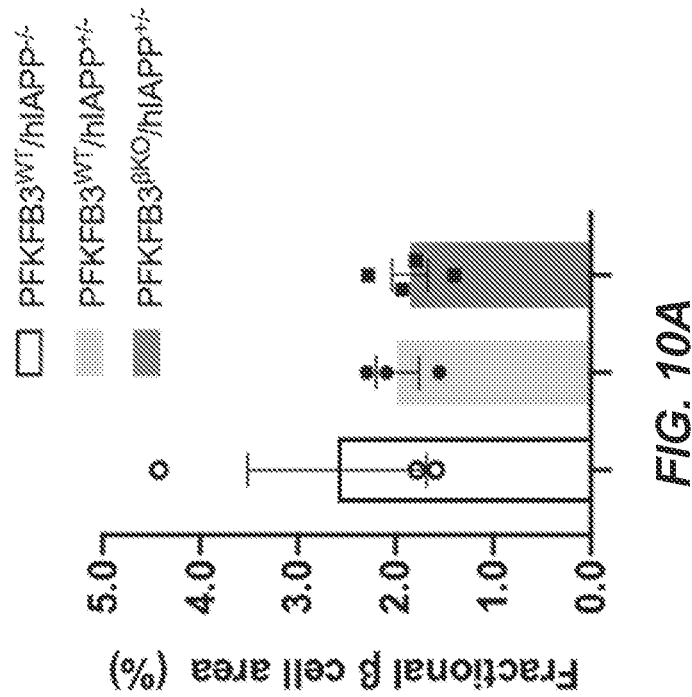
Figure 10D:
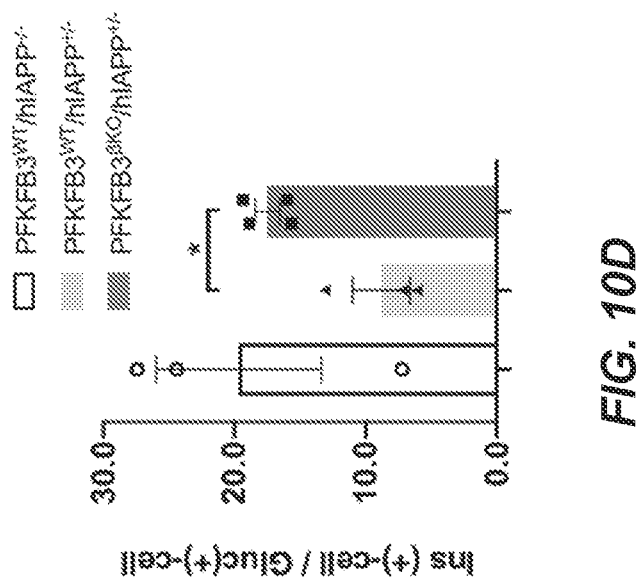
Figure 10C:
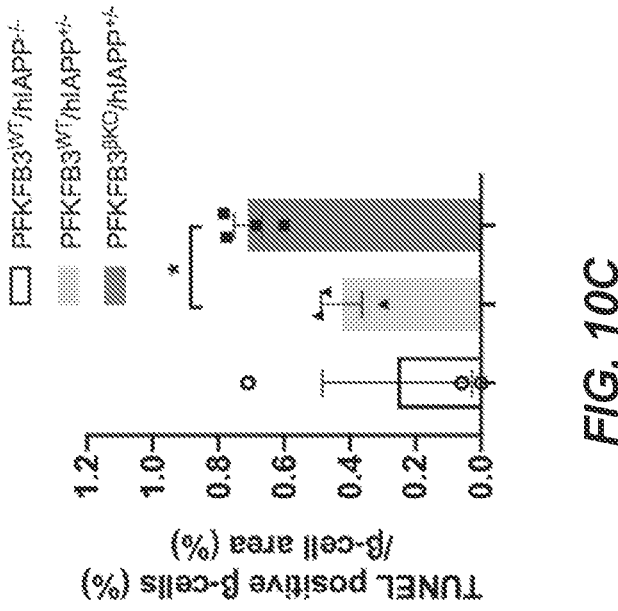
Figures 10E, 10F:
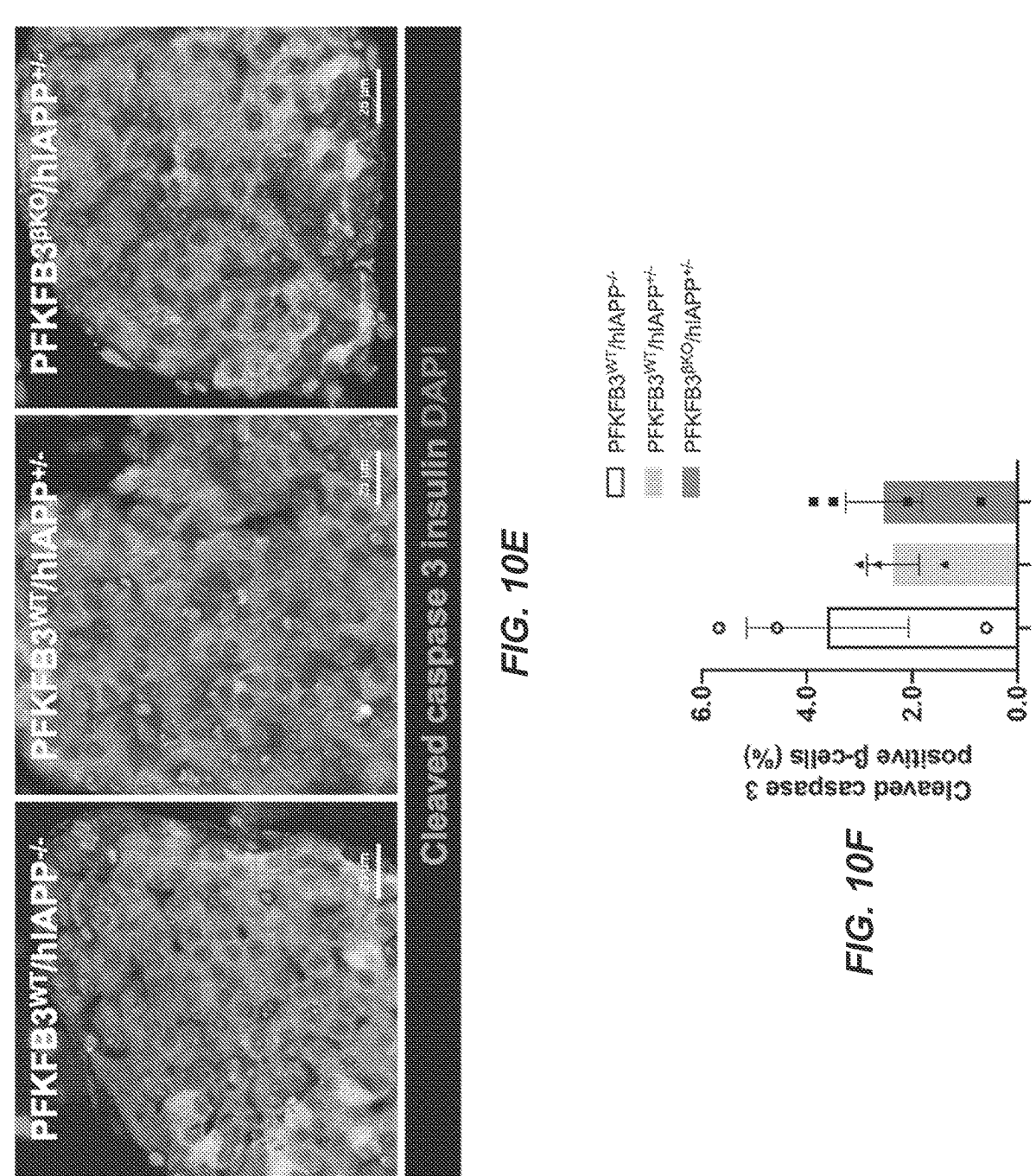

Thus, it became imperative to compare β-cell fractional area and mass. β-cell fractional area and mass were unaltered among the experimental groups (FIGS. 10A and 10B). To investigate growth dynamics that ultimately led to comparable β-cell mass between PFKFB3$^{\beta KO}$ hIAPP$^{+/-}$+HFD- and PFKFB3$^{WT}$ hIAPP$^{+/-}$+HFD mice, TUNEL staining was performed as a measurement of past cell dying (FIG. 10C) and cleaved caspase 3 immunostaining as a measurement of active β-cell death (FIGS. 10E and 10F). β-cell death was increased in the PFKFB3$^{\beta KO}$ hIAPP$^{+/-}$+HFD mice compared with PFKFB3$^{WT}$ hIAPP$^{+/-}$+HFD mice (FIG. 10C). Surprisingly, β-/α cell ratio was increased in PFKFB3$^{KO}$ hIAPP$^{+/-}$+HFD-relative to PFKFB3$^{WT}$ hIAPP$^{+/-}$+HFD mice (FIG. 10D). No difference in active cell death was observed based on cleaved caspase 3 immunostaining of all experimental mice groups. Thus, β-cells from PFKFB3$^{\beta KO}$ hIAPP$^{+/-}$+HFD mice were marked by increased past cell death and no difference in the ongoing cell death compared to the other groups.

Figure 11A:
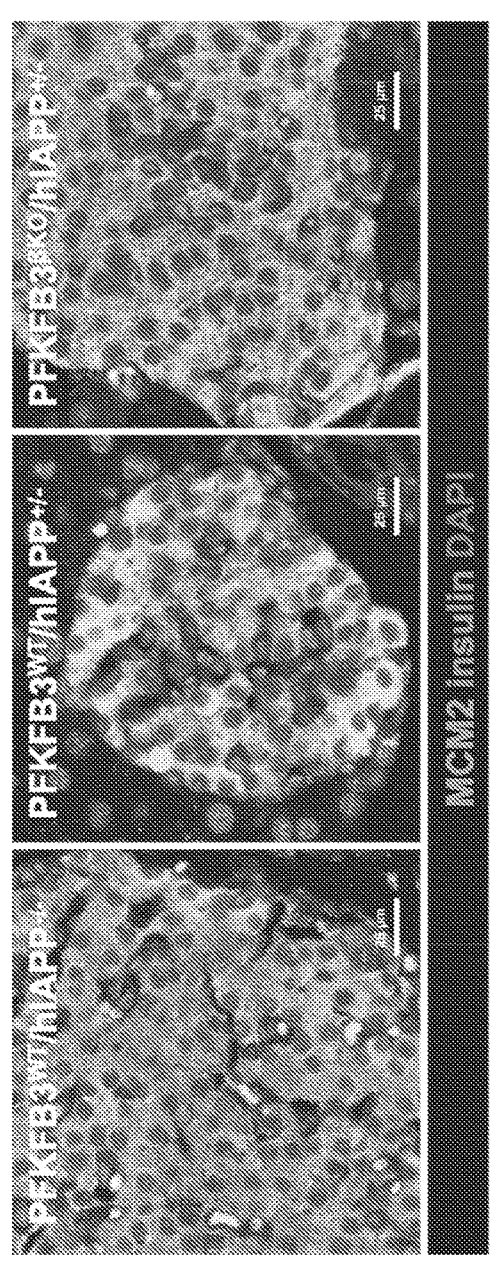
FIGS. 11A-11D shows results demonstrating that PFKFB3$^{\beta KO}$ IAPP$^{+/-}$ mice show increased healthy β-cell replication compared to PFKFB3$^{WT}$ IAPP$^{+/-}$ mice.
Figure 11B:
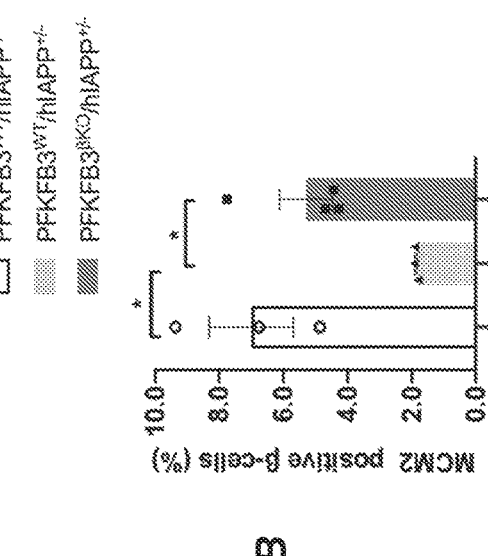

To further elucidate if the increase in β-/α cell ratio relied on the increased generation of β-cells, immunolabeling was performed with an early replication initiation marker, minichromosome maintenance protein 2 (MCM2) [19, 20]. The results showed that β-cells from PFKFB3$^{\beta KO}$ hIAPP$^{+/-}$+HFD mice exhibited a three-fold increase in MCM2 labeling (5.3%±0.8%, *p<0.05), indicating increased β-cell replication compared to PFKFB3$^{WT}$ hIAPP$^{+/-}$+HFD mice (1.9±0.04%) and similar to PFKFB3$^{WT}$ hIAPP$^{-/-}$+HFD controls (7.0±1.3%, FIGS. 11A and 11B). Despite the increase in both cell death and β-cell replication in PFKFB3$^{βKO}$ hIAPP$^{+/-}$+HFD mice, β-cell fractional area was comparable in all three groups (FIG. 10A). Thus, the increment in β-cell replication in the PFKFB3$^{βKO}$ hIAPP$^{+/-}$+HFD mice appeared to maintain the β-cell mass despite the increased cell death and initial loss of damaged β-cells (measured by TUNEL assay) in the absence of PFKFB3 protection and prosurvival role.

Figure 11C:
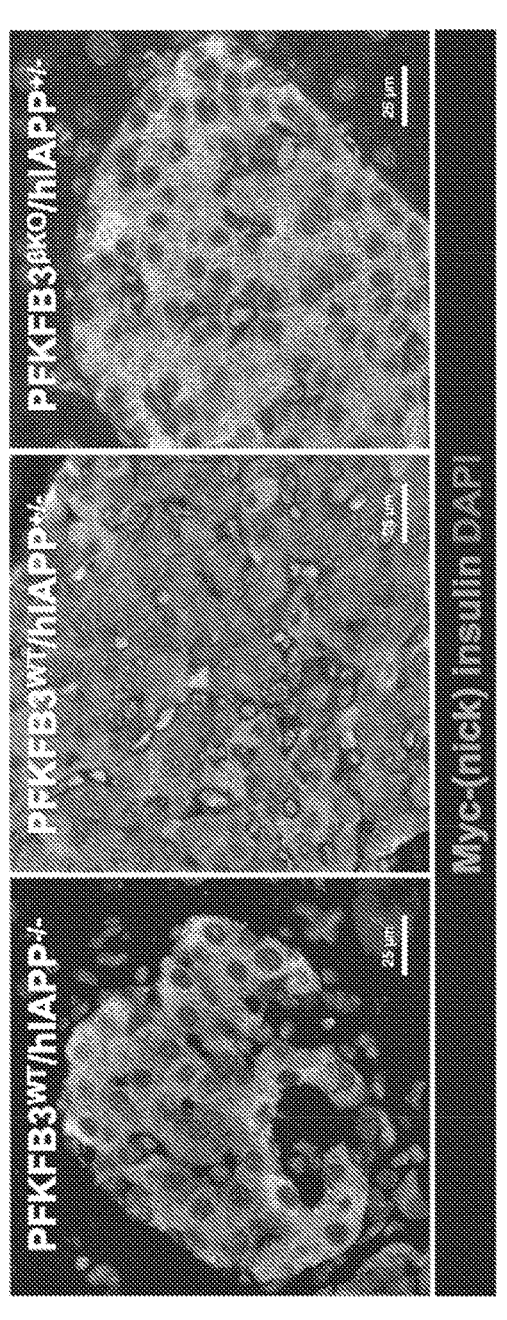
Figure 11D:
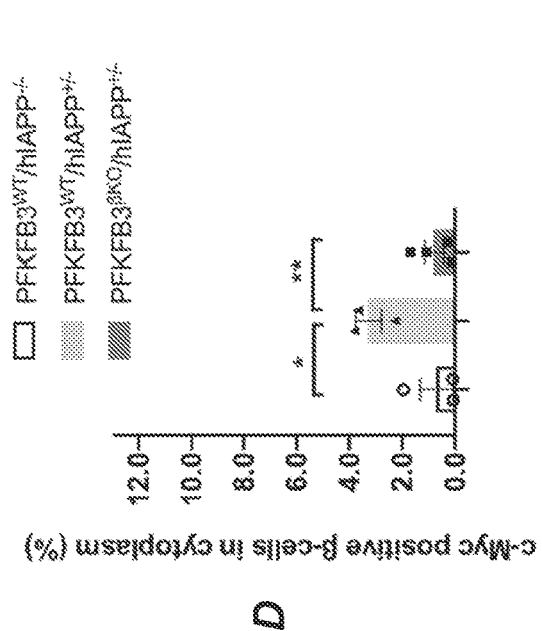

To clarify whether replicating β-cells possessed any residual injury, the inventors made use of the specific marker of hIAPP-incurred damage in β-cells—the cytoplasmic accumulation of the calpain-mediated truncation of the protein c-Myc, called Myc-nick [14]. The analysis of the c-Myc staining revealed an increase of Myc-nick expression in PFKFB3$^{WT}$ hIAPP$^{+/-}$ (3.3±0.5%, *p<0.05) under diabetogenic stress but reversal to PFKFB3$^{WT}$ hIAPP$^{-/-}$+HFD control mice levels in PFKFB3$^{βKO}$ hIAPP$^{+/-}$+HFD mice (0.8±0.4% and 0.7±0.6%, respectively, FIGS. 11C and 11D). These results indicated that healthy β-cells contributed to the increment in replication, likely after reduced hIAPP protein misfolding stress.

Figures 8C, 8D:
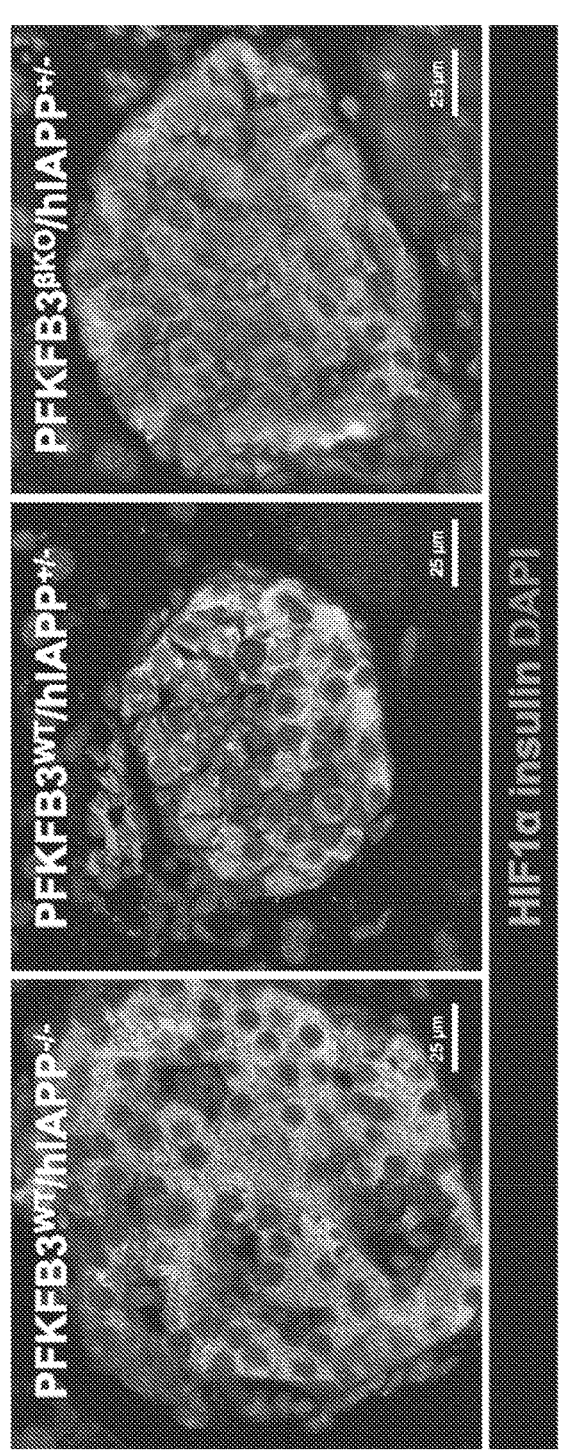
Figures 12A, 12B:
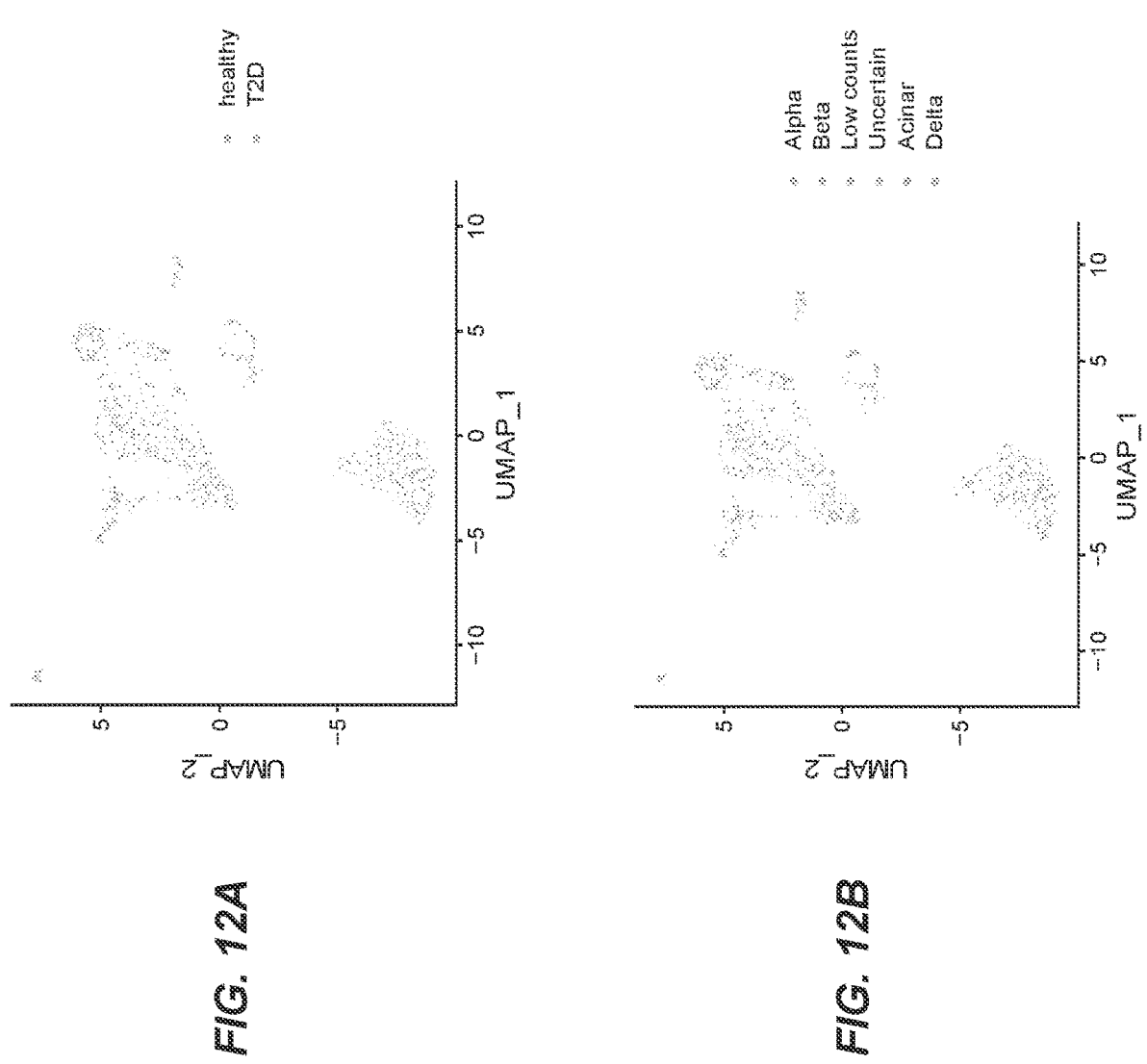
FIGS. 12A-12D show results demonstrating that UMAP clustering of β-cells from published RNA-Seq data [26] identified a cluster 7 subpopulation that overlaps with LDHA positive (β-cells with HIF1α signature).
Figures 12C, 12D:
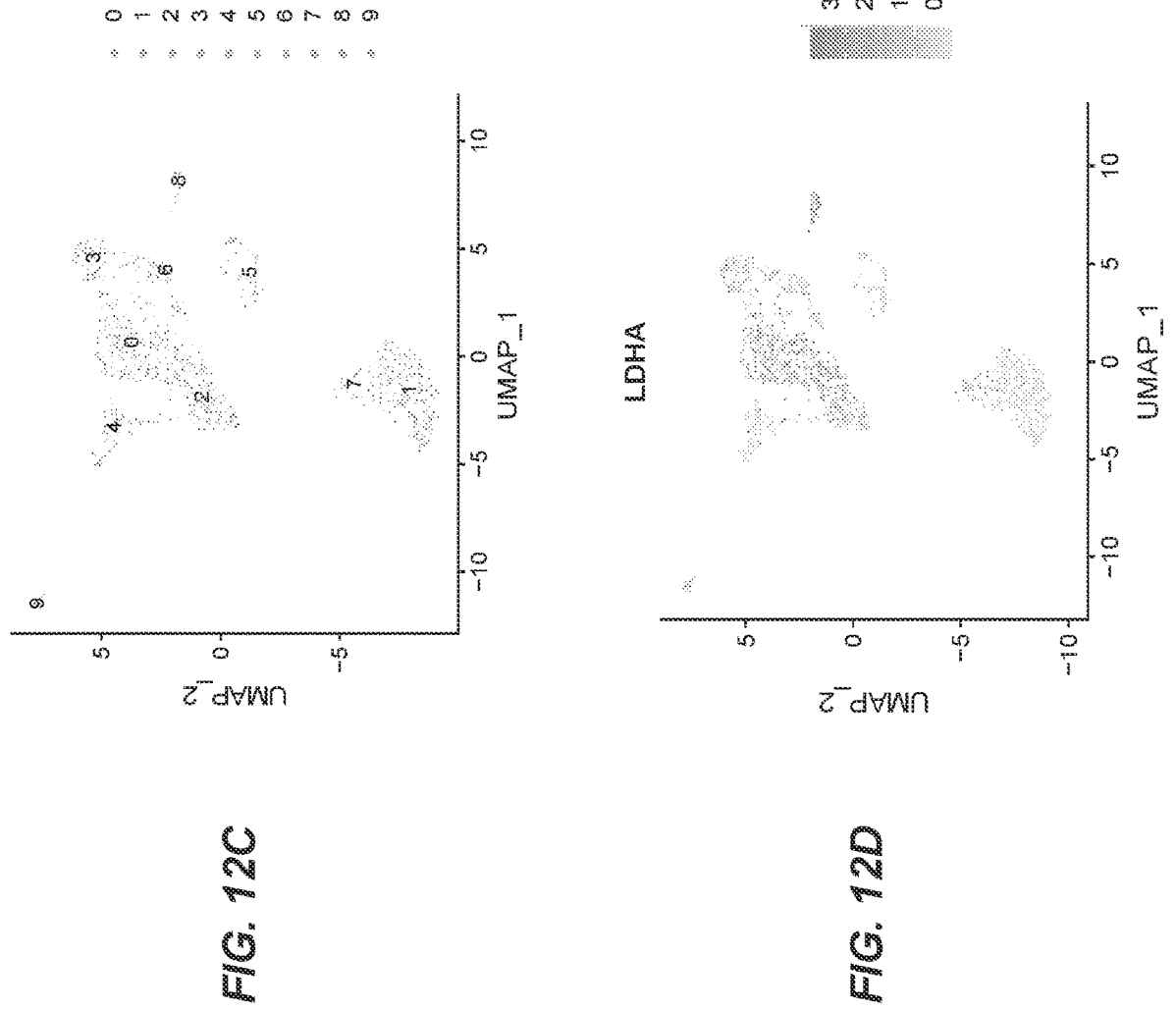
Figure 19:
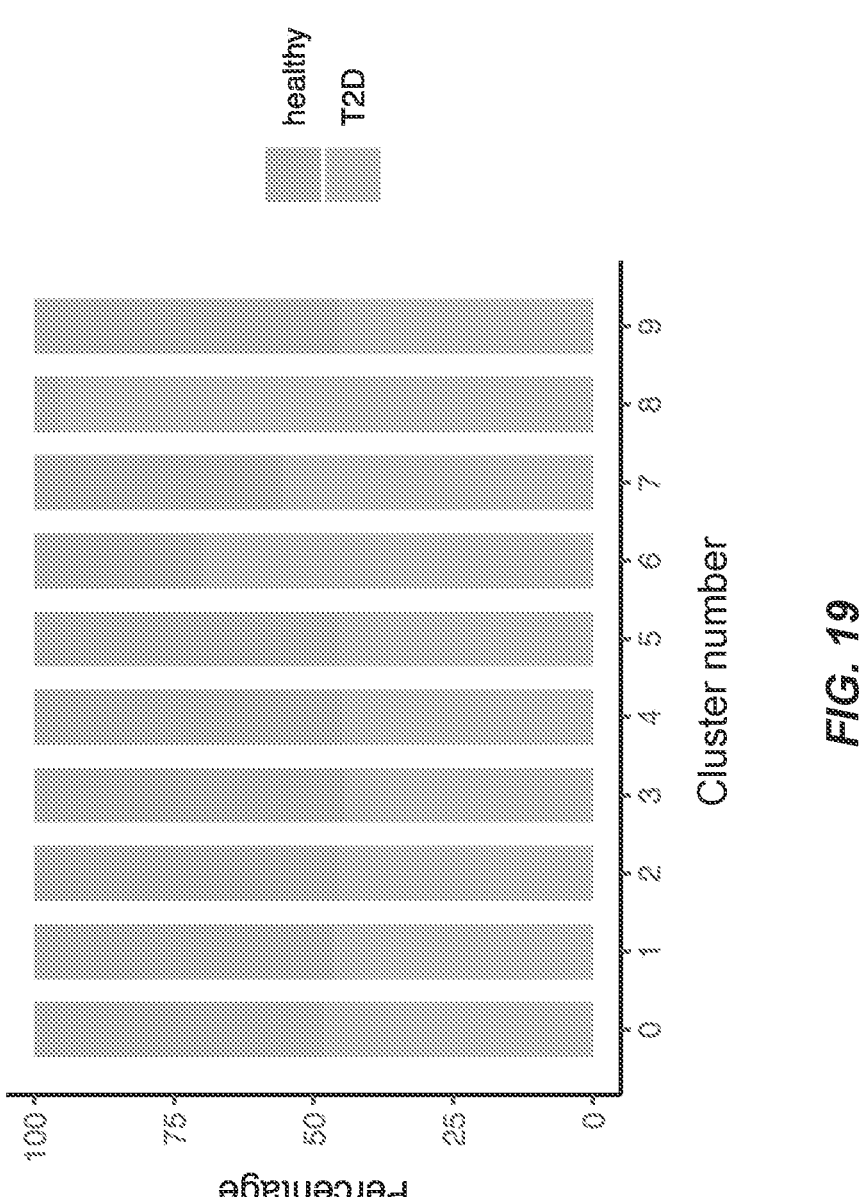
FIG. 19 shows relative contribution of nine annotated pancreatic cell types in health and T2D presentated as a percentage (%).
Figure 20:
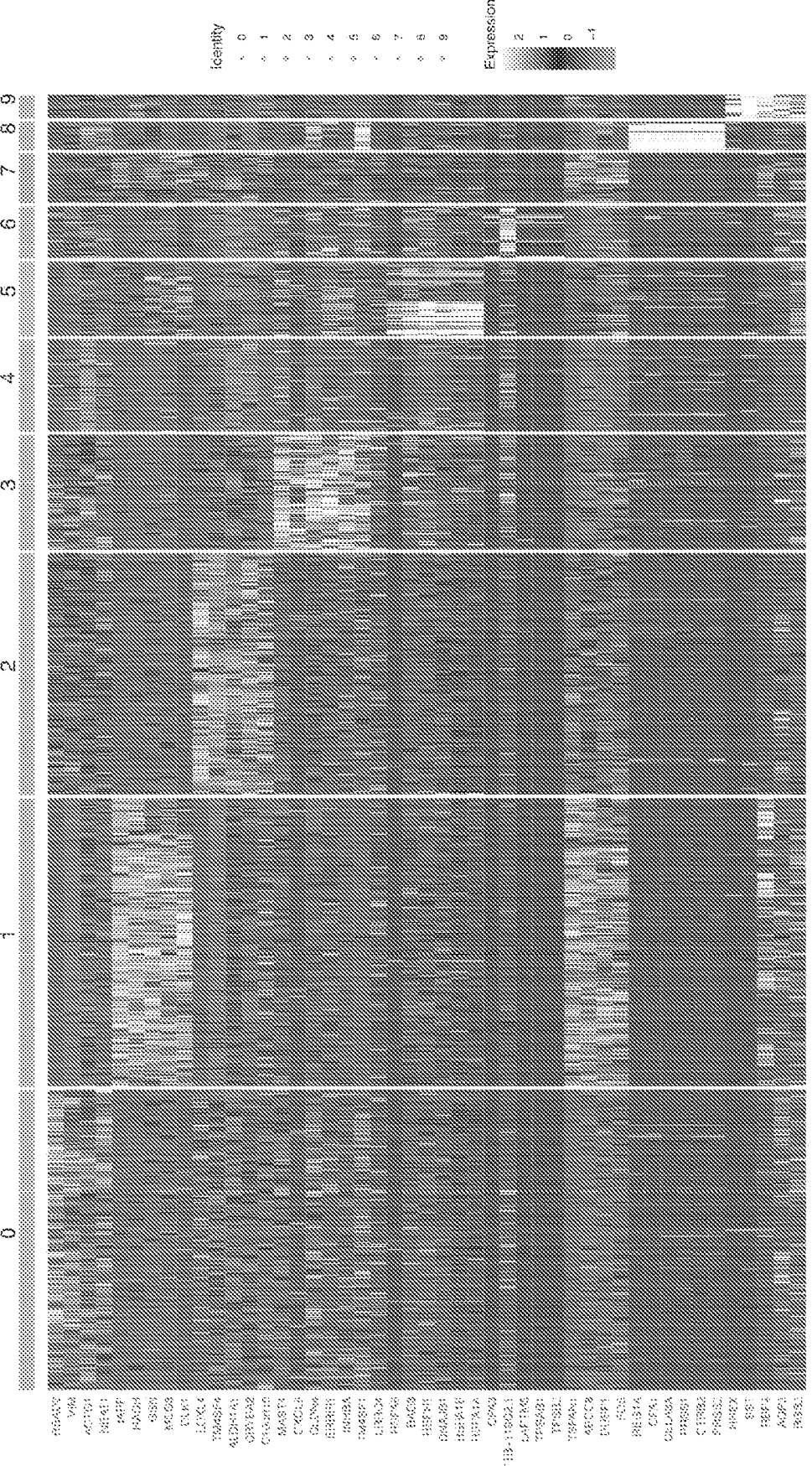
FIG. 20 shows results from single cell RNA sequencing analysis of human pancreatic islet cells from healthy and T2D donors. The marker genes were ranked by expression fold changes comparing the indicated cluster to all the other clusters. The size of the dots represents percentage of cells the gene was detected in. The color scale represents the scaled expression of the gene.
Figure 21:
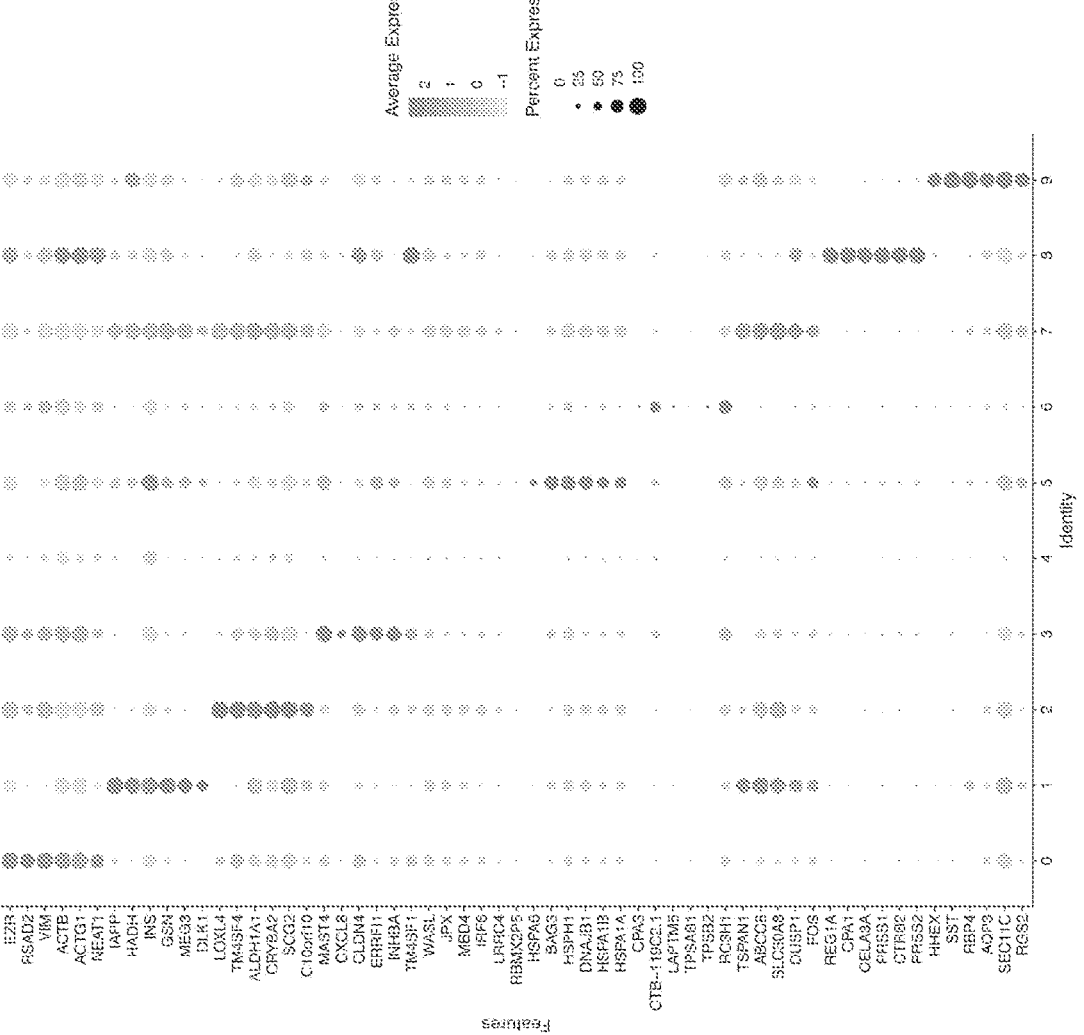
FIG. 21 shows a dotplot showing the top marker genes for each cluster. The marker genes were ranked by expression fold changes comparing the indicated cluster to all the other clusters. The size of the dots represents percentage of cells the gene was detected in. The color scale represents the scaled expression of the gene.
Figure 22A:
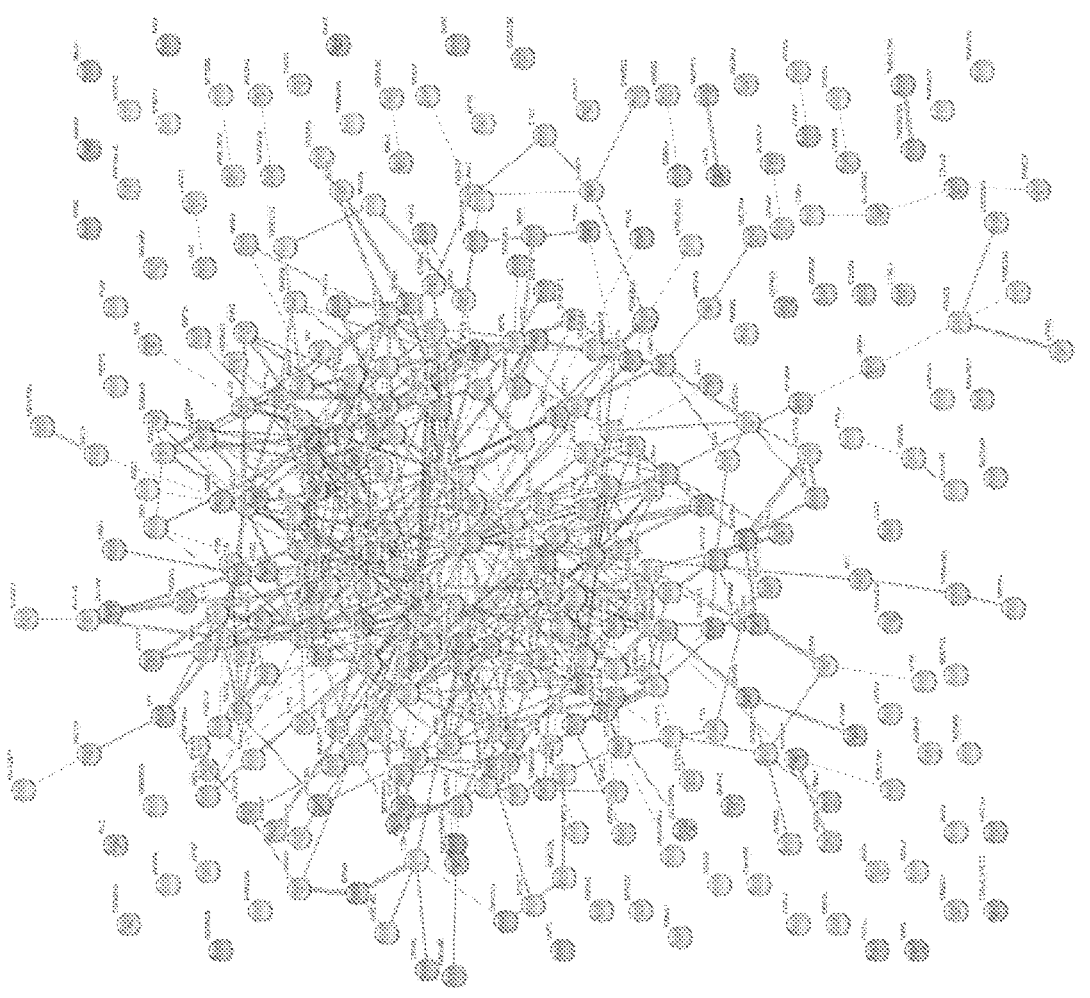
FIGS. 22A and 22B show results from STRING analysis to present the relationship between the differentially expressed genes in Cluster 7 versus Cluster 1 in healthy (ND) (FIG. 22A) and in type-2 diabetes (T2D) (FIG. 22B).
Figure 22B:
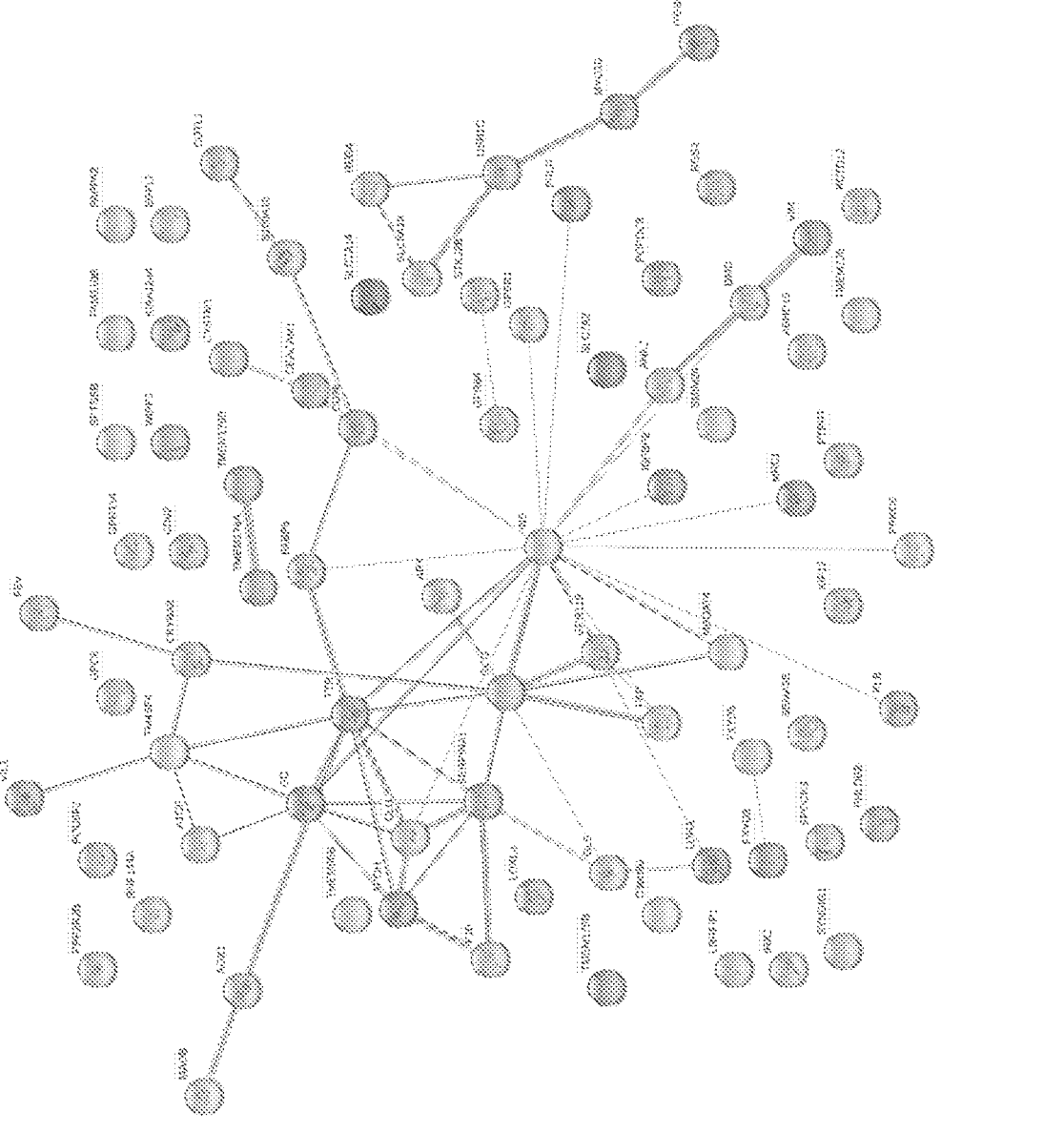
Figure 23A:
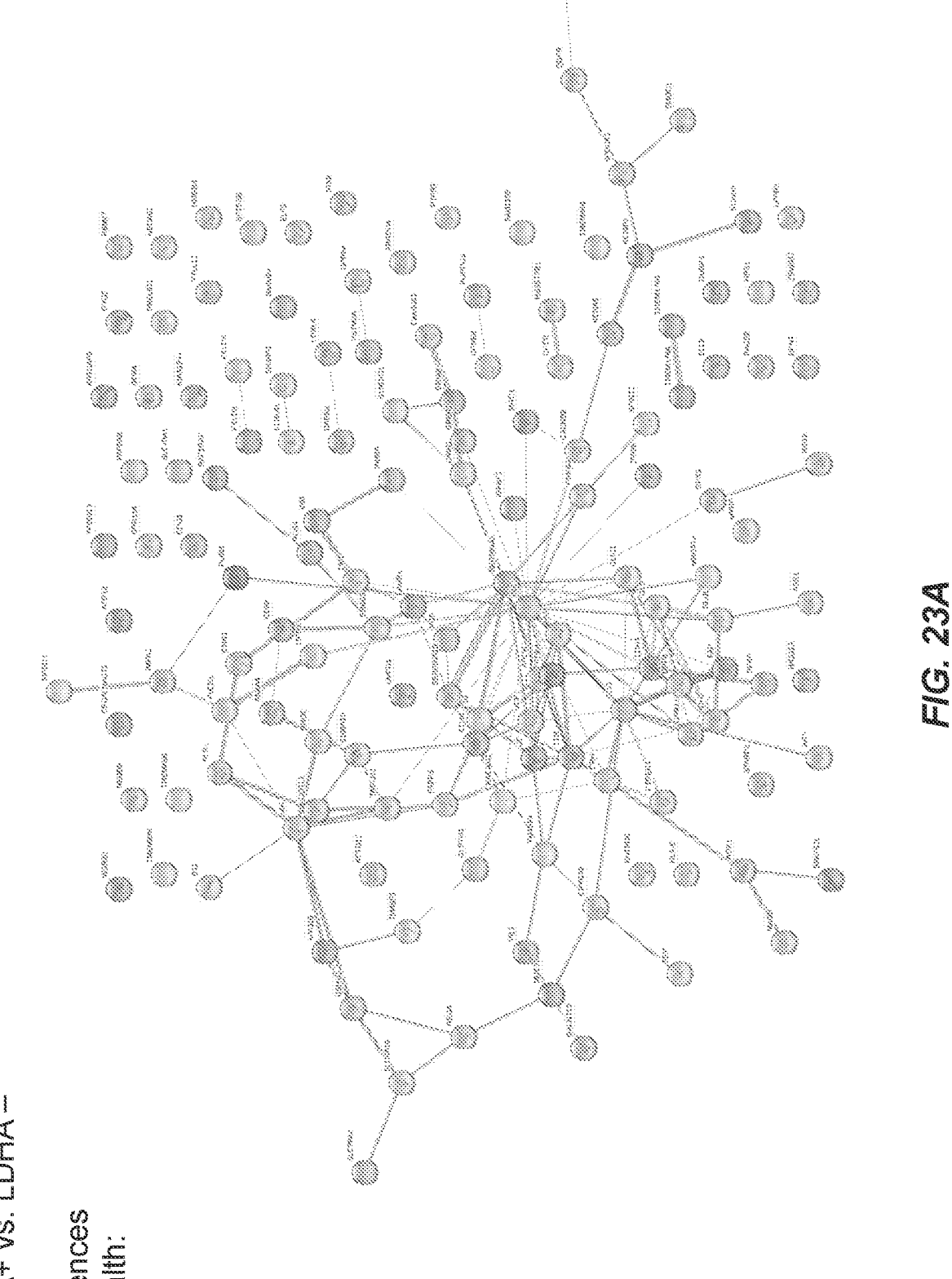
FIGS. 23A and 23B show results from STRING analysis to present the relationship between the differentially expressed genes in LDHA positive (Cluster 7) and LDHA negative β-cells (Cluster 1) in healthy (ND) (FIG. 23A) and in type-2 diabetes (T2D) (FIG. 23B).
Figure 23B:
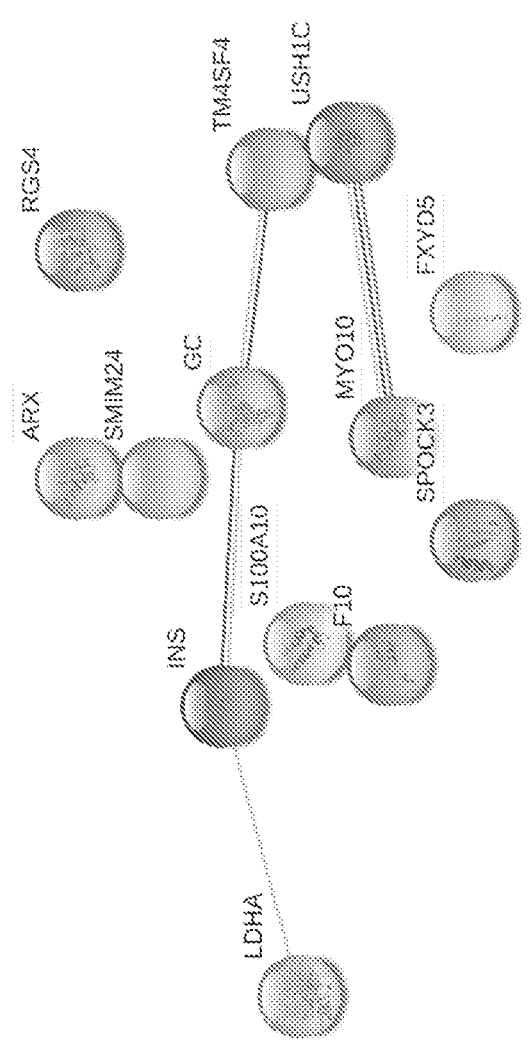
Figure 24A:
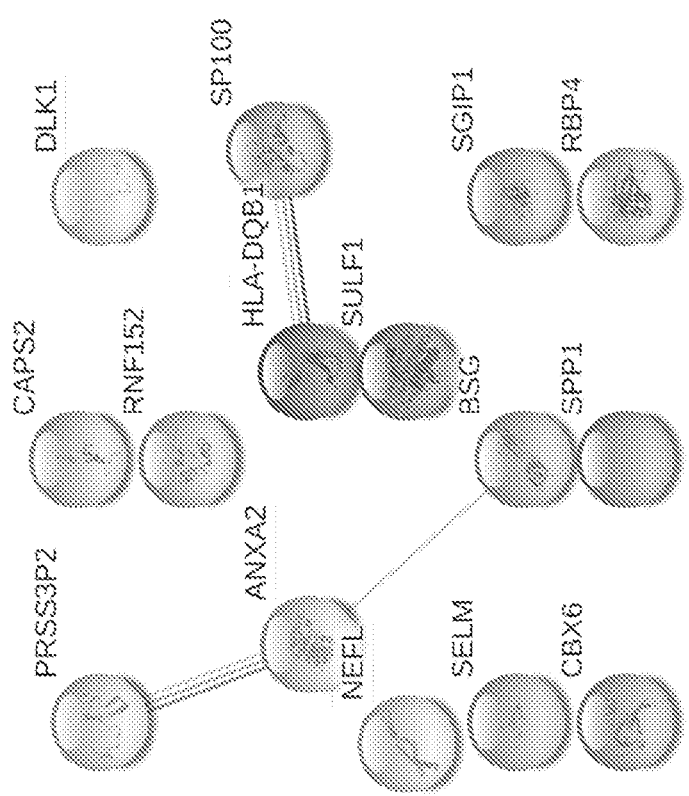
FIGS. 24A and 24B show results from STRING analysis to present the relationship between the differentially expressed genes in healthy (ND) subject in either Cluster 1 (FIG. 24A) or LDHA negative (FIG. 24B) β-cells.
Figure 24B:
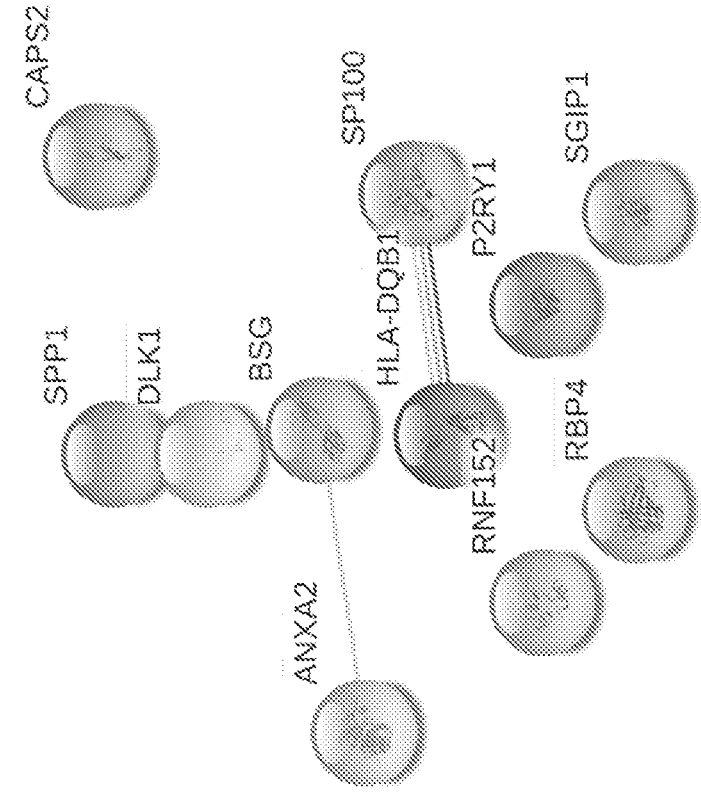

HIF1α immunostaining in the pancreatic sections of PFKFB3$^{βKO}$ hIAPP$^{+/-}$+HFD affected about 14% of all β-cells and although it coincided with reduced misfolding protein stress measured by cytoplasmic c-Myc, this potentially indicated a reason for the non-recovered metabolic function in replicating β-cells (FIGS. 8C and 8D). To characterize the potential contribution of these HIF1α-positive β-cells to loss of function, published single cell RNA Seq (scRNA Seq) data from humans with T2D was used in comparison to nondiabetics [1]. First, the inventors analyzed the quality and validated the scRNA Seq data (FIGS. 11A-12D). Pancreatic cells from healthy and T2D donors were reclustered (umap_cluster) and annotated to the specific cell types based on the gene markers such as insulin (INS) for β-cells (umap_celltype, FIGS. 12A-12D). Nine different cell types were identified and the gene expression that delineated their differences are presented in FIGS. 12C, 20, and 21. Using INS as a β-cell marker, two clusters of β-cells were identified, cluster 1 and cluster 7, while clusters 2-6, 8 and 9 referred to other pancreatic cell types (FIGS. 12B and 12C). Composition in clusters 6 (α-cell subpopulation), 7 (β-cell subpopulation) and 8 (δ-cells) differed the most between healthy and T2D donors (FIG. 19). Since HIF1α is mainly regulated in a posttranslational manner, β-cells were additionally distinguished based on the expression or not of lactate dehydrogenase A (LDHA), a HIF1α transcriptional target from aerobic glycolysis (FIG. 12D). For each condition, and based on LDHA expression, cells were split into LDHA-positive and LDHA-negative cells and differential expression analysis was performed between the two groups. LDHA positive β-cells overlapped with cluster 7 delineated β-cell subpopulation and, independent of the disease state, were associated with genes relevant to metabolism, such as LDHA, aryl hydrocarbon nuclear translocator 2 (ARNT2, i.e., HIF1α), glucokinase (GK), phosphofructokinase 1 platelet type (PFKFP), pyruvate dehydrogenase kinase 4 (PDK4), or genes relevant for insulin secretion such as FBP1 via phosphoenolpyruvate pool, or identity such as glucagon (GCG, pro-α-cell identity) and Aristaless Related Homeobox (ARX, pro-α-cell identity) and INS (lower expression, β-cell identity). LDHA-positive or cluster 7 β-cells showed an immature phenotype in line with upregulation of genes such as aldehyde dehydrogenase 1A1 (ALDH1A1). These results suggested that, in humans with T2D, a fraction of β-cells (LDHA-positive cells overlapping with cluster 7 β-cell) possess a genetic signature with reduced INS expression and increased GCG and ARX expression. Enrichment data by Ingenuity Pathway Analysis (IPA) revealed that the difference between significantly altered genes in Cluster 1 and 7 and between LDHA positive and negative cells is recapitulated by LXR/RXR retinoid receptor, indicating this upstream regulator as a part of the epistatic HIF1α-PFKFB3 non-canonical metabolic pathway. Moreover, the String analysis clearly indicated that while differences between clusters 1 and 7 as well as LDHA negative and positive β-cells were well preserved in health, these differences were strongly reduced in T2D. These data suggested that in T2D, clusters of β-cells begin to resemble each other, and the differences are reduced under stress (FIGS. 22A-23B). When compared between T2D and healthy individuals, differentially expressed genes in either cluster 1 or LDHA-negative β-cells showed a significant overlap.

Figures 13A, 13B, 13C, 13D:
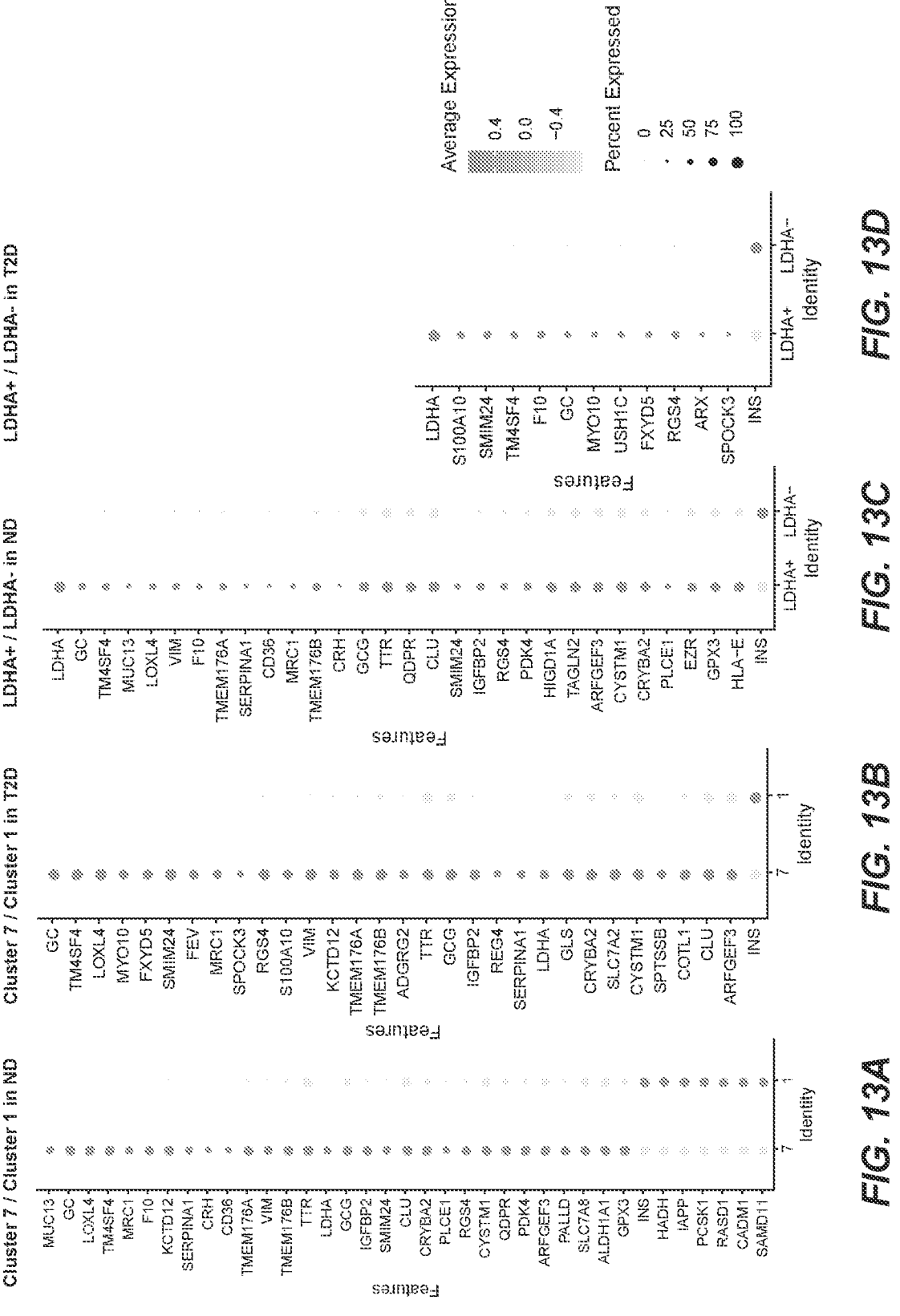
FIGS. 13A-13D show results demonstrating that differential gene expression between β-cell subpopulations from ND- or T2D revealed that Cluster 7 and LDHA positive β-cells share double identity [insulin (INS+) and glucagon (GCG+)]. Differential gene expression between β-cells Cluster 7 relative to Cluster 1 is shown in nondiabetics (ND) (FIG. 13A) and in T2D (FIG. 13B). Differential gene expression between LDHA positive and negative β-cells Cluster is shown in nondiabetics (ND) (FIG. 13C) and in T2D (FIG. 13D).
Figure 14E:
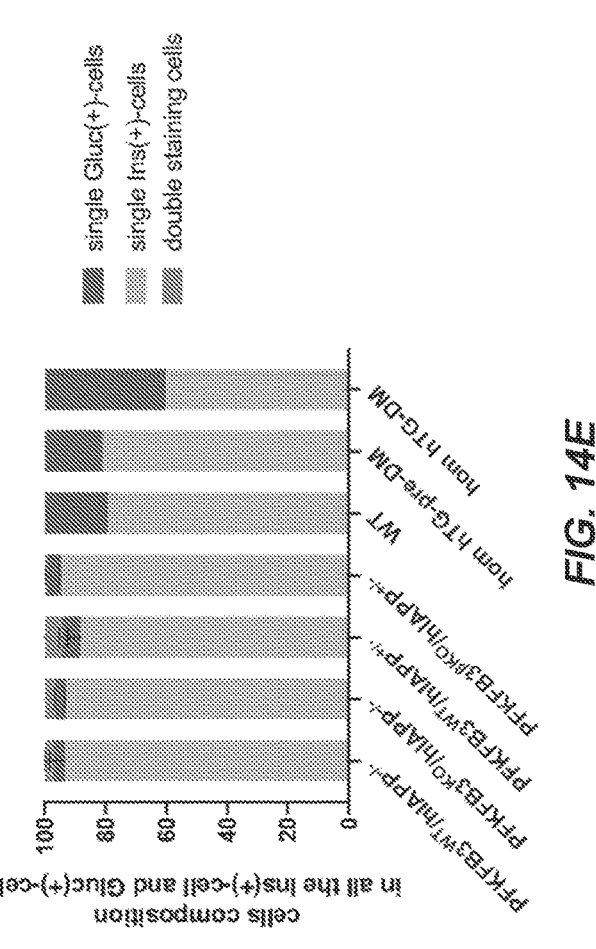
Figure 14D:
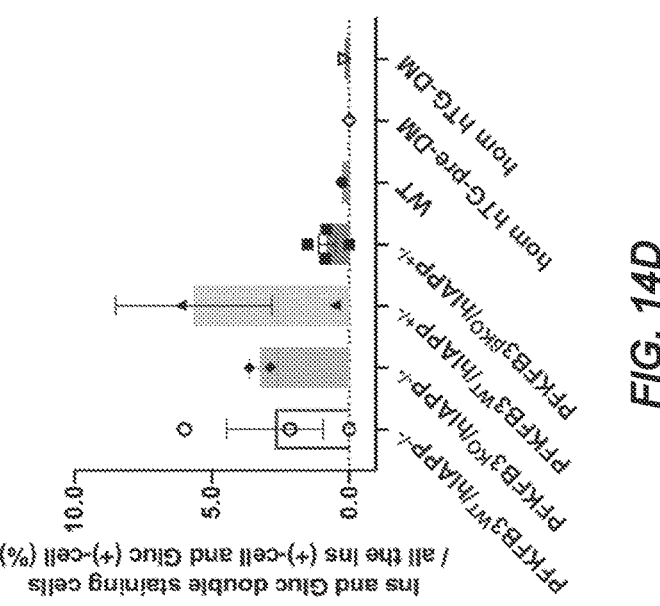
Figure 15B:
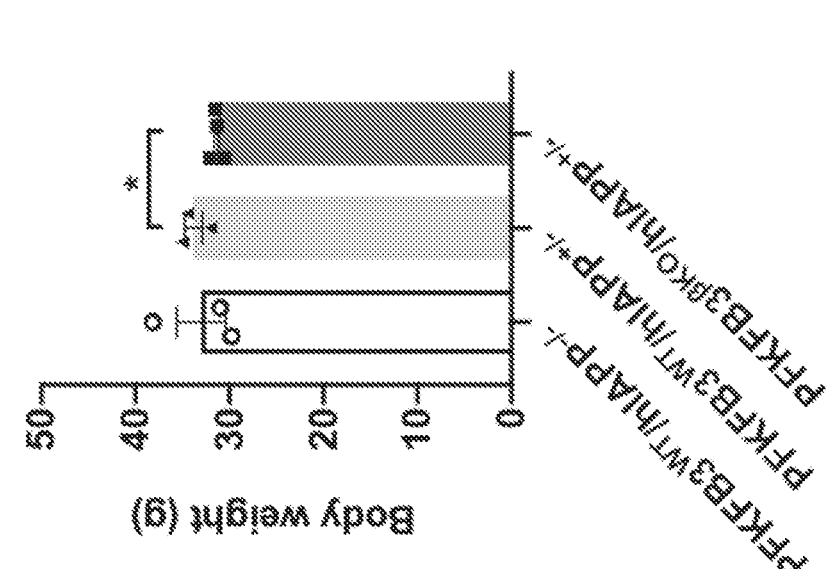
FIGS. 15A-15D show results demonstrating that body weight among experimental groups during the course of experiment was unaffected. Body weight in indicated experimental groups at the baseline (t=0) (FIG. 15A), 1 week before onset of HFD (FIG. 15B) at 4 weeks HFD (FIG. 15C) and at 13 weeks HFD (FIG. 15D).
Figure 15A:
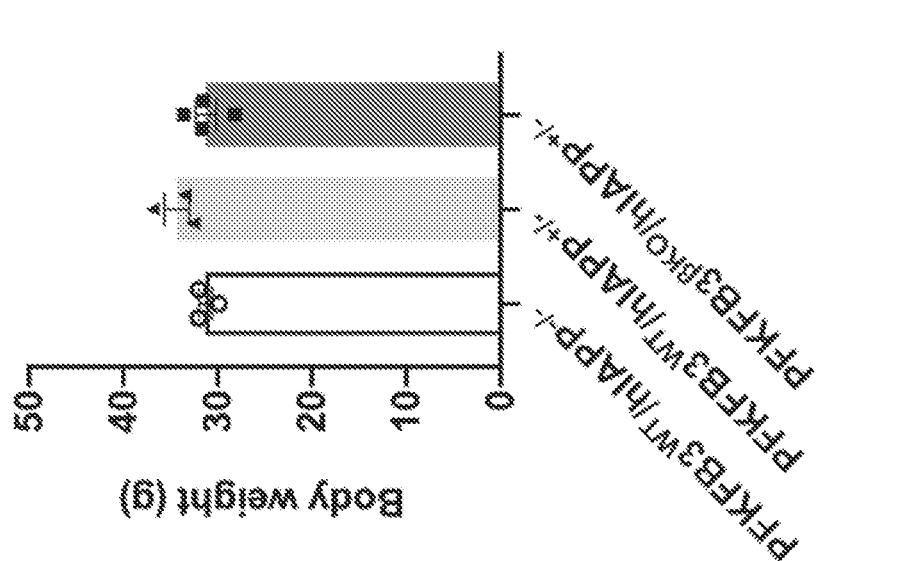
Figure 15D:
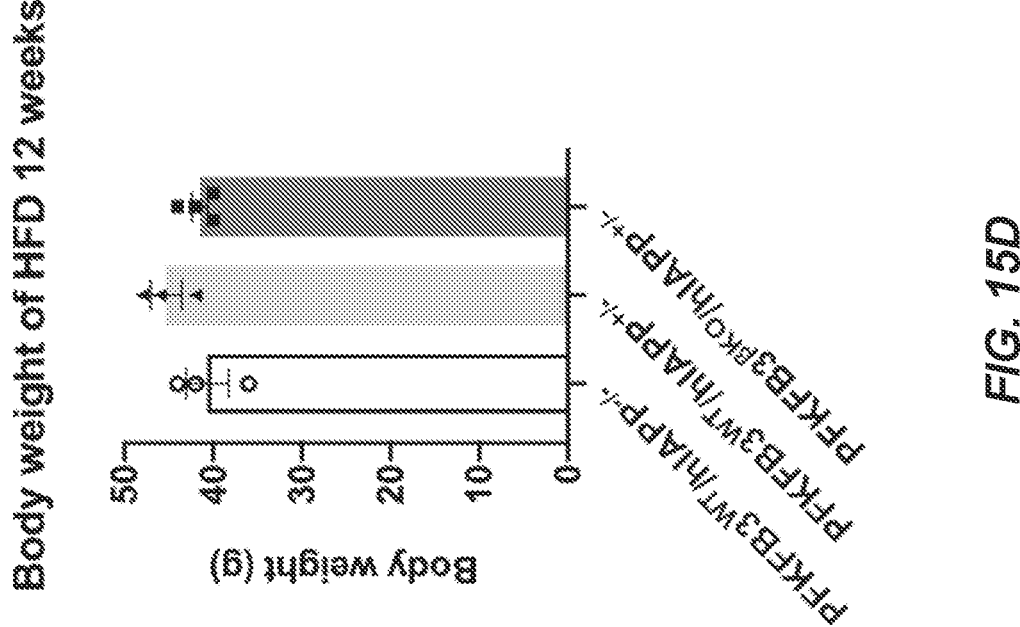
Figure 15C:
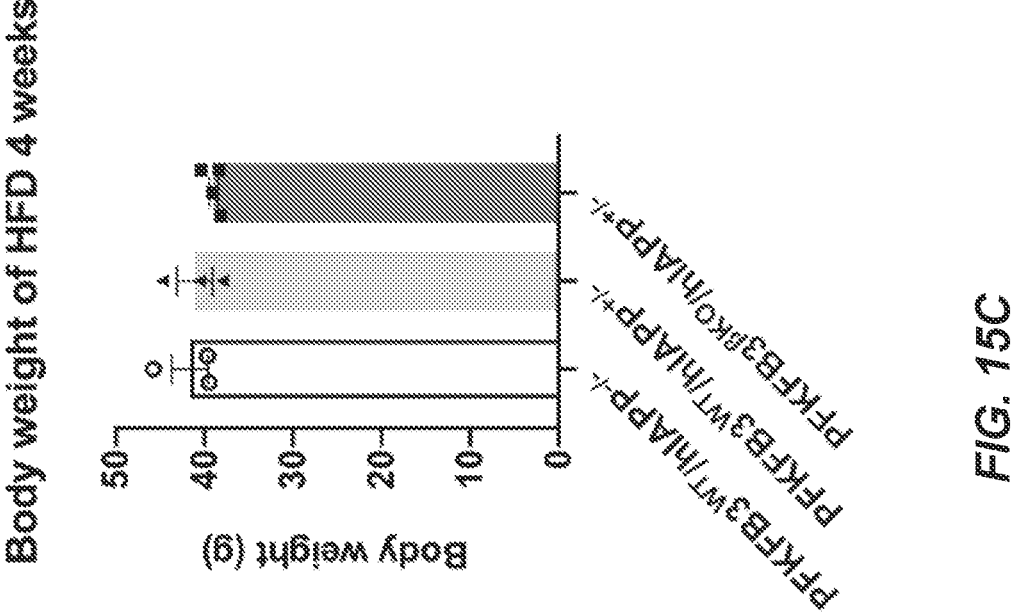

To find a complement of β-cell population in cluster 7 or LDHA positive cells, the inventors double stained pancreatic sections from the experimental mice groups with specific insulin and glucagon antibodies. Diabetogenic stress increased twice the number of double-positive cells in PFKFB3$^{WT}$ hIAPP$^{+/-}$+HFD compared to PFKFB3$^{WT}$ hIAPP$^{-/-}$+HFD controls (5.7±2.8% relative to 2.7±1.8%, respectively). PFKFB3 knockout led to a reduction of cells with concomitant insulin and glucagon immunopositivity when compared to PFKFB3$^{WT}$ DS (0.8±0.3% relative to 5.7±2.8%, FIG. 13A). Not only was the fraction of bihormonal (insulin$^+$glucagon$^+$) cells abolished upon elimination of PFKFB3 positive damaged β-cells, but it also correlated with a significant increase in the β-cells (*p<0.05). This indicated that PFKFB3 disruption led to specific culling of β-cells with double insulin and glucagon identity and/or that the replication is stimulated from insulin only positive β-cells. The opposite was true for α-cells relative to all α-, β-, and bihormonal cells together (FIG. 13B). This ratio reached control levels and was reduced in PFKFB3$^{βKO}$ hIAPP$^{+/-}$+HFD compared to PFKFB3$^{WT}$ hIAPP$^{+/-}$+HFD mice (*p<0.05). The double insulin and glucagon stained cells were clearly present in the experimental mice exposed to high fat diet and were not detected in WT controls or hIAPP$^{+/+}$-neither at prediabetic or diabetic age (FIGS. 13C and 13D).

Thus, PFKFB3 knockout led to the disappearance of β-cells with double insulin and glucagon identity, indicating that those are the cells that not only depend on PFKFB3-mediated survival upon hIAPP injury but the ones that accommodate the survival via double identity, probably both contributing to their compromised function.

Interestingly, these data pointed out that the HIF1a-positive cells in PFKFB3$^{βKO}$ hIAPP$^{+/-}$+HFD do not possess double β- and α-identity indicating that the survival of double β- and α-identity possessing cells depends on PFKFB3 and not HIF1α.

These analyses also indicated that accumulation of HIF1α-positive cells in the mouse model of diabetes may be responsible for the loss of β-cell function in spite of β-cell mass recovery after PFKFB3 gene depletion. PFKFB3 depletion seems to trigger culling of damaged β-cells with both β-cell and α-cell identity that is both sufficient and necessary to replenish healthy β-cells by replication. However, independent immunolabeling by HIF1α further compromises the β-cell insulin secretion.

These studies strongly suggest that targeting (i.e., inhibiting) HIF1α, with or without co-targeting of PFKFB3, will lead to recovery of functionally competent β-cell mass and reversal of diabetes.

Discussion

In these studies, the inventors demonstrate that the specific β-cell disruption of Pfkfb3 gene in adult mice under high diabetogenic stress leads to a partial islet regeneration.

This is achieved via culling of damaged and bihormonal (insulin and glucagon positive) cells and replication of remnant healthy β-cells.

Culling probably affects a substantial number of β-cells. PFKFB3 implication in remodeled metabolism explains its impact on survival—[13] but also poses a question related to the preservation of β-cell function. So metabolic remodeling by HIF1α-PFKFB3 pathway in misfolded protein stress (hIAPP) recapitulates the consequences of HIF1α expression after conditional inactivation of von Hippel Lindau gene (Vhl) [13, 31]. In presence or absence of diabetogenic stress, HIF1α activation led to diminished glucose-stimulated changes in cytoplasmic $Ca^{2+}$ concentrations, electric activity and insulin secretion culminating in impaired systemic glucose tolerance in pancreatic β-cells [13, 31].

HIF1α was continuosly expressed in a significant number of β-cells from PFKFB3$^{βKO}$ DS mice (~14%). This indicated that in this mouse model of diabetes, pertained HIF1α response is independent of PFKFB3. HIF1α expression levels in PFKFB3$^{βKO}$ DS and PFKFB3$^{WT}$ DS mice (14% and 18%, respectively) paralleled the glucose intolerance and the lower plasma insulin- and C-peptide levels in comparison to WT controls (p<0.05).

To investigate the role of HIF1α in the molecular basis for β-cell dysfunction, sc RNA Seq data from humans with obese-T2D and nondiabetics (ND) [27] was analyzed. The inventors made use of the distinction of LDHA positive-versus negative β-cells since LDHA is a bona fide target, serving as a substitute marker for HIF1α. HIF1α is regulated mainly posttranslationally with no changes in the transcript levels. LDHA positive β-cells overlapped with cluster 7 β-cell subpopulation and were represented by HIF1α- (ARNT2, GK, PFKFP, PDK4) and bihormonal signature (a and β-cell identity) (GCG, ARX and INS) and some markers of immaturity (ALDH 1A1). Double insulin- and glucagon positive cells in the mouse model resembled LDHA positive or cluster 7 β-cells and could originate from dedifferentiated or β-cells subjected to transdifferentiation [32].

Ingenuity Pathway Analysis (IPA) used for comparison between LDHA positive (cluster 7) and LDHA negative (cluster 1) β-cells in both health and T2D, indicated an existence of a master upstream regulator, the liver X receptor, a type of retinoid receptor (LXR/RXR) [33], potentially a part of the epistatic HIF1α metabolic pathway. Activation of this receptor may independently increase aerobic glycolysis in response to high fat diet via transcriptional upregulation of hexokinases 1 and 3 (HK1 and 3) and SLC2A1 (GLUT1)) and interplay with HIF1α [34].

Interestingly, the bihormonal β-cell subpopulation was present in the obese nondiabetics and in our WT controls under HFD indicating that formation of bihormonal cells may well be an adaptive response to increased lipogenesis and high fat diet. As such, double insulin and glucagon positive cells were not detected in WT controls or hIAPP$^{+/+}$ in absence of HFD (used as negative controls), neither at prediabetic or diabetic age. No matter whether in health or in T2D, bihormonal β-cell cluster 7 (LDHA positive β-cells) could be distinguished from cluster 1 by implication of LXR/RXR. Previous reports indicated that unlike acute activation that is adaptive response to increased demand on insulin secretion, the chronic activation of LXR may contribute to β-cell dysfunction by accumulation of free fatty acids and triglycerades [33]. In addition, the STRING analysis indicated that while differences between clusters 1 and 7 as well as LDHA negative and positive β-cells were well preserved in health, these differences were reduced in T2D. Preserved feature of bihormonal cells can be relevant in the context of cell fitness competition, where we propose it could constitute a basis for bihormonal cells' recognition and homeostatic control.

Cell fitness competition is an important extrinsic cell quality control based on the distinction of cell population with inferior—versus cell population with superior fitness (survival) characteristics. This distinction is key in triggering selective culling of the cell population with inferior fitness characteristics ("losers") and propelling the expansion of the cell population with superior fitness characteristics ("winners"). Replacement of the "losers" with the "winners" allows for maintenance of homeostatic tissue. By implication the reversal of cell competitive tissue makeup such as we see in T2D (clusters 1 and 7 resemblance) may lead to inhibition of cell competition followed by tissue dysfunction over time.

In the mouse model of diabetes, PFKFB3 knockout in adult β-cells led to strong reduction of injured β-cells and bihormonal (insulin and glucagon positive) cells and concomitant increase in healthy β-cell replication. The inventors monitored injured β-cells by measuring the extent of the calpain (hIAPP)-mediated truncation of the cytoplasmic c-Myc [26]. Calpain was previously reported to directly reflect hIAPP misfolded protein toxicity [35, 36]. In PFKFB3$^{βKO}$ DS mice, cytoplasmic c-Myc was reversed to the barely detectable levels as measured in WT controls (0.8±0.4% and 0.7±0.6%, respectively).

These results indicated that the increment in replication was contributed by healthy β-cells and was conceivably facilitated by the excelled loss of β-cells with ongoing calpain activation and thus hIAPP injury. Therefore, the results suggested a cell competition-dependent β-cell regeneration by culling of injured β-cells after PFKFB3 knockout. So, further in PFKFB3$^{βKO}$ DS mice the increase in β-/a ratio and the reduction in glucagon levels in comparison to PFKFB3$^{WT}$ DS may have accounted for the observed trend of higher insulin sensitivity [37-39].

In conclusion, the preservation of the β-cell mass and increase in the β-/a ratio in the PFKFB3$^{βKO}$ DS mice stem cumulatively from β-cell replication that overcomes the initial loss of injured β-cells and reduction in bihormonal cells.

While the regenerative growth in diabetogenic stress was critically dependent on PFKFB3, unmatched metabolic function may be accounted to the fraction of HIF1α-positive cells independent of PFKFB3. Thus, in the mouse model of diabetes, HIF1α may be responsible for the loss of β-cell function in spite of β-cell mass recovery after PFKFB3 gene depletion.

These studies strongly suggest that targeting HIF1α with/without co-targeting PFKFB3 will lead to recovery of functionally competent β-cell mass and reversal of diabetes.

Figure 25:
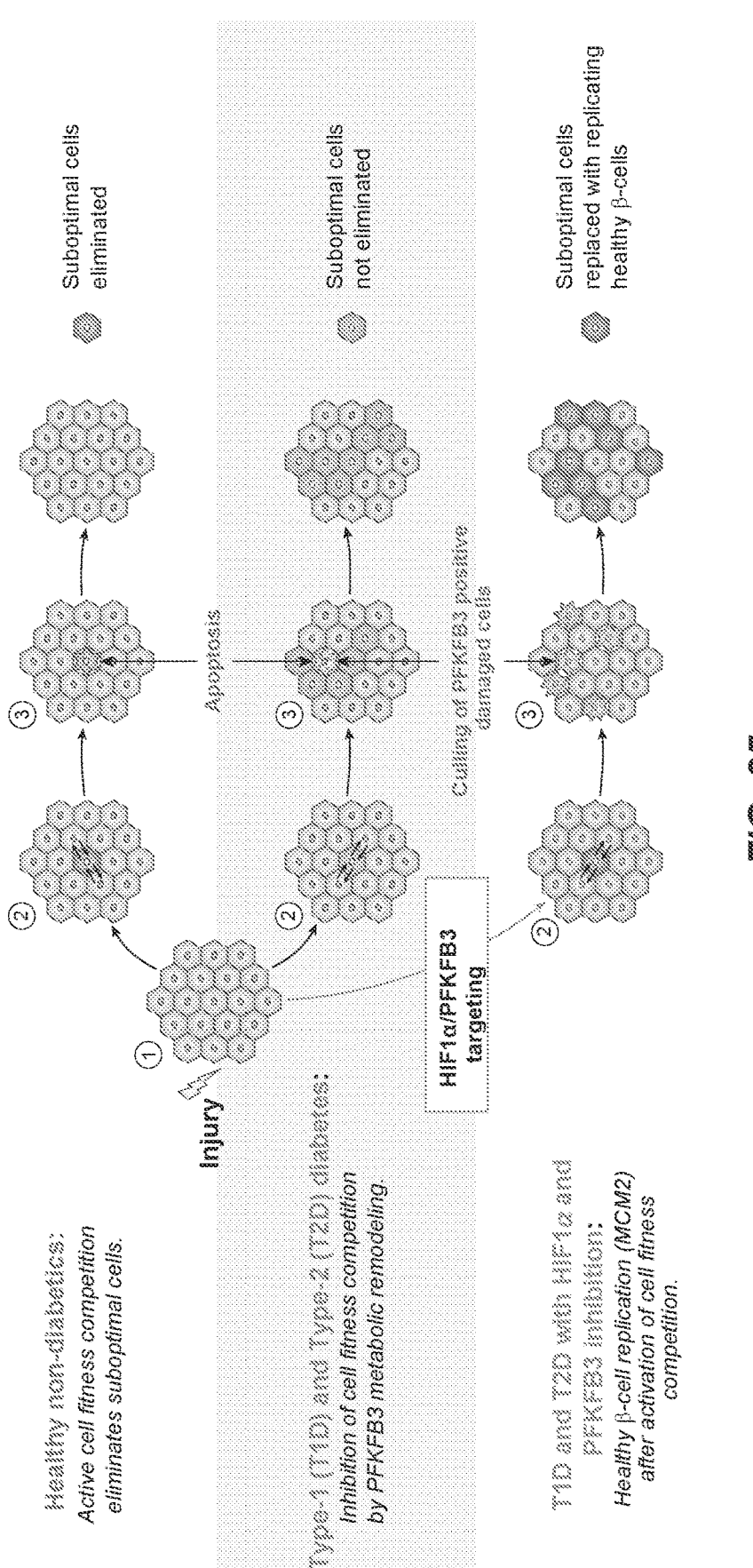
FIG. 25 is a schematic of a model disclosed herein for the role of β-cell fitness comparison in β-cell replenishment under stress.

Example 5—Generation of a Model for the Role of β-Cell Fitness Comparison in β-Cell Replenishment Under Stress A model for the role of β-cell fitness comparison in β-cell replication under stress was generated based on the studies described in Examples 1-4. FIG. 25 shows a schematic of the generated model. The top panel shows how, after metabolic stress such as a high fat diet (HFD) in healthy non-diabetics, suboptimal cells (dark) are eliminated from the tissue by competition with healthy β-cells (light), which replicate to regenerate the lost tissue. The middle panel shows how, in a cell competition in which injury is sustained (T1D and T2D), injured, suboptimal β-cells (dark) survive in spite of reduced fitness and cannot be purged from the tissue because of metabolic remodeling by the HIF1α-PFKFB3 pathway. These injured β-cells may impede healthy β-cell replenishment (replication). The bottom panel shows how, under stress and injury conditions, the targeting of the pro-survival PFKFB3 and/or HIF1α pathway leads to activation of cell competition and elimination of suboptimal (damaged) β-cells (dark). Elimination of suboptimal (damaged) β-cells leads to replication of the remaining healthy β-cells (MCM2-positive cells).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Camunas-Soler, J., et al., Patch-Seq Links Single-Cell Transcriptomes to Human Islet Dysfunction in Diabetes. Cell Metab, 2020. 31(5): p. 1017-1031 e4.

2. Montemurro, C., et al., IAPP toxicity activates HIF1alpha/PFKFB3 signaling delaying beta-cell loss at the expense of beta-cell function. Nat Commun, 2019. 10(1): p. 2679.

3. Matveyenko, A. V. and P. C. Butler, Beta-cell deficit due to increased apoptosis in the human islet amyloid polypeptide transgenic (HIP) rat recapitulates the metabolic defects present in type 2 diabetes. Diabetes, 2006. 55(7): p. 2106-14.

4. Butler, A. E., et al., Beta-cell deficit and increased beta-cell apoptosis in humans with type 2 diabetes. Diabetes, 2003. 52(1): p. 102-10.

5. Butler, A. E., et al., Diabetes due to a progressive defect in beta-cell mass in rats transgenic for human islet amyloid polypeptide (HIP Rat): a new model for type 2 diabetes. Diabetes, 2004. 53(6): p. 1509-16.

6. Donath, M. Y., et al., *Mechanisms of beta-cell death in type 2 diabetes.* Diabetes, 2005. 54 Suppl 2: p. S108-13.

7. Donath, M. Y., et al., Islet inflammation impairs the pancreatic beta-cell in type 2 diabetes. Physiology (Bethesda), 2009. 24: p. 325-31.

8. Laybutt, D. R., et al., Endoplasmic reticulum stress contributes to beta cell apoptosis in type 2 diabetes. Diabetologia, 2007. 50(4): p. 752-63.

9. Harmon, J. S., R. Stein, and R. P. Robertson, Oxidative stress-mediated, post-translational loss of MafA protein as a contributing mechanism to loss of insulin gene expression in glucotoxic beta cells. J Biol Chem, 2005. 280(12): p. 11107-13.

10. Nauta, T. D., V. W. van Hinsbergh, and P. Koolwijk, *Hypoxic signaling during tissue repair and regenerative medicine.* Int J Mol Sci, 2014. 15(11): p. 19791-815.

11. Botusan, I. R., et al., Stabilization of HIF-1alpha is critical to improve wound healing in diabetic mice. Proc Natl Acad Sci USA, 2008. 105(49): p. 19426-31.

12. Lane, A. N. and T. W. Fan, *Regulation of mammalian nucleotide metabolism and biosynthesis.* Nucleic Acids Res, 2015. 43(4): p. 2466-85.

13. Farber, J. L., *The role of calcium ions in toxic cell injury.* Environ Health Perspect, 1990. 84: p. 107-11.

14. Conacci-Sorrell, M., C. Ngouenet, and R. N. Eisenman, *Myc-nick: a cytoplasmic cleavage product of Myc that promotes alpha-tubulin acetylation and cell differentiation.* Cell, 2010. 142(3): p. 480-93.

15. Janson J, Soeller W C, Roche P C, et al. *Spontaneous diabetes mellitus in transgenic mice expressing human islet amyloid polypeptide.* Proc Natl Acad Sci USA. 1996. 93(14): p. 7283-7288.

16. Bellou, V., et al., *Risk factors for type 2 diabetes mellitus: An exposure-wide umbrella review of meta-analyses.* PLoS One, 2018. 13(3): p. e0194127.

17. Fletcher, B., M. Gulanick, and C. Lamendola, *Risk factors for type 2 diabetes mellitus.* J Cardiovasc Nurs, 2002. 16(2): p. 17-23.

18. Wu, Y., et al., *Risk factors contributing to type 2 diabetes and recent advances in the treatment and prevention.* Int J Med Sci, 2014. 11(11): p. 1185-200.

19. Bleichert, F., *Mechanisms of replication origin licensing: a structural perspective.* Curr Opin Struct Biol, 2019. 59: p. 195-204.

20. Shetty, A., et al., *DNA replication licensing and cell cycle kinetics of normal and neoplastic breast.* Br J Cancer, 2005. 93(11): p. 1295-300.

21. Ortiz-Barahona, A., et al., *Genome-wide identification of hypoxia-inducible factor binding sites and target genes by a probabilistic model integrating transcription profiling data and in silico binding site prediction.* Nucleic Acids Res, 2010. 38(7): p. 2332-45.

22. Valvona, C. J., et al., *The Regulation and Function of Lactate Dehydrogenase A: Therapeutic Potential in Brain Tumor.* Brain Pathol, 2016. 26(1): p. 3-17.

23. Zehetner, J., et al., *PVHL is a regulator of glucose metabolism and insulin secretion in pancreatic beta cells.* Genes Dev, 2008. 22(22): p. 3135-46.

24. Schuit, F. C., et al., *Glucose sensing in pancreatic beta-cells: a model for the study of other glucose-regulated cells in gut, pancreas, and hypothalamus.* Diabetes, 2001. 50(1): p. 1-11.

25. Adeva-Andany, M. M., et al., *Metabolic effects of glucagon in humans.* J Clin Transl Endocrinol, 2019. 15: p. 45-53.

26. Faerch, K., et al., *Insulin Resistance Is Accompanied by Increased Fasting Glucagon and Delayed Glucagon Suppression in Individuals With Normal and Impaired Glucose Regulation.* Diabetes, 2016. 65(11): p. 3473-3481.

27. Ahren, B. and O. Thorsson, *Increased insulin sensitivity is associated with reduced insulin and glucagon secre-* tion and increased insulin clearance in man. J Clin Endocrinol Metab, 2003. 88(3): p. 1264-70.

28. Choe, S. S., et al., *Chronic activation of liver X receptor induces beta-cell apoptosis through hyperactivation of lipogenesis: liver X receptor-mediated lipotoxicity in pancreatic beta-cells*. Diabetes, 2007. 56(6): p. 1534-43.

29. Miyazaki, S., et al., *Nuclear hormone retinoid X receptor (RXR) negatively regulates the glucose-stimulated insulin secretion of pancreatic ss-cells*. Diabetes, 2010. 59(11): p. 2854-61.

30. Dusaulcy, R., et al., *High-fat diet impacts more changes in beta-cell compared to alpha-cell transcriptome*. PLoS One, 2019. 14(3): p. e0213299.

31. Talchai, C., et al., *Pancreatic beta cell dedifferentiation as a mechanism of diabetic beta cell failure*. Cell, 2012. 150(6): p. 1223-34.

32. Coelho, D. S., et al., *Culling Less Fit Neurons Protects against Amyloid-beta-Induced Brain Damage and Cognitive and Motor Decline*. Cell Rep, 2018. 25(13): p. 3661-3673 e3.

---

What is claimed is:

1. A method of treating a subject for type 2 diabetes, the method comprising administering an effective amount of a PFKFB3 inhibitor to the subject.

2. The method of claim 1, wherein the PFKFB3 inhibitor is administered intravenously, intramuscularly, intraperitoneally, subcutaneously, orally, topically, through inhalation, or through a combination of two or more routes of administration.

3. The method of claim 1, further comprising administering a HIF1α inhibitor to the subject.

4. The method of claim 3, wherein the PFKFB3 inhibitor is N-bromoacetylethanolamine phosphate (BrAcNHEtOP), 7,8-dihydroxy-3-(4-hydroxyphenyl) chromen-4-one (YN1), ethyl 7-hydroxy-2-oxochromene-3-carboxylate (YZ9, PQP, PFK-158), (2S)—N-[4-(3-cyano-1-isobutyl-indol-5-yl)oxy-phenyl]pyrrolidine-2-carboxamide (Compound 26), (2S)—N-(4-((3-Cyano-1-((3,5-dimethyl-4-isoxazolyl)methyl)-1H-indol-5-yl)oxy)phenyl)-2-pyrrolidinecarboxamide (AZ67), KAN0436151, or KAN0438757.

5. The method of claim 3, wherein the PFKFB3 inhibitor is a nucleic acid inhibitor, an antisense oligonucleotide, an siRNA, and/or a short hairpin RNA.

6. The method of claim 3, wherein the PFKFB3 inhibitor is operatively linked to a targeting molecule configured to bind to β-cells of the subject.

7. The method of claim 6, wherein the targeting molecule is an antibody, antibody fragment, or nanobody configured to bind to a GLP-1 receptor.

8. The method of claim 6, wherein the targeting molecule is configured to bind to a GLP-1 receptor.

9. The method of claim 1, wherein the subject has been diagnosed with type 2 diabetes.

10. The method of claim 9, wherein the subject was previously treated for type 2 diabetes.

11. The method of claim 1, further comprising measuring an expression level of PFKFB3 in β-cells from the subject prior to the administering step.

12. A method of treating a subject for type 2 diabetes, the method comprising:

(a) determining a subject to have an increased expression level of PFKFB3 in β-cells from the subject relative to an expression level of PFKFB3 in β-cells from a healthy subject who is not suffering from type 2 diabetes; and (b) administering an effective amount of a PFKFB3 inhibitor to the subject.

13. The method of claim 12, wherein the subject suffers from prediabetes.

14. A method for stimulating cell death in damaged β-cells expressing PFKFB3, the method comprising providing a PFKFB3 inhibitor to the damaged β-cells.

* * * * *

SEQUENCE LISTING

```
<160> NUMBER OF SEQ ID NOS: 4

<210> SEQ ID NO 1
<211> LENGTH: 3946
<212> TYPE: DNA
<213> ORGANISM: Homo Sapiens

<400> SEQUENCE: 1
agtgcacagt gctgcctcgt ctgaggggac aggaggatca ccctcttcgt cgcttcggcc      60
agtgtgtcgg gctgggccct gacaagccac ctgaggagag gctcggagcc gggcccggac     120
cccggcgatt gccgcccgct tctctctagt ctcacgaggg gtttcccgcc tcgcaccccc     180
acctctggac ttgcctttcc ttctcttctc cgcgtgtgga gggagccagc gcttaggccg     240
gagcgagcct gggggccgcc cgccgtgaag acatcgcggg gaccgattca ccatggaggg     300
cgccggcggc gcgaacgaca agaaaaagat aagttctgaa cgtcgaaaag aaaagtctcg     360
agatgcagcc agatctcggc gaagtaaaga atctgaagtt ttttatgagc ttgctcatca     420
gttgccactt ccacataatg tgagttcgca tcttgataag gcctctgtga tgaggcttac     480
catcagctat ttgcgtgtga ggaaacttct ggatgctggt gatttggata ttgaagatga     540
catgaaagca cagatgaatt gcttttattt gaaagccttg gatggttttg ttatggttct     600
cacagatgat ggtgacatga tttacatttc tgataatgtg aacaaataca tgggattaac     660
tcagtttgaa ctaactggac acagtgtgtt tgattttact catccatgtg accatgagga     720
aatgagagaa atgcttacac acagaaatgg ccttgtgaaa aagggtaaag aacaaaacac     780
acagcgaagc ttttttctca gaatgaagtg taccctaact agccgaggaa gaactatgaa     840
cataaagtct gcaacatgga aggtattgca ctgcacaggc cacattcacg tatatgatac     900
caacagtaac caacctcagt gtgggtataa gaaaccacct atgacctgct tggtgctgat     960
ttgtgaaccc attcctcacc catcaaatat tgaaattcct ttagatagca agactttcct    1020
cagtcgacac agcctggata tgaaattttc ttattgtgat gaaagaatta ccgaattgat    1080
gggatatgag ccagaagaac ttttaggccg ctcaatttat gaatattatc atgcttttgga    1140 ctctgatcat ctgaccaaaa ctcatcatga tatgtttact aaaggacaag tcaccacagg    1200
acagtacagg atgcttgcca aaagaggtgg atatgtctgg gttgaaactc aagcaactgt    1260
catatataac accaagaatt ctcaaccaca gtgcattgta tgtgtgaatt acgttgtgag    1320
tggtattatt cagcacgact tgattttctc ccttcaacaa acagaatgtg tccttaaacc    1380
ggttgaatct tcagatatga aaatgactca gctattcacc aaagttgaat cagaagatac    1440
aagtagcctc tttgacaaac ttaagaagga acctgatgct ttaactttgc tggccccagc    1500
cgctggagac acaatcatat ctttagattt tggcagcaac gacacagaaa ctgatgacca    1560
gcaacttgag gaagtaccat tatataatga tgtaatgctc ccctcaccca cgaaaaatt    1620 acagaatata aatttggcaa tgtctccatt acccaccgct gaaacgccaa agccacttcg    1680
```

```
aagtagtgct gaccctgcac tcaatcaaga agttgcatta aaattagaac caaatccaga    1740
gtcactggaa ctttctttta ccatgcccca gattcaggat cagacaccta gtccttccga    1800
tggaagcact agacaaagtt cacctgagcc taatagtccc agtgaatatt gtttttatgt    1860
ggatagtgat atggtcaatg aattcaagtt ggaattggta gaaaaacttt ttgctgaaga    1920
cacagaagca aagaacccat tttctactca ggacacagat ttagacttgg agatgttagc    1980
tccctatatc ccaatggatg atgacttcca gttacgttcc ttcgatcagt tgtcaccatt    2040
agaaagcagt tccgcaagcc ctgaaagcgc aagtcctcaa agcacagtta cagtattcca    2100
gcagactcaa atacaagaac ctactgctaa tgccaccact accactgcca ccactgatga    2160
attaaaaaca gtgacaaaag accgtatgga agacattaaa atattgattg catctccatc    2220
tcctacccac atacataaag aaactactag tgccacatca tcaccatata gagatactca    2280
aagtcggaca gcctcaccaa acagagcagg aaaaggagtc atagaacaga cagaaaaatc    2340
tcatccaaga agccctaacg tgttatctgt cgctttgagt caaagaacta cagttcctga    2400
ggaagaacta aatccaaaga tactagcttt gcagaatgct cagagaaagc gaaaaatgga    2460
acatgatggt tcacttttc aagcagtagg aattggaaca ttattacagc agccagacga    2520
tcatgcagct actacatcac tttcttggaa acgtgtaaaa ggatgcaaat ctagtgaaca    2580
gaatggaatg gagcaaaaga caattatttt aataccctct gatttagcat gtagactgct    2640
ggggcaatca atggatgaaa gtggattacc acagctgacc agttatgatt gtgaagttaa    2700
tgctcctata caaggcagca gaaacctact gcagggtgaa gaattactca gagctttgga    2760
tcaagttaac tgagctttt cttaatttca ttccttttt tggacactgg tggctcatta    2820
cctaaagcag tctatttata ttttctacat ctaattttag aagcctggct acaatactgc    2880
acaaacttgg ttagttcaat tttgatcccc tttctactta atttacatta atgctctttt    2940
ttagtatgtt ctttaatgct ggatcacaga cagctcattt tctcagtttt ttggtattta    3000
aaccattgca ttgcagtagc atcattttaa aaaatgcacc ttttttattta tttatttttg    3060 gctagggagt ttatcccttt ttcgaattat ttttaagaag atgccaatat aatttttgta    3120
agaaggcagt aacctttcat catgatcata ggcagttgaa aaatttttac accttttttt    3180
tcacatttta cataaataat aatgctttgc cagcagtacg tggtagccac aattgcacaa    3240
tatattttct taaaaaatac cagcagttac tcatggaata tattctgcgt ttataaaact    3300
agtttttaag aagaaatttt ttttggccta tgaaattgtt aaacctggaa catgacattg    3360
ttaatcatat aataatgatt cttaaatgct gtatggttta ttatttaaat gggtaaagcc    3420
atttacataa tatagaaaga tatgcatata tctagaaggt atgtggcatt tatttggata    3480
aaattctcaa ttcagagaaa tcatctgatg tttctatagt cactttgcca gctcaaaaga    3540
aaacaatacc ctatgtagtt gtggaagttt atgctaatat tgtgtaactg atattaaacc    3600
taaatgttct gcctaccctg ttggtataaa gatattttga gcagactgta aacaagaaaa    3660
aaaaaatcat gcattcttag caaaattgcc tagtatgtta atttgctcaa aatacaatgt    3720
ttgattttat gcactttgtc gctattaaca tcctttttt catgtagatt tcaataattg    3780
agtaatttta gaagcattat tttaggaata tatagttgtc acagtaaata tcttgttttt    3840
tctatgtaca ttgtacaaat ttttcattcc ttttgctctt tgtggttgga tctaacacta    3900
actgtattgt tttgttacat caaataaaca tcttctgtgg accagg                   3946
```

<210> SEQ ID NO 2
<211> LENGTH: 826

```
<212> TYPE: PRT
<213> ORGANISM: Homo Sapiens

<400> SEQUENCE: 2

Met Glu Gly Ala Gly Gly Ala Asn Asp Lys Lys Ile Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
                100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
        130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
                180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
        210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
                260                 265                 270

Arg Ser Ile Tyr Glu Tyr Tyr His Ala Leu Asp Ser Asp His Leu Thr
                275                 280                 285

Lys Thr His His Asp Met Phe Thr Lys Gly Gln Val Thr Thr Gly Gln
        290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
                340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
        370                 375                 380

Ser Leu Phe Asp Lys Leu Lys Lys Glu Pro Asp Ala Leu Thr Leu Leu
385                 390                 395                 400
```

-continued

```
Ala Pro Ala Ala Gly Asp Thr Ile Ile Ser Leu Asp Phe Gly Ser Asn
            405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685

Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
    770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815
```

```
Glu Leu Leu Arg Ala Leu Asp Gln Val Asn
        820                 825

<210> SEQ ID NO 3
<211> LENGTH: 4226
<212> TYPE: DNA
<213> ORGANISM: Homo Sapiens

<400> SEQUENCE: 3
ccctttcccc tccctcgccc gccccgccgc ccgcaggcgc cccgagtcgc ggggctgccg       60
cttggacgtc gtcctgtctg ggtgtcgcgg gccggccccg cggggagcgc cccccggcgcg     120 atgcccttca ggaaagcctg tgggccaaag ctgaccaact cccccaccgt catcgtcatg      180
gtgggcctcc ccgcccgggg caagacctac atctccaaga agctgactcg ctacctcaac      240
tggattggcg tccccacaaa agtgttcaac gtcggggagt atcgccggga ggctgtgaag      300
cagtacagct cctacaactt cttccgcccc gacaatgagg aagccatgaa agtccggaag      360
caatgtgcct tagctgcctt gagagatgtc aaaagctacc tggcgaaaga aggggggacaa     420 attgcggttt tcgatgccac caatactact agagagagga gacacatgat ccttcatttt      480
gccaaagaaa atgactttaa ggcgttttc atcgagtcgg tgtgcgacga ccctacagtt       540
gtggcctcca atatcatgga agttaaaatc tccagcccgg attacaaaga ctgcaactcg      600
gcagaagcca tggacgactt catgaagagg atcagttgct atgaagccag ctaccagccc      660
ctcgaccccg acaaatgcga cagggacttg tcgctgatca aggtgattga cgtgggccgg      720
aggttcctgg tgaaccgggt gcaggaccac atccagagcc gcatcgtgta ctacctgatg      780
aacatccacg tgcagccgcg taccatctac ctgtgccggc acggcgagaa cgagcacaac      840
ctccagggcc gcatcggggg cgactcaggc ctgtccagcc ggggcaagaa gtttgccagt      900
gctctgagca agttcgtgga ggagcagaac ctgaaggacc tgcgcgtgtg gaccagccag      960
ctgaagagca ccatccagac ggccgaggcg ctgcggctgc cctacgagca gtggaaggcg     1020
ctcaatgaga tcgacgcggg cgtctgtgag gagctgacct acgaggagat cagggacacc     1080
taccctgagg agtatgcgct gcgggagcag gacaagtact attaccgcta ccccaccgggg    1140 gagtcctacc aggacctggt ccagcgcttg gagccagtga tcatggagct ggagcggcag     1200
gagaatgtgc tggtcatctg ccaccaggcc gtcctgcgct gcctgcttgc ctacttcctg     1260
gataagagtg cagaggagat gccctacctg aaatgccctc ttcacaccgt cctgaaactg     1320
acgcctgtcg cttatggctg ccgtgtggaa tccatctacc tgaacgtgga gtccgtctgc     1380
acacaccggg agaggtcaga ggatgcaaag aagggaccta acccgctcat gagacgcaat     1440
agtgtcaccc cgctagccag ccccgaaccc accaaaaagc ctcgcatcaa cagctttgag     1500
gagcatgtgg cctccacctc ggccgccctg cccagctgcc tgcccccgga ggtgcccacg     1560
cagctgcctg gacaaaacat gaaaggctcc cggagcagcg ctgactcctc caggaaacac     1620
tgaggcagac gtgtcggttc cattccattt ccatttctgc agcttagctt gtgtcctgcc     1680
ctccgcccga ggcaaaacgt atcctgagga cttcttccgg agagggtggg gtggagcagc     1740
gggggagcct tggccgaaga gaaccatgct tggcaccgtc tgtgtcccct cggccgctgg     1800
acaccagaaa gccacgtggg tccctggcgc cctgccttta gccgtggggc ccccacctcc     1860
actctctggg tttcctagga atgtccagcc tcggagacct tcacaaagcc ttgggagggt     1920
gatgagtgct ggtcctgaca ggaggccgct ggggacactg tgctgttttg tttcgtttct     1980
gtgatctccc ggcacgtttg gagctgggaa gaccacactg gtggcagaat cctaaaatta    2040
```

```
aaggaggcag gctcctagtt gctgaaagtt aaggaatgtg taaaacctcc acgtgactgt    2100
ttggtgcatc ttgacctggg aagacgcctc atgggaacga acttggacag gtgttgggtt    2160
gaggcctctt ctgcaggaag tccctgagct gagacgcaag ttggctgggt ggtccgcacc    2220
ctggctctcc tgcaggtcca cacaccttcc aggcctgtgg cctgcctcca aagatgtgca    2280
agggcaggct ggctgcacgg ggagagggaa gtattttgcc gaaatatgag aactgggggcc   2340 tcctgctccc agggagctcc agggcccctc tctcctccca cctggacttg gggggaactg    2400
agaaacactt tcctggagct gctggctttt gcactttttt gatggcagaa gtgtgacctg    2460
agagtcccac cttctcttca ggaacgtaga gtgttggggtg tcttgccctg gggggcttgg   2520
aacctctgaa ggtggggagc ggaacacctg gcatccttcc ccagcacttg cattaccgtc    2580
cctgctcttc ccaggtgggg acagtggccc aagcaaggcc tcactcgcag ccacttcttc    2640
aagagctgcc tgcacactgt cttggagcat ctgccttgtg cctggcactc tgccggtgcc    2700
ttgggaaggt cggaagagtg gactttgtcc tggccttccc ttcatggcgt ctatgacact    2760
tttgtggtga tggaaagcat gggacctgtc gtctcagcct gttggtttct cctcattgcc    2820
tcaaaccctg gggtaggtgg gacggggggt ctcgtgccca gatgaaacca tttggaaact    2880
cggcagcaga gtttgtccaa atgacccttt tcaggatgtc tcaaagcttg tgccaaaggt    2940 cactttttctt tcctgccttc tgctgtgagc cctgagatcc tcctcccagc tcaagggaca   3000
ggtcctgggt gagggtggga gatttagaca cctgaaactg ggcgtggaga gaagagccgt    3060
tgctgtttgt tttttgggaa gagcttttaa agaatgcatg tttttttcct ggttggaatt    3120
gagtaggaac tgaggctgtg cttcaggtat ggtacaatca agtgggggat tttcatgctg    3180
aaccattcaa gccctccccg cccgttgcac ccactttggc tggcgtctgc tggagaggat    3240
gtctctgtcc gcattcccgt gcagctccag gctcgcgcag ttttctctct ctccctggat    3300
gttgagtctc atcagaatat gtgggtaggg ggtggacgtg cacgggtgca tgattgtgct    3360
taacttggtt gtattttttcg atttgacatg gaaggcctgt tgctttgctc ttgagaatag    3420
tttctcgtgt cccccctcgca ggcctcattc tttgaacatc gactctgaag tttgatacag    3480
ataggggctt gatagctgtg gtcccctctc ccctctgact acctaaaatc aatacctaaa    3540
tacagaagcc ttggtctaac acgggacttt tagtttgcga agggcctaga tagggagaga    3600
ggtaacatga atctggacag ggaggggagat actatagaaa ggagaacact gcctactttg    3660
caagccagtg acctgccttt tgaggggaca ttggacgggg gccggggggcg ggggttgggt    3720 ttgagctaca gtcatgaact tttggcgtct actgattcct ccaactctcc accccacaaa    3780
ataacgggga ccaatatttt taactttgcc tatttgtttt tgggtgagtt tcccccctcc    3840
ttattctgtc ctgagaccac gggcaaagct cttcattttg agagagaaga aaaactgttt    3900
ggaaccacac caatgatatt tttctttgta atacttgaaa tttattttt tattattttg     3960 atagcagatg tgctatttat ttatttaata tgtataagga gcctaaacaa tagaaagctg    4020
tagagattgg gtttcattgt taattggttt gggagcctcc tatgtgtgac ttatgacttc    4080
tctgtgttct gtgtatttgt ctgaattaat gacctgggat ataaagctat gctagctttc    4140
aaacaggaga tgcctttcag aaatttgtat attttgcagt tgccagacca ataaaatacc    4200
tggttgaaat acatggacga agtaaa                                          4226
```

<210> SEQ ID NO 4
<211> LENGTH: 500
<212> TYPE: PRT
<213> ORGANISM: Homo Sapiens

```
<400> SEQUENCE: 4

Met Pro Phe Arg Lys Ala Cys Gly Pro Lys Leu Thr Asn Ser Pro Thr
1               5                   10                  15

Val Ile Val Met Val Gly Leu Pro Ala Arg Gly Lys Thr Tyr Ile Ser
            20                  25                  30

Lys Lys Leu Thr Arg Tyr Leu Asn Trp Ile Gly Val Pro Thr Lys Val
        35                  40                  45

Phe Asn Val Gly Glu Tyr Arg Arg Glu Ala Val Lys Gln Tyr Ser Ser
    50                  55                  60

Tyr Asn Phe Phe Arg Pro Asp Asn Glu Glu Ala Met Lys Val Arg Lys
65                  70                  75                  80

Gln Cys Ala Leu Ala Ala Leu Arg Asp Val Lys Ser Tyr Leu Ala Lys
                85                  90                  95

Glu Gly Gly Gln Ile Ala Val Phe Asp Ala Thr Asn Thr Thr Arg Glu
            100                 105                 110

Arg Arg His Met Ile Leu His Phe Ala Lys Glu Asn Asp Phe Lys Ala
        115                 120                 125

Phe Phe Ile Glu Ser Val Cys Asp Asp Pro Thr Val Val Ala Ser Asn
    130                 135                 140

Ile Met Glu Val Lys Ile Ser Ser Pro Asp Tyr Lys Asp Cys Asn Ser
145                 150                 155                 160

Ala Glu Ala Met Asp Asp Phe Met Lys Arg Ile Ser Cys Tyr Glu Ala
                165                 170                 175

Ser Tyr Gln Pro Leu Asp Pro Asp Lys Cys Asp Arg Asp Leu Ser Leu
            180                 185                 190

Ile Lys Val Ile Asp Val Gly Arg Arg Phe Leu Val Asn Arg Val Gln
        195                 200                 205

Asp His Ile Gln Ser Arg Ile Val Tyr Tyr Leu Met Asn Ile His Val
    210                 215                 220

Gln Pro Arg Thr Ile Tyr Leu Cys Arg His Gly Glu Asn Glu His Asn
225                 230                 235                 240

Leu Gln Gly Arg Ile Gly Gly Asp Ser Gly Leu Ser Ser Arg Gly Lys
                245                 250                 255

Lys Phe Ala Ser Ala Leu Ser Lys Phe Val Glu Glu Gln Asn Leu Lys
            260                 265                 270

Asp Leu Arg Val Trp Thr Ser Gln Leu Lys Ser Thr Ile Gln Thr Ala
        275                 280                 285

Glu Ala Leu Arg Leu Pro Tyr Glu Gln Trp Lys Ala Leu Asn Glu Ile
    290                 295                 300

Asp Ala Gly Val Cys Glu Glu Leu Thr Tyr Glu Glu Ile Arg Asp Thr
305                 310                 315                 320

Tyr Pro Glu Glu Tyr Ala Leu Arg Glu Gln Asp Lys Tyr Tyr Tyr Arg
                325                 330                 335

Tyr Pro Thr Gly Glu Ser Tyr Gln Asp Leu Val Gln Arg Leu Glu Pro
            340                 345                 350

Val Ile Met Glu Leu Glu Arg Gln Glu Asn Val Leu Val Ile Cys His
        355                 360                 365

Gln Ala Val Leu Arg Cys Leu Leu Ala Tyr Phe Leu Asp Lys Ser Ala
    370                 375                 380

Glu Glu Met Pro Tyr Leu Lys Cys Pro Leu His Thr Val Leu Lys Leu
385                 390                 395                 400

Thr Pro Val Ala Tyr Gly Cys Arg Val Glu Ser Ile Tyr Leu Asn Val
```

-continued

```
              405                 410                 415

Glu Ser Val Cys Thr His Arg Glu Arg Ser Glu Asp Ala Lys Lys Gly
            420                 425                 430

Pro Asn Pro Leu Met Arg Arg Asn Ser Val Thr Pro Leu Ala Ser Pro
        435                 440                 445

Glu Pro Thr Lys Lys Pro Arg Ile Asn Ser Phe Glu Glu His Val Ala
    450                 455                 460

Ser Thr Ser Ala Ala Leu Pro Ser Cys Leu Pro Pro Glu Val Pro Thr
465                 470                 475                 480

Gln Leu Pro Gly Gln Asn Met Lys Gly Ser Arg Ser Ser Ala Asp Ser
            485                 490                 495

Ser Arg Lys His
            500
```